US011396672B2

(12) United States Patent
He et al.

(10) Patent No.: US 11,396,672 B2
(45) Date of Patent: Jul. 26, 2022

(54) COMPOSITION AND METHODS FOR DETECTING ADENOSINE MODIFICATIONS

(71) Applicant: The University of Chicago, Chicago, IL (US)

(72) Inventors: Chuan He, Chicago, IL (US); Kai Chen, Chicago, IL (US); Qing Dai, Chicago, IL (US)

(73) Assignee: The University of Chicago, Chicago, IL (US)

( * ) Notice: Subject to any disclaimer, the term of this patent is extended or adjusted under 35 U.S.C. 154(b) by 569 days.

(21) Appl. No.: 15/756,195

(22) PCT Filed: Aug. 30, 2016

(86) PCT No.: PCT/US2016/049407
§ 371 (c)(1),
(2) Date: Jul. 16, 2018

(87) PCT Pub. No.: WO2017/040477
PCT Pub. Date: Mar. 9, 2017

(65) Prior Publication Data
US 2018/0245128 A1     Aug. 30, 2018

Related U.S. Application Data

(60) Provisional application No. 62/211,948, filed on Aug. 31, 2015.

(51) Int. Cl.
*C12Q 1/68*     (2018.01)
*C12Q 1/34*     (2006.01)
*C12Q 1/6869*   (2018.01)
*C12N 9/78*     (2006.01)
*C12Q 1/6827*   (2018.01)
*C12Q 1/6806*   (2018.01)
*C07H 21/04*    (2006.01)

(52) U.S. Cl.
CPC ............... *C12Q 1/34* (2013.01); *C12N 9/78* (2013.01); *C12Q 1/6806* (2013.01); *C12Q 1/6827* (2013.01); *C12Q 1/6869* (2013.01); *C12Y 305/04002* (2013.01); *G01N 2333/978* (2013.01)

(58) Field of Classification Search
None
See application file for complete search history.

(56) References Cited

U.S. PATENT DOCUMENTS

| 5,284,834 | A  | * | 2/1994 | Jacobson et al. | C07H 19/16 514/21.8 |
| 7,635,558 | B2 | * | 12/2009 | Madjar et al. | C12Q 1/6827 435/6.18 |
| 8,846,875 | B2 | * | 9/2014 | Schwartz et al. | C07K 1/22 530/391.1 |
| 9,012,219 | B2 | * | 4/2015 | Kariko et al. | A61K 48/0041 435/377 |
| 2008/0075662 | A1 | * | 3/2008 | Madjar et al. | C12Q 1/6827 424/9.2 |
| 2010/0184058 | A1 | * | 7/2010 | Weissmann | C12Q 1/6883 435/6.18 |
| 2013/0303385 | A1 | * | 11/2013 | Korlach et al. | C12Q 1/6827 506/4 |
| 2014/0227708 | A1 | * | 8/2014 | Cambronne | C12Q 1/6876 435/6.12 |

OTHER PUBLICATIONS

Dawson, et al., "Structure and Sequence Determinants Required for the RNA Editing of ADAR2 Substrates," *Journal of Biological Chemistry*, 279(6); 4941-4951, 2004.
Fu, et al., "Gene Expression Regulation Mediated Through Reversible $M^6$ A RNA Methylation," *Nature Reviews Genetics*, 15(5), 293-306, 2014.
Fu, et al., "$N^6$-Methyloxyadenosine Marks Active Transcription Start Sites in Chlamydomonas," *Cell*, 161(4); 879-892, 2015.
Greer, et al., "DNA Methylation of $N^6$-Adenine in C. Elegans," *Cell*, 161(4); 868-870, 2015.
He, "Grand Challenge Commentary: RNA Epigenetics?" *Nature Chemical Biology*, 6(12), 863-865, 2010.
International Search Report and Written Opinion Issued in Corresponding PCT Application No. PCT/US2016/49407, dated Dec. 30, 2016.
Jia, et al., "$N^6$-Methyladenosine in Nuclear RNA is a Major Substrate of the Obesity-Associated FTO," *Nature Chemical Biology*, 7(12), 885-887, 2011.
Jia, et al., "Reversible RNA Adenosine Methylation in Biological Regulation," *Trends in Genetics*, 29(2), 108-115, 2013.
Liu, et al., "A METTL3-METTL 14 Complex Mediates Mammalian Nuclear RNA $N^6$-Adenosine Methylation," *Nature Chemical Biology*, 10(2), 93-95, 2014.
Liu, et al., "$N^6$-Methyladenosine-Dependent RNA Structural Switches Regulates RNA-Protein Interactions," *Nature*, 518(7540), 560-564, 2015.
Liu, et al., "Probing $N^6$-Methyladenosine RNA Modification Status at Single Nucleotide Resolution in mRNA and Long Noncoding RNA," *RNA*, 19(12), 1848-1856, 2013.
Lu, et al., "Chemical Modification-Assisted Bisulfite Sequencing (CAB-Seq) for 5-Carboxylcytosine Detection in DNA," *Journal of the American Chemical Society*, 135(25); 9315-9317, 2013.
Luo, et al., "Unique Features of the $M^6$A Methylome in *Arabidopsis thaliana*," *Nature Communications*, 5; 5630, 2014.

(Continued)

*Primary Examiner* — Bradley L. Sisson
(74) *Attorney, Agent, or Firm* — Norton Rose Fulbright US LLP

(57) ABSTRACT

The current disclosure relates to methods, compositions and kits for detecting modified adenosine in a target RNA molecule. Aspects relate to a method for detecting modified adenosine in a target ribonucleic acid (RNA) comprising contacting the target RNA with an adenosine deaminase enzyme (adenosine deaminase, RNA-specific) to generate a target RNA with deaminated adenosines and sequencing the target RNA with deaminated adenosines; wherein the modified adenosine is detected when the nucleotide sequence is adenosine.

16 Claims, 20 Drawing Sheets
Specification includes a Sequence Listing.

(56) References Cited

OTHER PUBLICATIONS

Mizrahi, et al, "Nucleoside Analog Studies Indicate Mechanistic Differences Between RNA-Editing Adenosine Deaminases," *Nucleic Acids Research*, 40(19); 9825-9835, 2012.
Saikia, et al., "Genome-Wide Analysis of $N^1$-Methyl-Adenosine Modification in Human tRNAs," *RNA*, 16(7), 1317-1327, 2010.
Song, et al., "Genome-Wide Profiling of 5-Formylcytosine Reveals Its Roles in Epigenetic Priming," *Cell*, 153(3); 678-691, 2013.
Song, et al., "Selective Chemical Labeling Reveals the Genome-Wide Distribution of 5-Hydroxymethylcytosine," *Nature Biotechnology*, 29(1); 68-72, 2011.
Vukovic, et al, "Substrate Recognition and Specificity of Double-Stranded RNA Binding Proteins," *Biochemistry*, 53(21); 3457-3466, 2014.
Wang, et al., "$N^6$-Methyladenosine-Dependent Regulation of Messenger RNA Stability," *Nature*, 505(7481), 117-120, 2014.
Yang, et al., "Crystal Structures of DNA/RNA Repair Enzymes AlkB and ABH2 Bound to dsDNA," *Nature*, 452(7190); 961-965, 2008.
Yu, et al., "Base-Resolution Analysis of 5-Hydroxymethylcytosine in the Mammalian Genome," *Cell*, 149(6); 1368-1380, 2012.
Zhang, et al., "$N^6$-Methyladenine DNA Modification in *Drosophila*", *Cell*, 161(4); 893-906, 2015.
Zheng, et al., "ALKBH5 Is a Mammalian RNA Demethylase that Impacts RNA Metabolism and Mouse Fertility," *Molecular Cell*, 49(1), 293-306, 2014.
Zheng, et al., "Sprouts of RNA Epigenetics: the Discovery of Mammalian RNA Demethylases," *RNA Biology*, 10(6); 915-918, 2013.

\* cited by examiner

5'---CCGAAUUCGAUAUCAAGCUUAUCG---3'
3'---GGCUUXXGCUXUXGUUCGXXUXGC---5'

X = m⁶A: Deamination ratio on target strand ~50-60%
X = A: Deamination ratio on target strand ~20-30%

FIG. 7

```
5'---CCGAAUUCGAUAUCAAGCUU---3'  RNA
              │ RT
              ▼
5'---CCGAAUUCGAUAUCAAGCUU---3'  RNA
3'---GGCUUAAGCUAUAGUUCGAA---5'  DNA
              │ Deamination
              ▼
5'---CCGAIUUCGAUIUCAIGCUU---3'  RNA
         Strand separation 3'---GGCUUAAGCUAUAGUUCGAA---5'  DNA
              │ Digestion of DNA
              │ RNA purification
              ▼ and RT
5'---CCGAIUUCGAUIUCAIGCUU---3'  RNA
3'---GGCUCAAGCUACAGUCCGAA---5'  DNA
                Deamination
```

FIG. 9B

SEQUENCE LISTING

```
<160> NUMBER OF SEQ ID NOS: 10

<210> SEQ ID NO 1
<211> LENGTH: 669
<212> TYPE: PRT
<213> ORGANISM: Drosophila melanogaster

<400> SEQUENCE: 1

Met Leu Asn Ser Ala Asn Asn Ser Pro Gln His Pro Val Ser Ala
1               5                   10                  15

Pro Ser Asp Ile Asn Met Asn Gly Tyr Asn Arg Lys Leu Pro Gln Lys
            20                  25                  30

Arg Gly Tyr Glu Met Pro Lys Tyr Ser Asp Pro Lys Lys Lys Met Cys
        35                  40                  45

Lys Glu Arg Ile Pro Gln Pro Lys Asn Thr Val Ala Met Leu Asn Glu
    50                  55                  60

Leu Arg His Gly Leu Ile Tyr Lys Leu Glu Ser Gln Thr Gly Pro Val
65                  70                  75                  80

His Ala Pro Leu Phe Thr Ile Ser Val Glu Val Asp Gly Gln Lys Tyr
                85                  90                  95

Leu Gly Gln Gly Arg Ser Lys Lys Val Ala Arg Ile Glu Ala Ala Ala
            100                 105                 110

Thr Ala Leu Arg Ser Phe Ile Gln Phe Lys Asp Gly Ala Val Leu Ser
        115                 120                 125

Pro Leu Lys Pro Ala Gly Asn Leu Asp Phe Thr Ser Asp Glu His Leu
    130                 135                 140

Glu Asn Gly Ile Glu Asn Leu Ser Ser Ser Lys Met Phe Glu Ile Ile
145                 150                 155                 160

Gln Thr Met Leu Thr Glu Lys Leu Ser Asn Pro Thr Ser Leu Glu Gln
                165                 170                 175

Pro Thr Phe Cys Met Ser Gln Asn Val Ser Lys Ser Ala Ile Thr Val
            180                 185                 190

Asp Gly Gln Lys Lys Val Pro Asp Lys Gly Pro Val Met Leu Leu Tyr
```

```
            195                 200                 205
Glu Leu Phe Asn Asp Val Asn Phe Glu Cys Ile Asn Ile Asp Gly Ala
210                 215                 220

Gln Asn Asn Cys Arg Phe Lys Met Thr Val Thr Ile Asn Glu Lys Lys
225                 230                 235                 240

Phe Asp Gly Thr Gly Pro Ser Lys Lys Thr Ala Lys Asn Ala Ala Ala
                245                 250                 255

Lys Ala Ala Leu Ala Ser Leu Cys Asn Ile Ser Tyr Ser Pro Met Val
            260                 265                 270

Val Pro Gln Lys Asn Val Pro Leu Pro Ile Asp Asp Lys Ser Ser Ser
        275                 280                 285

Met Glu Leu Pro Gln Ile His Ala Asp Thr Ile Gly Arg Leu Val Leu
290                 295                 300

Glu Lys Phe Met Glu Val Ile Lys Gly Gln Ala Tyr Ser Arg Arg
305                 310                 315                 320

Lys Val Leu Ala Gly Ile Val Met Thr Glu Asn Met Asn Phe Cys Glu
                325                 330                 335

Ala Lys Val Ile Ser Val Ser Thr Gly Thr Lys Cys Val Ser Gly Glu
            340                 345                 350

His Met Ser Val Asn Gly Ala Val Leu Asn Asp Ser His Ala Glu Ile
        355                 360                 365

Val Ser Arg Arg Cys Leu Leu Lys Tyr Leu Tyr Ala Gln Leu Asp Leu
370                 375                 380

Gln Cys Asn Gln Ala Thr Ala Tyr Gln Ser Ile Phe Val Arg Asn Thr
385                 390                 395                 400

Asp Gly Gln Tyr Pro Tyr Lys Leu Lys Ser Gly Val His Phe His Leu
                405                 410                 415

Tyr Ile Asn Thr Ala Pro Cys Gly Asp Ala Arg Ile Phe Ser Pro His
            420                 425                 430

Glu Asn Asp Thr Gly Val Asp Lys His Pro Asn Arg Lys Ala Arg Gly
        435                 440                 445

Gln Leu Arg Thr Lys Ile Glu Ser Gly Glu Gly Thr Ile Pro Val Lys
450                 455                 460

Ser Ser Asp Gly Ile Gln Thr Trp Asp Gly Val Leu Gln Gly Gln Arg
465                 470                 475                 480

Leu Leu Thr Met Ser Cys Ser Asp Lys Ile Ala Arg Trp Asn Ile Val
                485                 490                 495

Gly Ile Gln Gly Ser Leu Leu Ser Ser Ile Ile Glu Pro Val Tyr Leu
            500                 505                 510

His Ser Ile Val Leu Gly Ser Leu Leu His Pro Glu His Met Tyr Arg
        515                 520                 525

Ala Val Cys Gly Arg Ile Glu Lys Ser Ile Gln Gly Leu Pro Pro Pro
530                 535                 540

Tyr His Leu Asn Lys Pro Arg Leu Ala Leu Val Thr Ser Ala Glu Pro
545                 550                 555                 560

Arg Asn Gln Ala Lys Ala Pro Asn Phe Gly Ile Asn Trp Thr Ile Gly
                565                 570                 575

Asp Thr Glu Leu Glu Val Asn Ser Leu Thr Gly Thr Ile Gly
            580                 585                 590

Gly Gln Val Ser Arg Ile Thr Lys Gln Ala Phe Phe Val Lys Tyr Gly
        595                 600                 605

Phe Leu Met Ala Asn Leu Pro Gly Ile Leu Val Arg Lys Val Thr Thr
610                 615                 620
```

```
Asp Tyr Gly Gln Thr Lys Ala Asn Val Lys Asp Tyr Gln Ile Ala Lys
625                 630                 635                 640

Leu Glu Leu Phe Ser Ala Phe Lys Arg Glu Asp Leu Gly Ser Trp Leu
            645                 650                 655

Lys Lys Pro Ile Glu Gln Asp Glu Phe Gly Leu Ala Glu
            660                 665

<210> SEQ ID NO 2
<211> LENGTH: 24
<212> TYPE: DNA
<213> ORGANISM: Artificial Sequence
<220> FEATURE:
<223> OTHER INFORMATION: Synthetic Primer

<400> SEQUENCE: 2
ccgaauucga uaucaagcuu aucg                                    24

<210> SEQ ID NO 3
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: N is m6A
<220> FEATURE:
<221> NAME/KEY: misc_feature
<222> LOCATION: (5)..(6)
<223> OTHER INFORMATION: N is m6A
<220> FEATURE:
<221> NAME/KEY: misc_feature
<222> LOCATION: (12)..(12)
<223> OTHER INFORMATION: N is m6A
<220> FEATURE:
<221> NAME/KEY: misc_feature
<222> LOCATION: (14)..(14)
<223> OTHER INFORMATION: N is m6A
<220> FEATURE:
<221> NAME/KEY: misc_feature
<222> LOCATION: (18)..(19)
<223> OTHER INFORMATION: N is m6A

<400> SEQUENCE: 3
cgnunngcuu gnunucgnnu ucgg                                    24

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
ccgaauucga uaucaagcuu                                         20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
ccgaauucga uaucaagcuu                                         20
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
aagcuugaua ucgaauucgg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (5)..(5)
<223> OTHER INFORMATION: N is deaminated Alanine
<220> FEATURE:
<221> NAME/KEY: misc_feature
<222> LOCATION: (12)..(12)
<223> OTHER INFORMATION: N is deaminated Alanine
<220> FEATURE:
<221> NAME/KEY: misc_feature
<222> LOCATION: (16)..(16)
<223> OTHER INFORMATION: N is deaminated Alanine

<400> SEQUENCE: 7
ccganuucga unucangcuu                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
aagcuugaua ucgaauucgg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (5)..(5)
<223> OTHER INFORMATION: N is deaminated Alanine
<220> FEATURE:
<221> NAME/KEY: misc_feature
<222> LOCATION: (12)..(12)
<223> OTHER INFORMATION: N is deaminated Alanine
<220> FEATURE:
<221> NAME/KEY: misc_feature
<222> LOCATION: (16)..(16)
<223> OTHER INFORMATION: N is deaminated Alanine
```

```
<400> SEQUENCE: 9
ccganuucga unucangcuu                                        20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
aagccugaca ucgaacucgg                                        20
```

COMPOSITION AND METHODS FOR DETECTING ADENOSINE MODIFICATIONS

CROSS-REFERENCE TO RELATED APPLICATIONS

This application claims the benefit of priority of U.S. Provisional Patent Application No. 62/211,948, filed Aug. 31, 2015, which is hereby incorporated by reference in its entirety.

STATEMENT OF GOVERNMENT SUPPORT

This invention was made with government support under contract grant number HG008935 awarded by the National Institutes of Health. The government has certain rights in the invention.

BACKGROUND OF THE INVENTION

I. Field of the Invention

The present invention relates generally to the field of molecular biology. More particularly, it concerns methods and compositions for detecting, evaluating, sequencing, and/or mapping modified adenosines.

II. Background

A central question of biology is how the flow of genetic information from DNA to RNA to protein is regulated. While transcriptional regulation—the production of messenger RNA (mRNA)—plays major roles, and has been extensively studied, protein expression ultimately determines biological phenotypes. Protein production is augmented by various post-transcriptional regulations such as mRNA structure, microRNA, and mRNA translation; each of these processes fundamentally affects the protein levels and localizations that eventually impact every biological process.

Reversible and dynamic mRNA and long non-coding RNA (lncRNA) modifications were recently discovered as being a fundamental mechanism that broadly controls protein expression at the post-transcriptional level (Jia G, et al., Nat Chem Biol. 2011; 7(12):885-7; Liu J, et al., Nat Chem Biol. 2014; 10(2):93-5; Wang X, et al., Nature. 2014; 505(7481):117-20; Zheng G, et al., Mol Cell. 2013; 49(1):18-29; and Fu Y, et al., Nat Rev Genet. 2014; 15(5):293-306).

Since then, there has been extensive research interests in profiling various mRNA/lncRNA modifications such as $N^6$-methyladenosine ($m^6A$) based on antibodies or pseudouridine ($\Psi$) based on a chemical reaction (Carlile T M, et al, Nature. 2014; 515(7525):143-6; Schwartz S, et al., Cell. 2014; 159(1):148-62; Dominissini D, et al., Nature. 2012; 485(7397):201-6; and Meyer K, Cell. 2012; 149(7):1635-46). These studies have identified the presence of a very large number of modification sites, leading to the current high interests in the epitranscriptome field. Functional explorations of RNA modifications in various biological processes have so far uncovered several new gene expression regulatory mechanisms (Liu J, et al., Nat Chem Biol. 2014; 10(2):93-5; Wang X, et al., Nature. 2014; 505(7481):117-20; Zheng G, et al., Mol Cell. 2013; 49(1):18-29; Batista P J, et al., Cell Stem Cell. 2014; 15(6):707-19; Chen T, et al., Cell Stem Cell. 2015; 16(3):289-301; Geula S, et al., Science. 2015; 347(6225):1002-6; Ping X-L, et al., Cell Res. 2014; 24(2):177-89; Schwartz S, et al., Cell. 2013; 155(6):1409-21; and Wang Y, et al., Nat Cell Biol. 2014; 16(2):191-8). RNA modification is a highly fertile ground where additional regulatory mechanisms will be discovered. In particular, mRNA/lncRNA modifications are expected to be increasingly associated with human health and diseases as the field progresses.

Despite the functional significances and potential associations with human diseases, mRNA/lncRNA modifications have been studied with methods confined to either antibody-based immunoprecipitations or applications of decades-old chemical approaches; all these methods are significantly limited in resolution and sensitivity. Therefore, there is a need in the art for new methods of detecting RNA modifications.

SUMMARY OF THE INVENTION

The current disclosure addresses the aforementioned need in the art and describes a new generation of sequencing technology that can be applied generally in order to obtain highly sensitive and single-base-resolution mapping of different RNA modifications. Described herein is a method for detecting modified adenosine in a target ribonucleic acid (RNA) comprising contacting the target RNA with an adenosine deaminase enzyme to generate a target RNA with deaminated adenosines and sequencing the target RNA with deaminated adenosines; wherein any modified adenosine in the target RNA is read as an adenosine in the sequencing of the target RNA with deaminated adenosines. In some embodiments of any of the methods, kits, and compositions described herein, the adenosine deaminase enzyme is ADAR (adenosine deaminase, RNA-specific). In some embodiments, the adenosine deaminase enzyme is RNA specific. In some embodiments, the adenosine deaminase enzyme lacks significant sequence specificity or is non-sequence specific. In some embodiments, the adenosine deaminase enzyme works on double-stranded nucleic acids.

Adenosine deaminase enzymes include, for example, adenosine deaminases from any organisms such as humans (ADA, GenBank Accession: NP_000013), mouse (ADA, GenBank Accession: NP_001258981), *Drosophila melanogaster* (SEQ ID NO:1); RNA adenosine deaminase from humans (GenBank Accession: AAB97118), cows (GenBank Accession: XP_010801274.1), rat (GenBank Accession: EDM00617). The sequences associated with each of these is herein incorporated by references in their entirety.

In some embodiments, the method further comprises contacting target RNA with a demethylating enzyme; contacting the demethylated target RNA with the adenosine deaminase enzyme to produce control RNA; and sequencing the control RNA; wherein any modified adenosine in the target RNA is read as a guanosine in the sequencing of the control RNA with deaminated adenosines. In further embodiments, the demethylated target RNA is made by methods and steps described herein for generating controls. In some embodiments, the method further comprises comprising comparing the sequence of the target RNA with dominated deaminated adenosines to the sequence of the demethylated target RNA. In some embodiments, the demethylating enzyme is an N6-methyladenosine-specific demethylating enzyme. In some embodiments, the demethylating enzyme is ALKBH5 or FTO. FTO (fat mass and obesity associated) and ALKBH5 (alkB homolog 5, RNA demethylase or alkB, alkylation repair homolog 5) are demethylating enymes specific for $N^6$-methyladenosine. FTO and ALKBH5 are known in the art. The enzyme may be recombinantly made or synthetic, and may be from any species. In some embodiments, the enzyme is the mammalian enzyme. The human ALKBH5 is represented by GenBank Accession Nos: NM_017758.3 (mRNA) and NP_060228.3 (protein). The mouse ALKBH5 is represented by GenBank Accession Nos.: NM_172943.4 (mRNA) and NP_766531.2 (protein). The human FTO is represented by GenBank Accession Nos.: XM_011523313.1 (mRNA), XP_011521615.1 (protein), XM_011523316.1 (mRNA), XP_011521618.1 (protein), XM_011523314.1 (mRNA) XP_011521616.1 (protein), XM_011523315.1 (mRNA), and XP_011521617.1 (protein). In some embodiments, the demethylating enzyme is ALKBH5. The sequences associated with each of these GenBank accession numbers is herein incorporated by reference for all purposes. In some embodiments, the demethylating enzyme is from insects. In some embodiments, the demethylating enzyme is from *Drosophila melanogaster*.

In some embodiments, the target and/or demethylated target RNA is in a duplex with a complementary strand of RNA or DNA. In some embodiments, the complementary strand is DNA. In some embodiments, the complementary strand comprises modified adenosine. The modified adenosine may be one known in the art and/or described herein. In some embodiments, the modified adenosine is $N^6$-methyladenosine or $N^1$-methyladenosine.

ADAR encodes the enzyme responsible for RNA editing by site-specific deamination of adenosines. This enzyme destabilizes double-stranded RNA through conversion of adenosine to inosine. The ADAR may be from any organisms such as human, mouse, insect, etc . . . . In some embodiments, the ADAR is from *Drosophila melanogaster*, which is abbreviated dADAR In some embodiments, the ADAR is from insects. The ADAR may be synthetically made or recombinantly made. Methods of producing and purifying enzymes are known in the art.

The target RNA may be any type of RNA in a cell. In some embodiments, the target RNA is mRNA, lncRNA, pri-microRNA, pre-piRNA, rRNA, tRNA, snoRNA, or snRNA. In some embodiments, the target RNA is mRNA or lncRNA. In some embodiments, the method further comprises isolating RNA. In some embodiments, the method comprises isolating a specific RNA. The term isolating, in this context, refers to the separation of one type of RNA from other types of RNA. Therefore, the isolated RNA fraction may contain at least, at most, or exactly about 75, 80, 85, 90, 95, 96, 97, 98, 99, or 100% (or any derivable range therein) of a specific RNA type. In some embodiments, the term isolated also refers to something that is separated from cellular components and/or is free of cellular materials.

In some embodiments, the method further comprises generating a nucleic acid strand that is complementary with the target and/or demethylated target RNA and hybridizing the complementary nucleic acid strand with the target RNA and/or demethylated target RNA. Methods of generating complementary nucleic acid strands are known in the art and described herein. In some embodiments, generating the nucleic acid strand that is complementary with the target and/or demethylated target RNA comprises synthesis of a nucleic acid strand complementary to the target and/or demethylated target RNA. In some embodiments, the synthesis of the nucleic acid strand comprises a synthesis reaction composition comprising adenosine triphosphate, wherein all of the adenosine triphosphate is modified adenosine triphosphate. In some embodiments, the complementary nucleic acid strand comprises modified adenosines.

When the term "modified adenosines" is used herein, the modified adenosine may be any modified adenosine known in the art and/or described herein. In some embodiments of the methods, compositions, and kits of the disclosure, the modified adenosine is $N^6$-methyladenosine. In some embodiments, the modified adenosine is $N^1$methyladenosine. In some embodiments, the nucleic acid may comprise more than one type of adenosine modification. In some embodiments, the method further comprises determining the type of modification in a type of RNA.

In some embodiments, the complementary nucleic acid strand is RNA. In some embodiments, the complementary nucleic acid strand is DNA.

In some embodiments, the target and/or demethylated target RNA is contacted with an RNA polymerase to synthesize a complementary RNA strand. The RNA polymerase may be any RNA polymerase known in the art. In some embodiments, the method further comprises contacting the target and/or demethylated target RNA with a RNA replicase to synthesize a complementary RNA strand. In some embodiments, the RNA replicase is Phi6. In further embodiments, the RNA replicase is one known in the art. In some embodiment, the method comprises synthesis of a complementary nucleic acid from a cDNA library. In some embodiments, the complementary nucleic acid strand is RNA.

In some embodiments, the target RNA is immobilized on a solid support. Solid supports are known in the art and include, for example, glass, plastics, polymers, metals, metalloids, ceramics, organics, beads, agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc.

In some embodiments, the target RNA strand is labeled. As used herein, the term "label" intends a directly or indirectly detectable compound or reactable functional group useful for attachment of nucleic acids to solid supports. The label may also be conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

In some embodiments, the label is a compound or reactable functional group useful for attachment of a nucleic acid to a solid support. In some embodiments, the label is a phosphorothioate group. In some embodiments, the target RNA is immobilized by reaction of the phosphothioate group with a thiol-reactive group. In some embodiments, the thiol-reactive group is iodoacetamide, maleimide, or methanethiosulfonate.

In some embodiments, the target RNA is fragmented prior to immobilization on the solid support. In some embodiments, the RNA is fragmented into RNA molecules 50-300 nucleotides in length. In some embodiments, the RNA is fragmented into RNA molecules 10, 20, 30, 40, 50, 60, 70, 80, 90, 100, 120, 140, 160, 180, 200, 225, 250, 275, 300, 350, 400, 450, or 500 to 60, 70, 80, 90, 100, 120, 140, 160, 180, 200, 225, 250, 275, 300, 350, 400, 450, 500, 1000, 1500, or 2000 (or any range derivable therein) nucleotides in length. In some embodiments, the average RNA molecule fragment is about 25, 50, 75, 80, 85, 90, 95, 100, 110, 120, 130, 140, 150, 160, 170, 180, 190, 200, 220, 240, 260, 280, 300, 325, 350, 375, 400, 450, 500, or 600 nucleotides in length. In some embodiments, the target RNA is fragmented prior to immobilization.

In some embodiments, the method comprises one or more of the following steps: fragmenting the target RNA; contacting the target and/or demethylated target RNA with RNA replicase to synthesize a complementary RNA strand that forms a duplex with the target RNA or demethylated target RNA; denaturing of the RNA duplex to create mobilized complementary RNA; further comprises removal of the mobilized complementary RNA; and/or mobilizing the target RNA by separating it from the solid support. In some embodiments, mobilizing the target RNA is done by silver (I)-mediated cleavage (for phosphothiolate linkage). In some embodiments, mobilizing the target RNA further comprises proteinase K digestion and/or biotin completion (for biotin-based linkage). In some embodiments, sequencing of the target RNA comprises construction of a library of nucleic acid molecules comprising the target RNA sequence.

In some embodiments, the method comprises the steps of a) immobilizing the target RNA, b) contacting the target and/or demethylated target RNA with RNA replicase to synthesize a complementary RNA strand that forms a duplex with the target RNA or demethylated target RNA, c) contacting the target RNA with an adenosine deaminase enzyme to generate a target RNA with deaminated adenosines, d) denaturing of the RNA duplex to create mobilized complementary RNA; e) removal of the mobilized complementary RNA; and f) sequencing of the target RNA. In some embodiments, the steps a-f are sequential. In some embodiments, step a is performed followed by iterative rounds of the ordered steps of b-e, followed by step f. In some embodiments, steps b-e are repeated in iterative cycles for one or more times prior to step f. For example, one method includes three iterative rounds of steps b-e, which includes performing the following steps in the following order: step a, b, c, d, e, b, c, d, e, b, c, d, e, f. In some embodiments, steps b-e are repeated at least, at most, or exactly 2, 3, 4, 5, 6, 7, 8, 9, 10, 15, 20, 25, 30, 50, 75, or 100 times (or any derivable range therein).

In some embodiments, the method further comprises contacting the target and/or demethylated target RNA with reverse transcriptase to synthesize a complementary DNA strand.

The target and/or demethylated target RNA may be of any length. In some embodiments, the target RNA is 10-1000 nucleic acids in length. In some embodiments the target RNA is at least, at most, or exactly about 5, 10, 20, 30, 40, 50, 60, 70, 80, 100, 150, 200, 300, 400, 500, 600, 700, 800, 900, 1000, 1500, 2000, 2500, 3000, 4000, 5000, 7500, or 10000 nucleic acids in length, or any derivable range therein. In some embodiments, nucleic acid molecules may be DNA, RNA, or a combination of both. Nucleic acids may be recombinant, genomic, or synthesized. In additional embodiments, methods involve nucleic acid molecules that are isolated and/or purified. The nucleic acid may be isolated from a cell or biological sample in some embodiments. Certain embodiments involve isolating nucleic acids from a eukaryotic, mammalian, or human cell. In some cases, they are isolated from non-nucleic acids. In some embodiments, the nucleic acid molecule is eukaryotic; in some cases, the nucleic acid is mammalian, which may be human. This means the nucleic acid molecule is isolated from a human cell and/or has a sequence that identifies it as human. In particular embodiments, it is contemplated that the nucleic acid molecule is not a prokaryotic nucleic acid, such as a bacterial nucleic acid molecule. In additional embodiments, isolated nucleic acid molecules are on an array. In particular cases, the array is a microarray. In some cases, a nucleic acid is isolated by any technique known to those of skill in the art, including, but not limited to, using a gel, column, matrix or filter to isolate the nucleic acids. In some embodiments, the gel is a polyacrylamide or agarose gel.

In some embodiments, the sequence of the target and/or demethylated target RNA is known. The term sequence as used herein refers to the nucleotide sequence such as "A" for adenosine, "G" for guanine, "C" for cytosine, "T" for thymine, and "U" for uracil. Eventhough the sequence is known, it may not be known whether the nucleic acid bases are modified or unmodified.

In some embodiments, the method further comprises comparing the known sequence of the target RNA with the sequence of the target RNA with deaminated adenosines.

In some embodiments, contacting the target and/or demethylated target RNA with ADAR is done in the presence of GTP. In some embodiments, the GTP is in a concentration of 0.5-5 mM. In some embodiments the concentration of GTP in the solution is at least, at most, or exactly about 0.1, 0.2, 0.3, 0.4, 0.5, 0.8, 1.0, 1.5, 2.0, 2.5, 3.0, 3.5, 4.0, 4.5, 5.0, 5.5, 6.0, 7.0, 8.0, 9.0, 10, 15, 20, 30, 40, 50, 100, 200, 300, 400, or 500 mM (or any derivable range therein).

In some embodiments, the target RNA molecule is in a duplex with a DNA molecule. In some embodiments, the method comprises contacting the RNA-DNA duplex with a DNA digesting agent prior to sequencing the RNA. The DNA digesting enzyme may be sequence specific or non-specific. In some embodiments, the DNA digesting enzyme is DNase.

In some embodiments, the method further comprises the steps of: a) generating a DNA strand that is complementary to the target and/or demethylated target RNA and hybridizing the complementary DNA strand with the target and/or demethylated target RNA to generate an RNA-DNA duplex; b) contacting the RNA-DNA duplex with the adenosine deaminase enzyme; and c) contacting the RNA-DNA duplex with a DNA digesting agent; wherein all the steps are done prior to DNA target RNA sequencing. In some embodiments, the method further comprises repeating steps a, b, and/or c one or more times. In some embodiments, the steps are repeated at least two more times. In some embodiments, the steps a, b, and/or c are repeated at least, at most, or exactly 2, 3, 4, 5, 6, 7, 8, 9, 10, 15, 20, 25, 30, 35, 40, 45, or 50 more times, or any derivable range therein. In some embodiments, the method further comprises step of strand separation after step b). In some embodiments, the method further comprises purification of the target and/or demethylated target RNA after step c) and prior to DNA target RNA sequencing.

In some embodiments, the method further comprises providing a quantification RNA control comprising a known percentage of modified adenosine; contacting the quantification control RNA with the adenosine deaminase enzyme; and sequencing the deaminated quantification control RNA. In some embodiments, 0, 25, 50, 75, or 100% of the adenosine in the quantification RNA control is modified. In some embodiments, the method comprises at least, at most, or exactly 1, 2, 3, 4, 5, 6, 7, 8, 9, or 10 quantification controls (or any derivable range therein). In each of the quantification controls, at least, at most, or exactly 0, 5, 10, 15, 20, 25, 30, 35, 40, 45, 50, 55, 60, 65, 70, 75, 80, 85, 90, 95, or 100% (or any derivable range therein) of the adenosines may me modified.

Further aspects of the disclosure relate to a kit comprising: an adenosine deaminase enzyme and instructions for detecting modified adenosines in target RNA. In some embodiments, the kit further comprises a control nucleic acid. The control nucleic acid may be any embodiment described herein. In some embodiments, the control nucleic acid comprises a non-naturally occurring nucleic acid or non-widely present nucleic acid. In some embodiments, the control nucleic acids are are a non-naturally occurring nucleic acid sequence. In some embodiments, the control nucleic acid comprises RNA or DNA comprising modified adenosines. In some embodiments, the percentage of adenosines that are modified in the control nucleic acid is known. In some embodiments, at least, at most, or exactly 0, 5, 10, 15, 20, 25, 30, 35, 40, 45, 50, 55, 60, 65, 70, 75, 80, 85, 90, 95, or 100% (or any derivable range therein) of the adenosines in the control nucleic acid are modified. In some embodiments, the control nucleic acid comprises a duplex with a complementary nucleic acid strand. In some embodiments, the complementary nucleic acid strand is DNA. In some embodiments, the complementary nucleic acid strand is RNA with modified adenosines. In some embodiments, the kit further comprises an adenosine demethylase. The adenosine demethylase may be one known in the art and/or described herein. In some embodiments, the adenosine demethylase is specific for $N^6$-methyladenosine. In some embodiments, the adenosine demethylase is specific for $N^1$methyladenosine. In some embodiments, the kit further comprises an adenosine deaminase enzyme reaction composition comprising GTP. In some embodiments, the kit further comprises a DNase. In some embodiments, the kit further comprises a reverse transcriptase. In some embodiments, the kit further comprises a molecule or embodiment described herein in the methods and compositions. In some embodiments, the kit further comprises reagents to perform the method steps described herein, such as immobilization reagents, enzymes, and buffers described throughout the disclosure.

Further aspects relate to a method for detecting modified adenosine in a target ribonucleic acid (RNA) comprising contacting a double-stranded nucleic acid molecule comprising the target RNA with the adenosine deaminase enzyme to generate a target RNA with deaminated adenosines and sequencing the target RNA with deaminated adenosines; wherein the modified adenosine is detected when the sequence of the target RNA with deaminated adenosines is adenosine.

A further aspect relates to a method for detecting modified adenosine in a target ribonucleic acid (RNA) comprising: a) providing a target RNA; b) generating a DNA strand that is complementary with the target RNA and hybridizing the complementary DNA strand with the target RNA to generate a RNA-DNA duplex comprising the target RNA; c) contacting the RNA-DNA duplex with the adenosine deaminase enzyme to generate target RNA with deaminated adenosines; and d) contacting the RNA-DNA duplex with a DNA digesting agent; and e) sequencing the target RNA with the deaminated adenosines.

A further aspect relates to a method for detecting modified adenosine in a target ribonucleic acid (RNA) comprising: a) providing a target RNA; b) generating a DNA strand that is complementary with the target RNA and hybridizing the complementary DNA strand with the target RNA to generate a RNA-DNA duplex comprising the target RNA; c) contacting the RNA-DNA duplex with the adenosine deaminase enzyme to generate target RNA with deaminated adenosines; and d) contacting the RNA-DNA duplex with a DNA digesting agent; e) repeating steps b, c, and d one or more times; and f) sequencing the target RNA with the deaminated adenosines.

A further aspect relates to a method for detecting modified adenosine in a target ribonucleic acid (RNA) comprising: a) providing a target RNA; b) generating an RNA strand with modified adenosine that is complementary with the target RNA to generate an RNA-RNA duplex comprising the target RNA; c) contacting the RNA-RNA duplex with the adenosine deaminase enzyme to generate target RNA with deaminated adenosines; and d) sequencing the target RNA with the deaminated adenosines.

In certain embodiments, the enzymes and/or nucleic acids used in the methods, kits, and compositions described herein may comprise one or more detectable moieties and/or modification. A detectable moiety refers to a chemical compound or element that is capable of being detectedIn certain embodiments, a detectable moiety is fluorescent, radioactive, enzymatic, electrochemical, or colorimetric. In some embodiments, the detectable moiety is a fluorophore or quantum dot. In some embodiments, a modification moiety may be a linker that allows one or more functional or detectable moieties or isolation tags to be attached to the molecules. In some embodiments the linker is an azide linker or a thiol linker. In further embodiments, the modification moiety may be an isolation tag, which means the tag can be used to isolate a molecule that is attached to the tag. In certain embodiments, the isolation tag is biotin, Flag, or a histidine tag. In some cases, the tag is modified, such as with a detectable moiety. It is contemplated that the linker allows for other chemical compounds or substances to be attached to the molecule.

Methods and compositions may also involve one or more enzymes. In some embodiments, the enzyme is a restriction enzyme or a polymerase. In certain cases, embodiments involve a restriction enzyme. The restriction enzyme may be methylation-insensitive. In other embodiments, the enzyme is polymerase.

Methods may involve identifying adenosine modifications in the nucleic acids by comparing modified nucleic acids with unmodified nucleic acids or to nucleic acids whose modification state is already known. Detection of the modification can involve a wide variety of recombinant nucleic acid techniques. In some embodiments, a modified nucleic acid molecule is incubated with polymerase, at least one primer, and one or more nucleotides under conditions to allow polymerization of the modified nucleic acid. In additional embodiments, methods may involve sequencing a modified nucleic acid molecule. In other embodiments, a modified nucleic acid is used in a primer extension assay.

Methods and compositions may involve a control nucleic acid. In addition to the controls described herein, control may also be used to evaluate whether modification or other enzymatic or chemical reactions are occurring. Alternatively, the control may be used to compare modification states. The control may be a negative control or it may be a positive control. It may be a control that was not incubated with one or more reagents in the modification reaction. Alternatively, a control nucleic acid may be a reference nucleic acid, which means its modification state (based on qualitative and/or quantitative information related to modification at adenosines, or the absence thereof) is used for comparing to a nucleic acid being evaluated. In some embodiments, multiple nucleic acids from different sources provide the basis for a control nucleic acid. In some embodiments, the control is a pool of target RNA that has undergone demethylation. Moreover, in some cases, the control nucleic acid is from a normal sample with respect to a particular attribute, such as a disease or condition, or other phenotype. In some embodiments, the control sample is from a different patient population, a different cell type or organ type, a different disease state, a different phase or severity of a disease state, a different prognosis, a different developmental stage, etc.

Embodiments also concern kits, which may be in a suitable container, that can be used to achieve the described methods. In further embodiments, a kit may include one or more buffers, such as buffers for nucleic acids or for reactions involving nucleic acids. Other enzymes may be included in kits in addition to the adenosine deaminase enzyme. In some embodiments, an enzyme is a polymerase. Kits may also include nucleotides for use with the polymerase. In some cases, a restriction enzyme, (e.g. DNase) is included in addition to or instead of a polymerase.

Other embodiments also concern an array or microarray containing nucleic acid molecules that have been modified at adenosines.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7. The replacement of A with $m^6A$ on the "antisense" strand significantly improves deamination ratio by recombinant dADAR (SEQ ID NOs: 2 and 3).

FIGS. 9A-B. (A) A new buffer system (buffer 2—second bar of each series) leads to elevated deamination of A in dsRNA and noticeable deamination of A in a RNA-DNA hybrid duplex by dADAR. (B) Iterative RT-deamination-DNA digestion-RT to improve the deamination efficiency of A using RNA-DNA hybrid duplex as the substrate. An example sequence is shown here (SEQ ID NOs: 4-10).

DETAILED DESCRIPTION OF THE INVENTION

Figure 5A:
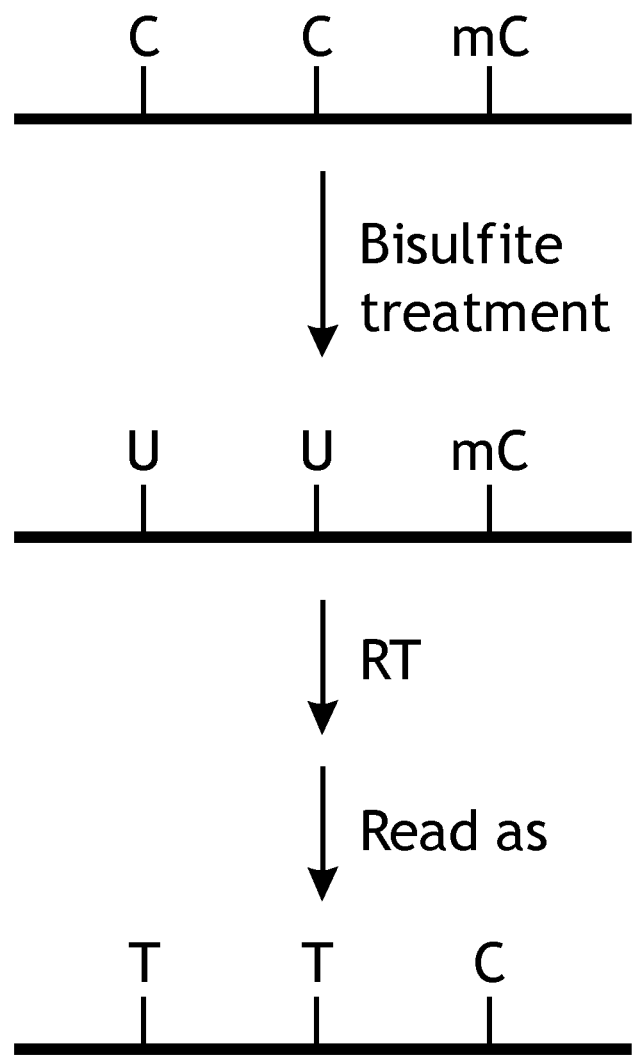
FIGS. 5A-B. To differentiate a modified base from the unmodified base in DNA and RNA sequencing, a method to selectively "mutate" the unmodified or modified base is required. In bisulfite sequencing (A), the bisulfite treatment selectively converts C to U. We propose strategies to selectively mutate A (but not $m^6A$) to I (B) by deamination.

Certain embodiments are directed to methods and compositions for detecting modified adenosine in a target ribonucleic acid (RNA) by contacting the target RNA with an adenosine deaminase enzyme (adenosine deaminase, RNA-specific). In some embodiments, the adenosine deaminase enzyme is ADAR. The ADAR enzyme deaminates unmodified adenosines, converting them to inosines. ADAR enzymes, such as those expressed and purified from insect cells, are highly active against unmodified adenosines, but possesses over 50-fold lower activity towards modified adenosines, such as $m^6A$, for example, compared to unmodified adenosine (Véliz E A, et al., Journal of the American Chemical Society. 2003; 125(36):10867-76). Therefore, after selective deamination of all adenosines in the transcriptome and subsequent reverse transcriptase (RT)-PCR followed by sequencing, only modified adenosines will be read as "A" (FIG. 5A).

I. RNA Modification

Dynamic chemical modifications of DNA and histone proteins represent fundamental mechanisms of biological regulation. Post-transcriptional modifications are also ubiquitous in RNA. To date, over 100 different RNA modifications have been identified with a wide variety of chemical diversities. Examples of such modifications can be found on the world wide web at rna-mdb.cas.albany.edu/RNAmods/, and the contents of this website publication are herein incorporated by reference. Unlike genomic DNA that tends to have limited variation of chemical modifications, the wide variety of RNA modifications appears to be a strategy used by nature to entail and facilitate a much greater diversity of structures and cellular functions for different RNA species. The $m^6A$ modification in mRNA/lncRNA alone is known to modulate the affinity for RNA-binding proteins, control subcellular localization, lifetime, storage, transport, and translation of mRNAs, switch secondary structures of RNAs, as well as to affect innate immune response.

The explosive discoveries of functional RNAs in the last decade have changed the current views on the functions of RNA and biological mechanisms that control RNA. However, the exact roles of most RNA modifications remain unknown. Certain RNA modifications are essential for life, with defects of RNA-modifying enzymes known to be associated with diverse human diseases. Most studies before 2011 on RNA modifications were limited to the abundant RNAs such as rRNA, snRNA, or tRNA. The positions of these modifications can be studied with RNA digestion followed by traditional liquid chromatography separation coupled with mass spectrometry or thin-layer chromatography due to their high abundances. The limit to these methods is their sensitivity; they cannot be applied to map modifications in low abundant mRNAs and lncRNAs, most of which appear to play critical roles in regulating gene expression. The methods of the current disclosure provide new opportunities to investigate distributions of not only mRNA and lncRNA modifications but also dynamic modifications on tRNA, snRNA, and rRNA that could not be effectively probed transcriptome-wide in the past. The methods and compositions of the disclosure can be readily applied to any class of RNA. The ability to identify all adenosine modifications at single-base resolution will significantly advance the frontier of epitranscriptomics and enable transcriptome-wide investigations that associate genomic variations and mutations with human health and diseases.

Figure 1:
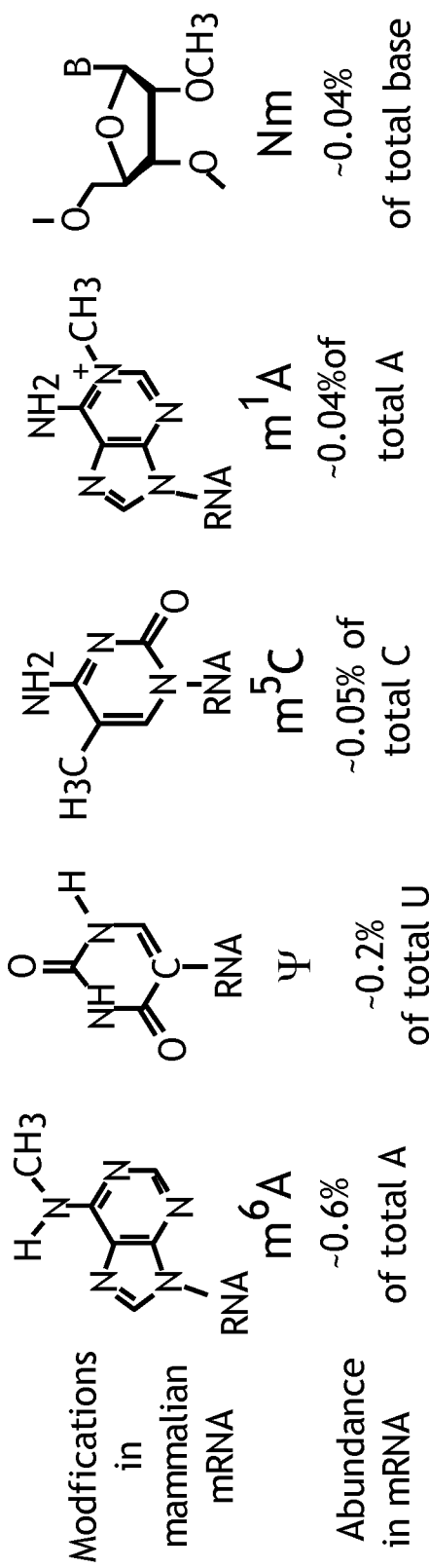
FIG. 1. The relatively abundances of known internal modifications in mammalian mRNA and lncRNA as measured by LC-MS/MS.

Mammalian mRNA and lncRNA can be modified at tens of thousands of sites. Many of these modifications are conserved in almost all eukaryotes. We have measured the relative abundances of all known mammalian internal mRNA modifications that include $N^6$-methyladenosine ($m^6A$), pseudouridine (Ψ), 5-methylcytosine ($m^5C$), $N^1$-methyladenosine ($m^1A$), and 2'O-methylation (Nm) (FIG. 1). Applicant's liquid chromatography-tandem mass spectrometry (LC-MS/MS) quantifications confirmed that these five modifications are the most abundant ones in mammalian mRNA/lncRNA. As previously known, $m^6A$ is the most prevalent internal modification in eukaryotic mRNA with ~3 per mRNA in mammalian cells. This modification plays essential and broad roles in cell differentiation, cell development, and numerous other cellular processes. The frequency of the other modifications range from 0.2-1 per mRNA in mammalian cells; some of them have been shown to have significant functional implications.

A. $N^6$-methyladenosine ($m^6A$)

Figure 2:
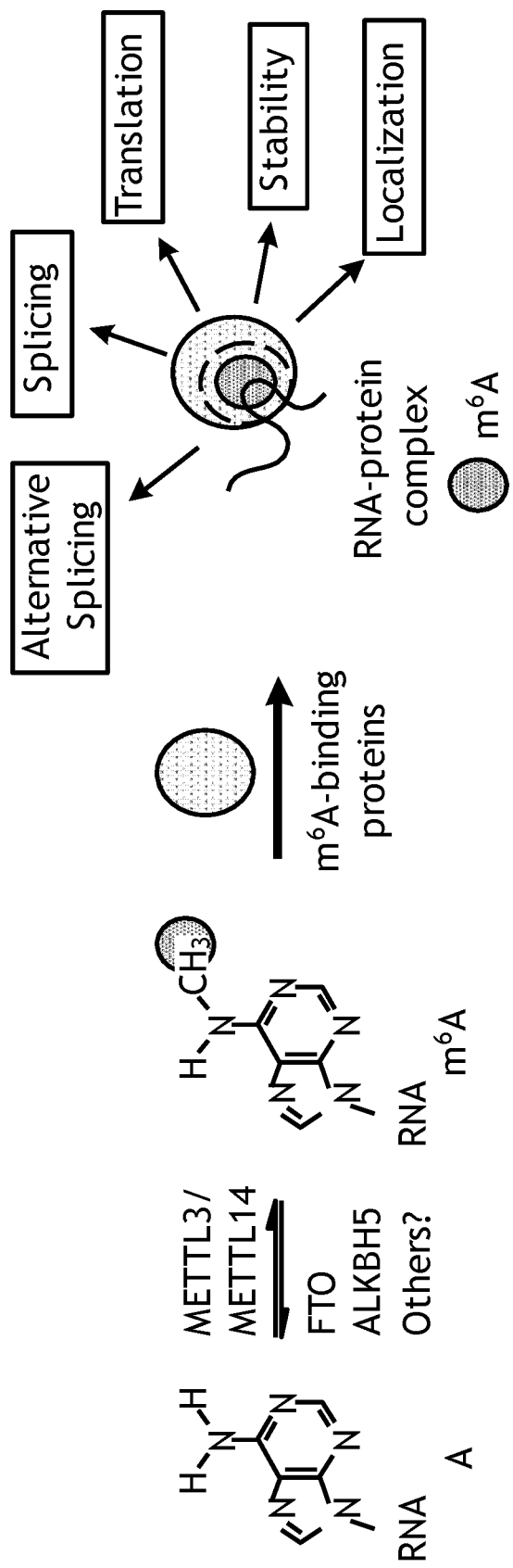
FIG. 2. The $m^6A$ modification affects a wide range of different properties and functions associated with mRNA and lncRNA.

$m^6A$ occurs at a high frequency in RNA (e.g. mRNA or lnc RNA). It is also reversible and dynamically regulated. The $m^6A$ modification appears to affect almost every phase of mRNA metabolism and function, thereby impacting diverse biological processes. Therefore, $m^6A$ studies so far embody the concept of "epitranscriptome"; its functional significance and implementation are exerted by three groups of proteins: "writers" that install, "erasers" that remove, and "readers" that bind or recognize $m^6A$ in order to determine the cellular fate of the modified mRNA/lncRNA (FIG. 2).

In mammals, $m^6A$ is installed by a three-protein core complex comprised of two catalytic subunits, METTL3/METTL14 and an accessory factor WTAP. Depletion of METTL3 homologs readily leads to developmental arrest or defects in gametogenesis in yeast, flies, and plants. In zebra fish, knockdown of METTL3 leads to smaller head, eyes, and brain ventricle, and curved notochord. The phenotypes in mammals are more severe. Both methyltransferases METTL3 and METTL14 are essential in mammals. $m^6A$ is a critical regulator in the differentiation of mouse embryonic stem cells (mESCs).

The $m^6A$ modification plays a key role in facilitating transition of mESCs from the naïve state to the primed state upon differentiation. Mettl3-depleted mESCs preserved their "naïve" pluripotent identity, but failed to proceed into the "primed" EpiSC-like state, hence blocking the subsequent differentiation; they also failed to differentiate into normal embryoid bodies (EBs) and mature neurons upon corresponding inductions. In naïve ESCs and primed EBs, the $m^6A$ modification was detected in 80% of transcripts of naïve pluripotency genes (e.g., Nanog, Klf4, Sox2, Esrrb), as well as multiple lineage commitment regulators (e.g., Foxa2, Sox17). In general, $m^6A$ deposition in mESCs decreases the expression of methylated transcripts and directly reduces their stability. Therefore, $m^6A$ loss increased the abundance and prolonged the lifetimes of naïve pluripotency transcripts. Silencing METTL3 also leads to mRNA processing delay and circadian period elongation. $m^6A$ depletion prolongs nuclear retention and delays nuclear exit of mature mRNAs of clock genes Per2 and Arntl. This result reveals an important physiological function of $m^6A$ in setting the pace of the circadian cycle and determining the clock speed and stability by controlling nuclear RNA export. A recent study described that microRNAs (miRNAs) could regulate $m^6A$ modification via a sequence-pairing mechanism in order to modulate the binding of METTL3 to mRNA substrates. Another recent study uncovered that $m^6A$ on pri-miRNA plays critical roles in miRNA maturation. The inhibition of pri-miRNA methylation induced delayed maturation of 70% of all miRNA, resulting in >30% changes of mature miRNA levels.

$m^6A$ on mRNA can be reversed by two RNA demethylases, FTO and ALKBH5. Defects of FTO and AlkBH5 lead to altered metabolism, neural development retardation, and compromised spermatogenesis. A common variant of the FTO gene (an intron mutation) has been shown to generate a predisposition to obesity. Knockout mouse models revealed that FTO is important to development: most knockout mice die at the embryo state or within the first month of birth; those that survived tended to lose body weight and were smaller compared to the control mice. A mutation of the human FTO coding region has also been linked to mental retardation. The Alkbh5 knockout male mice exhibit significant spermatogenesis defects with compromised fertility. The fact that FTO and ALKBH5 show noticeable but very different phenotypes in humans or mice strongly indicates that reversible $m^6A$ RNA methylation plays important roles in biological regulation.

$m^6A$ is recognized by "reader" proteins to exhibit biological functions, just like the interplay between DNA cytosine-methylation and methyl-CpG-binding proteins that regulate gene expression through binding to methylated cytosines. Applicants have identified several $m^6A$-specific binding proteins in humans that belong to the YTH family: YTHDF1, YTHDF2, and YTHDC1. All these proteins bind the $m^6A$-containing RNA selectively over unmethylated RNA through direct accommodation of the methyl group in their structures. Functional characterizations revealed that YTHDF2 affects cytoplasmic localization and mediates the decay of methylated mRNA, YTHDF1 promotes translation of methylated mRNA through facilitating translation initiation, and YTHDC1 affects the nuclear export of methylated mRNA. At the organismal level, knockout of Ythdc1 or Ythdf2 is embryonically lethal in mouse.

Applicants have shown that $m^6A$ methylation can significantly affect the mRNA and lncRNA structure transcriptome-wide. The $m^6A$ effect on mRNA/lncRNA structure, termed "$m^6A$-switch," can dramatically affect protein-RNA interactions to impact mRNA abundance and alternative splicing of the methylated RNA. Therefore, $m^6A$ exerts its functions not only through being directly "read," but also through RNA structural remodeling.

Using an antibody known to recognize $m^6A$ to enrich $m^6A$-containing RNA fragments, transcriptome-wide profiling has been performed in human cells and mouse tissues. Both studies revealed tens of thousands of $m^6A$-containing segments in mRNA and lncRNA. The $m^6A$-immunoprecipitation (IP) approach uncovers "$m^6A$-peaks" that are on average 100-200 bases wide in the mRNA/lncRNA. Subsequent SCARLET studies by Applicants at a dozen $m^6A$ sites at single-base resolution revealed sub-stoichiometry at all modification sites in mRNA/lncRNA investigated. Transcriptome-wide profiling of $m^6A$ during yeast meiosis and sporulation has also uncovered profound mRNA methylation, suggesting functional roles.

Figure 3:
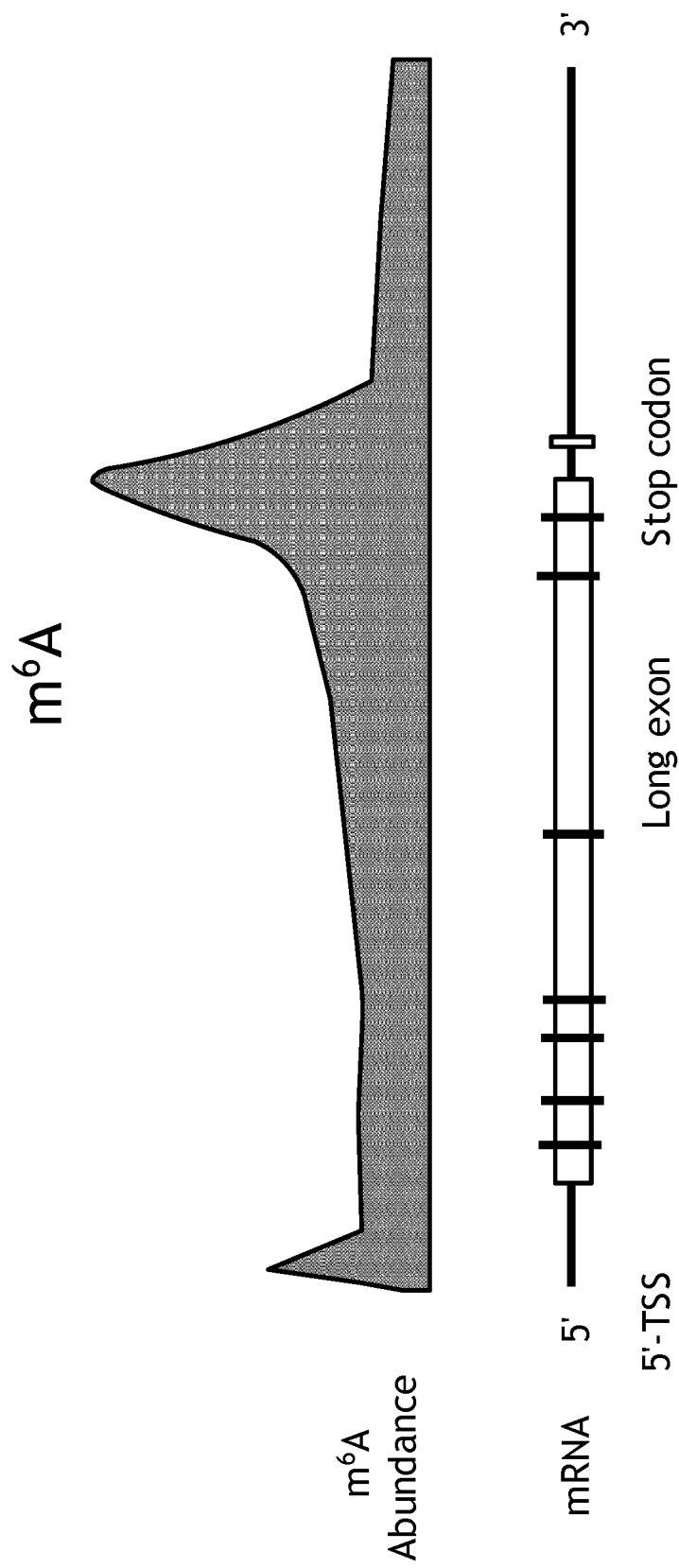
FIG. 3. The general distribution of $m^6A$ in mammalian mRNA.

These global mapping studies have unveiled conserved, widespread, and dynamic mRNA methylation in eukaryotes. Three salient features of the $m^6A$ methylome are conserved in mammals: i) $m^6A$ sites are mainly confined in the consensus motif $Pu[G>A]m^6AC[U>A>C]$, consistent with early studies. The overall cellular $m^6A$ methylation accounts for at most ~15% of all consensus sequences that can be modified; ii) $m^6A$ marks are not equally distributed across the transcriptome; rather, they are preferentially enriched in a subset of consensus sequences near stop codons, in 3' UTRs, and within long internal exons (FIG. 3). This topology is preserved upon endodermal differentiation of stem cells; iii), $m^6A$-modified genes are well conserved between human and mouse embryonic stem cells (ESCs) and somatic cells. For instance, ~70% of human ESC genes are also $m^6A$ modified in the orthologous mouse gene with ~46% of $m^6A$ peak sites in common. As expected, higher $m^6A$ peak intensities were detected in conserved sites compared to those that are not conserved. On the other hand, distinct $m^6A$ patterns can also be detected among different species or cells in different developmental stages. As expected, certain $m^6A$ modifications are tissue-specific and dynamically altered in response to different stimuli, again indicating potential functional roles of $m^6A$ in regulating diverse cellular processes.

Applicants have performed $m^6A$ profiling in mRNA from three individuals in each of human, chimpanzee, and rhesus monkey. Results indicate that the newly evolved $m^6A$-modified transcripts are noticeably enriched in human disease pathways. In addition, results also indicate the functional significances of $m^6A$ in mRNA in neurogenesis and neurodevelopment.

B. $N^1$-methyladenosine ($m^1A$)

The most abundant eukaryotic rRNA and tRNA modifications are pseudouridine $\Omega$, 2'O-methyls (Nm), $N^1$-methyladenosine ($m^1A$), and 5-methylcytidine ($m^5C$). These are installed either through the use of guide RNAs bound with protein factors (snoRNP) or through designated protein enzymes. SnoRNA deletion and mutations in snoRNP proteins or rRNA/tRNA modification enzymes have been associated with human diseases including neurodegeneration, diabetes, and cancer. It is unclear in many cases, however, whether these disease phenotypes are truly derived from defects in rRNA/tRNA modifications or other yet-to-be-discovered mechanisms.

Figure 4:
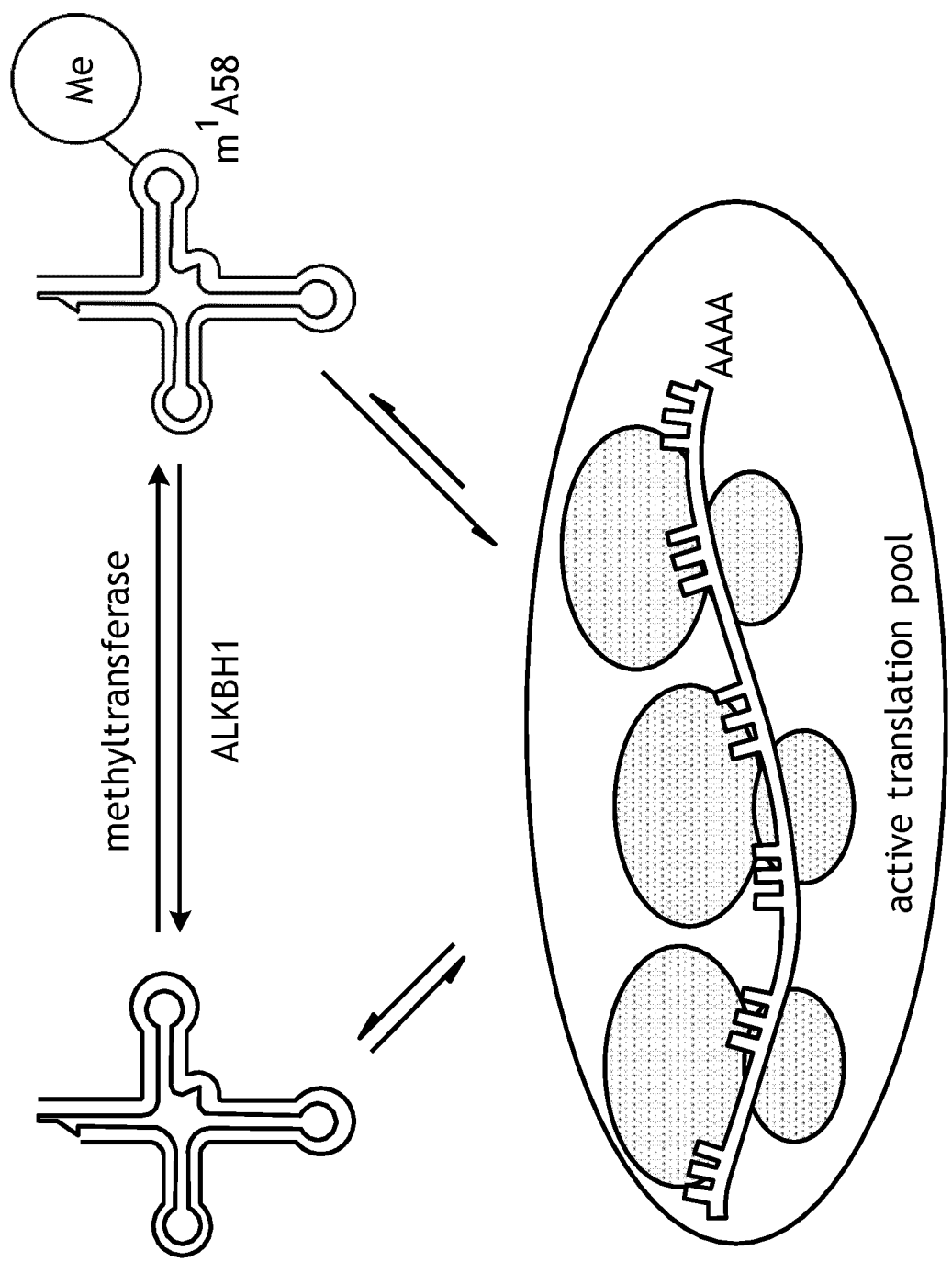
FIG. 4. The reversible $m^1A58$ tRNA methylation controls tRNA utility in translation.

$m^1A$ not only blocks Watson-Crick base pairing but also introduces an extra positive charge under physiological conditions (FIG. 1). It can introduce structural changes and dramatically impact protein-RNA interactions due to the presence of the methyl group and the positive charge. Most eukaryotic tRNA species contain $N^1$-methylation at position 58 ($m^1A58$). $m^1A58$ is essential for the stability of initiator $tRNA^{1Met}$; its absence leads to the decay of $tRNA^{1Met}$, resulting in impaired cell viability. Other mammalian tRNAs such as $tRNA^{Gly}$, $tRNA^{His}$, $tRNA^{val}$, and $tRNA^{Phe}$ also possess $m^1A58$ while many mitochondria tRNA species contain $m^1A9$ methylation. A recent new discovery by Applicants found a new mammalian RNA demethylase that specifically reverses several tRNA $m^1A$ methylation (FIG. 4). This enzyme-mediated demethylation affects the association of target tRNAs with polysomes and the use of tRNAs in translation. Increased $m^1A$ methylation on the target tRNA results in increased partition of the tRNA in polysomes, leading to augmented protein synthesis. Applicants have therefore uncovered that, in addition to $m^6A$ in mRNA/lncRNA, reversible methylation also acts on $m^1A$ in tRNA and likely mRNA/lncRNA to regulate gene expression. Applicants have indeed discovered relatively abundant $m^1A$ in mammalian mRNA with a unique distribution pattern indicating functional roles.

C. Other Adenosine Modifications

The methods and compositions of the disclosure are useful in the detection of adenosine modifications. It is contemplated that the methods and compositions may be useful for detecting the adenosine modifications listed below.

| Symbol | Common Name |
|---|---|
| $m^1A$ | 1-methyladenosine |
| $m^2A$ | 2-methyladenosine |
| $m^6A$ | $N^6$-methyladenosine |
| Am | 2'-O-methyladenosine |
| $ms^2m^6A$ | 2-methylthio-$N^6$-methyladenosine |
| $i^6A$ | $N^6$-isopentenyladenosine |
| $ms^2i^6A$ | 2-methylthio-$N^6$-isopentenyladenosine |
| $io^6A$ | $N^6$-(cis-hydroxyisopentenyl)adenosine |
| $ms^2io^6A$ | 2-methylthio-$N^6$-(cis-hydroxyisopentenyl) adenosine |
| $g^6A$ | $N^6$-glycinylcarbamoyladenosine |
| $t^6A$ | $N^6$-threonylcarbamoyladenosine |
| $ms^2t^6A$ | 2-methylthio-$N^6$-threonyl carbamoyladenosine |
| $m^6t^6A$ | $N^6$-methyl-$N^6$-threonylcarbamoyladenosine |
| $hn^6A$ | $N^6$-hydroxynorvalylcarbamoyladenosine |
| $ms^2hn^6A$ | 2-methylthio-$N^6$-hydroxynorvalyl carbamoyladenosine |
| Ar(p) | 2'-O-ribosyladenosine (phosphate) |
| $m^6_2A$ | $N^6,N^6$-dimethyladenosine |
| $m^6Am$ | $N^6$,2'-O-dimethyladenosine |
| $m^6_2Am$ | $N^6,N^6$,2'-O-trimethyladenosine |
| $m^1Am$ | 1,2'-O-dimethyladenosine |
| $ac^6A$ | $N^6$-acetyladenosine |
| $m^8A$ | 8-methyladenosine |

To summarize, mammalian mRNA and lncRNA contain many internal modifications with abundances ranging from 0.2-3 modified nucleotides per mRNA. This range of abundance suggests the presence of hundreds to tens of thousands of modified sites for each modification type in mammalian transcriptomes. Further, $m^6A$ and $m^1A$ are known to be reversible and undergo dynamic regulation. $m^6A$ is the most abundant and has been best studied with broad and fundamental roles uncovered so far. Other modifications could provide additional tuning of mRNA metabolism and function. The lack of highly sensitive, selective, and robust sequencing approaches for all these modifications presents current technology barriers that significantly hinder biological investigations. Development of single-base resolution and highly sensitive methods will be required in order to move the field forward and also to enable new discoveries on the functions of RNA modifications and their associations with human diseases.

II. Enzyme-Catalyzed Deamination

Figure 5B:
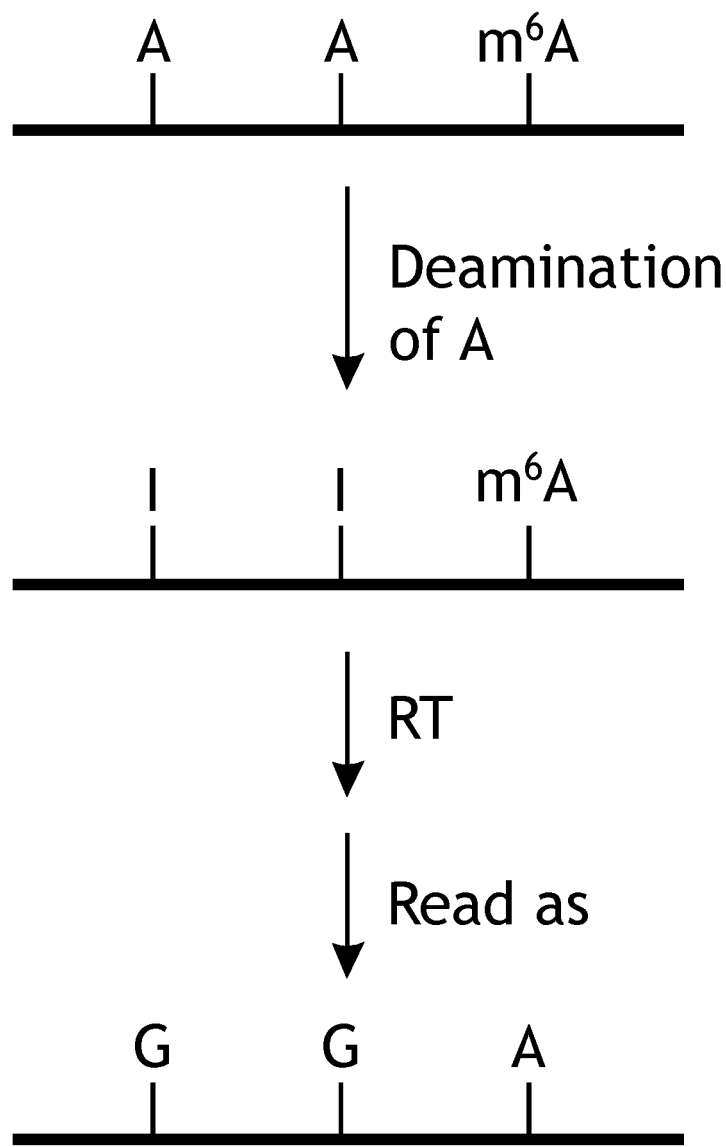

The current disclosure provides methods and compositions comprising enzyme-mediated deamination for base-resolution sequencing of modified adenosines (e.g. $m^6A$) in RNA. The current disclosure is based on a method that converts only unmodified A in RNA into a different base, leaving modified A untouched, and thereby allowing differentiation of A from $m^6A$ in sequencing (FIG. 5B).

A. ADAR (adenosine deaminase, RNA-Specific)

As detailed in the Examples of the application, RNA editing ADAR enzymes that deaminate A to inosine (I) in mRNA using guide RNAs that form duplexes with all target sites can be used. The ADAR enzyme is highly active against A but possesses over 50-fold lower activity towards $m^6A$ compared to unmodified A. Therefore, after selective deamination of all A in the transcriptome and subsequent RT-PCR followed by sequencing, only $m^6A$ will be read as A (FIG. 5B).

The ADAR from *Drosophila melanogaster* (also known as Dmel_CG12598, ADAR, ADAR1, CG12598, Dmel\CG12598, EG:BACN35H14.1, adar, adr, cg12598, dADAR, dAdar, and hypnos-2) is represented by the following GenBank accession Nos:

| DNA | Protein | ADAR |
|---|---|---|
| NM_001258548.2 | NP_001245477.1 | adenosine deaminase acting on RNA, isoform F [*Drosophila melanogaster*] |
| NM_001297862.1 | NP_001284791.1 | adenosine deaminase acting on RNA, isoform N [*Drosophila melanogaster*] |
| NM_166903.3 | NP_726761.2 | adenosine deaminase acting on RNA, isoform B [*Drosophila melanogaster*] |
| NM_001258547.2 | NP_001245476.1 | adenosine deaminase acting on RNA, isoform E [*Drosophila melanogaster*] |
| NM_001038732.3 | NP_001033821.1 | adenosine deaminase acting on RNA, isoform C [*Drosophila melanogaster*] |
| NM_130584.4 | NP_569940.2 | adenosine deaminase acting on RNA, isoform A [*Drosophila melanogaster*] |
| NM_001258545.2 | NP_001245474.1 | adenosine deaminase acting on RNA, isoform H [*Drosophila melanogaster*] |
| NM_001258546.2 | NP_001245475.1 | adenosine deaminase acting on RNA, isoform D [*Drosophila melanogaster*] |
| NM_001258542.2 | NP_001245471.1 | adenosine deaminase acting on RNA, isoform K [*Drosophila melanogaster*] |
| NM_001258544.2 | NP_001245473.1 | adenosine deaminase acting on RNA, isoform M [*Drosophila melanogaster*] |
| NM_001258543.2 | NP_001245472.2 | adenosine deaminase acting on RNA, isoform O [*Drosophila melanogaster*] |
| NM_001297863.1 | NP_001284792.1 | adenosine deaminase acting on RNA, isoform P [*Drosophila melanogaster*] |
| NM_001258541.2 | NP_001245470.1 | adenosine deaminase acting on RNA, isoform J [*Drosophila melanogaster*] |
| NM_001258540.1 | NP_001245469.1 | adenosine deaminase acting on RNA, isoform I [*Drosophila melanogaster*] |

The sequences associated with each of the GenBank Accession numbers is herein incorporated by reference for all purposes. In some embodiments, the ADAR has the sequence associated with NP_001284791.1:

```
                                            (SEQ ID NO: 1)
mlnsannnsp qhpvsapsdi nmngynrklp qkrgyempky sdpkkkmcke ripqpkntva mlnelrhgli yklesqtgpv haplftisve vdgqkylgqg rskkvariea aatalrsfiq fkdgavlspl kpagnldfts dehlengien lssskmfeii qtmlteklsn ptsleqptfc msqnvsksai tvdgqkkvpd kgpvmllyel fndvnfecin idgaqnncrf kmtvtinekk fdgtgpskkt aknaaakaal aslcnisysp mvvpqknvpl piddksssme lpqihadtig rlvlekfmev ikgqeaysrr kvlagivmte nmnfceakvi systgtkcvs gehmsvngav lndshaeivs rrcllkylya qldlqcnqat ayqsifvrnt dggypyklks gvhfhlyint apcgdarifs phendtgvdk hpnrkargql rtkiesgegt ipvkssdgiq twdgvlqgqr lltmscsdki arwnivgiqq sllssiiepv ylhsivlgsl lhpehmyrav cgrieksiqg lpppyhlnkp rlalvtsaep rnqakapnfg inwtigdtel evvnsltgrt iggqvsritk qaffvkygfl manlpgilvr kvttdygqtk anvkdyqiak lelfsafkre dlgswlkkpi eqdefglae.
```

B. Protein Preparation

A variety of proteins can be purified using methods known in the art. Protein purification is a series of processes intended to isolate a single type of protein from a complex mixture. Protein purification is vital for the characterization of the function, structure and interactions of the protein of interest. The starting material is usually a biological tissue or a microbial culture. The various steps in the purification process may free the protein from a matrix that confines it, separate the protein and non-protein parts of the mixture, and finally separate the desired protein from all other proteins. Separation of one protein from all others is typically the most laborious aspect of protein purification. Separation steps exploit differences in protein size, physico-chemical properties and binding affinity.

Evaluating purification yield. The most general method to monitor the purification process is by running a SDS-PAGE of the different steps. This method only gives a rough measure of the amounts of different proteins in the mixture, and it is not able to distinguish between proteins with similar molecular weight. If the protein has a distinguishing spectroscopic feature or an enzymatic activity, this property can be used to detect and quantify the specific protein, and thus to select the fractions of the separation, that contains the protein. If antibodies against the protein are available then western blotting and ELISA can specifically detect and quantify the amount of desired protein. Some proteins function as receptors and can be detected during purification steps by a ligand binding assay, often using a radioactive ligand.

In order to evaluate the process of multistep purification, the amount of the specific protein has to be compared to the amount of total protein. The latter can be determined by the Bradford total protein assay or by absorbance of light at 280 nm, however some reagents used during the purification process may interfere with the quantification. For example, imidazole (commonly used for purification of polyhistidine-tagged recombinant proteins) is an amino acid analogue and at low concentrations will interfere with the bicinchoninic acid (BCA) assay for total protein quantification. Impurities in low-grade imidazole will also absorb at 280 nm, resulting in an inaccurate reading of protein concentration from UV absorbance.

Another method to be considered is Surface Plasmon Resonance (SPR). SPR can detect binding of label free molecules on the surface of a chip. If the desired protein is an antibody, binding can be translated to directly to the activity of the protein. One can express the active concentration of the protein as the percent of the total protein. SPR can be a powerful method for quickly determining protein activity and overall yield. It is a powerful technology that requires an instrument to perform.

Methods of protein purification. The methods used in protein purification can roughly be divided into analytical and preparative methods. The distinction is not exact, but the deciding factor is the amount of protein that can practically be purified with that method. Analytical methods aim to detect and identify a protein in a mixture, whereas preparative methods aim to produce large quantities of the protein for other purposes, such as structural biology or industrial use.

Depending on the source, the protein has to be brought into solution by breaking the tissue or cells containing it. There are several methods to achieve this: Repeated freezing and thawing, sonication, homogenization by high pressure, filtration (either via cellulose-based depth filters or cross-flow filtration), or permeabilization by organic solvents. The method of choice depends on how fragile the protein is and how sturdy the cells are. After this extraction process soluble proteins will be in the solvent, and can be separated from cell membranes, DNA etc. by centrifugation. The extraction process also extracts proteases, which will start digesting the proteins in the solution. If the protein is sensitive to proteolysis, it is usually desirable to proceed quickly, and keep the extract cooled, to slow down proteolysis.

In bulk protein purification, a common first step to isolate proteins is precipitation with ammonium sulfate $(NH_4)_2SO_4$. This is performed by adding increasing amounts of ammonium sulfate and collecting the different fractions of precipitate protein. One advantage of this method is that it can be performed inexpensively with very large volumes.

The first proteins to be purified are water-soluble proteins. Purification of integral membrane proteins requires disruption of the cell membrane in order to isolate any one particular protein from others that are in the same membrane compartment. Sometimes a particular membrane fraction can be isolated first, such as isolating mitochondria from cells before purifying a protein located in a mitochondrial membrane. A detergent such as sodium dodecyl sulfate (SDS) can be used to dissolve cell membranes and keep membrane proteins in solution during purification; however, because SDS causes denaturation, milder detergents such as Triton™ X-100 or CHAPS can be used to retain the protein's native conformation during complete purification.

Centrifugation is a process that uses centrifugal force to separate mixtures of particles of varying masses or densities suspended in a liquid. When a vessel (typically a tube or bottle) containing a mixture of proteins or other particulate matter, such as bacterial cells, is rotated at high speeds, the angular momentum yields an outward force to each particle that is proportional to its mass. The tendency of a given particle to move through the liquid because of this force is offset by the resistance the liquid exerts on the particle. The net effect of "spinning" the sample in a centrifuge is that massive, small, and dense particles move outward faster than less massive particles or particles with more "drag" in the liquid. When suspensions of particles are "spun" in a centrifuge, a "pellet" may form at the bottom of the vessel that is enriched for the most massive particles with low drag in the liquid. Non-compacted particles still remaining mostly in the liquid are called the "supernatant" and can be removed from the vessel to separate the supernatant from the pellet. The rate of centrifugation is specified by the angular acceleration applied to the sample, typically measured in comparison to the g. If samples are centrifuged long enough, the particles in the vessel will reach equilibrium wherein the particles accumulate specifically at a point in the vessel where their buoyant density is balanced with centrifugal force. Such an "equilibrium" centrifugation can allow extensive purification of a given particle.

Sucrose gradient centrifugation is a linear concentration gradient of sugar (typically sucrose, glycerol, or a silica based density gradient media, like Percoll™) is generated in a tube such that the highest concentration is on the bottom and lowest on top. A protein sample is then layered on top of the gradient and spun at high speeds in an ultracentrifuge. This causes heavy macromolecules to migrate towards the bottom of the tube faster than lighter material. After separating the protein/particles, the gradient is then fractionated and collected.

Usually a protein purification protocol contains one or more chromatographic steps. The basic procedure in chromatography is to flow the solution containing the protein through a column packed with various materials. Different proteins interact differently with the column material, and can thus be separated by the time required to pass the column, or the conditions required to elute the protein from the column. Usually proteins are detected as they are coming off the column by their absorbance at 280 nm. Many different chromatographic methods exist:

Chromatography can be used to separate protein in solution or denaturing conditions by using porous gels. This technique is known as size exclusion chromatography. The principle is that smaller molecules have to traverse a larger volume in a porous matrix. Consequentially, proteins of a certain range in size will require a variable volume of eluent (solvent) before being collected at the other end of the column of gel.

In the context of protein purification, the eluant is usually pooled in different test tubes. All test tubes containing no measurable trace of the protein to purify are discarded. The remaining solution is thus made of the protein to purify and any other similarly-sized proteins.

Ion exchange chromatography separates compounds according to the nature and degree of their ionic charge. The column to be used is selected according to its type and strength of charge. Anion exchange resins have a positive charge and are used to retain and separate negatively charged compounds, while cation exchange resins have a negative charge and are used to separate positively charged molecules. Before the separation begins a buffer is pumped through the column to equilibrate the opposing charged ions. Upon injection of the sample, solute molecules will exchange with the buffer ions as each competes for the binding sites on the resin. The length of retention for each solute depends upon the strength of its charge. The most weakly charged compounds will elute first, followed by those with successively stronger charges. Because of the nature of the separating mechanism, pH, buffer type, buffer concentration, and temperature all play important roles in controlling the separation.

Affinity Chromatography is a separation technique based upon molecular conformation, which frequently utilizes application specific resins. These resins have ligands attached to their surfaces which are specific for the compounds to be separated. Most frequently, these ligands function in a fashion similar to that of antibody-antigen interactions. This "lock and key" fit between the ligand and its target compound makes it highly specific, frequently generating a single peak, while all else in the sample is unretained.

Many membrane proteins are glycoproteins and can be purified by lectin affinity chromatography. Detergent-solubilized proteins can be allowed to bind to a chromatography resin that has been modified to have a covalently attached lectin. Proteins that do not bind to the lectin are washed away and then specifically bound glycoproteins can be eluted by adding a high concentration of a sugar that competes with the bound glycoproteins at the lectin binding site. Some lectins have high affinity binding to oligosaccharides of glycoproteins that is hard to compete with sugars, and bound glycoproteins need to be released by denaturing the lectin.

A common technique involves engineering a sequence of 6 to 8 histidines into the N- or C-terminal of the protein. The polyhistidine binds strongly to divalent metal ions such as nickel and cobalt. The protein can be passed through a column containing immobilized nickel ions, which binds the polyhistidine tag. All untagged proteins pass through the column. The protein can be eluted with imidazole, which competes with the polyhistidine tag for binding to the column, or by a decrease in pH (typically to 4.5), which decreases the affinity of the tag for the resin. While this procedure is generally used for the purification of recombinant proteins with an engineered affinity tag (such as a 6×His tag or Clontech's HAT tag), it can also be used for natural proteins with an inherent affinity for divalent cations.

Immunoaffinity chromatography uses the specific binding of an antibody to the target protein to selectively purify the protein. The procedure involves immobilizing an antibody to a column material, which then selectively binds the protein, while everything else flows through. The protein can be eluted by changing the pH or the salinity. Because this method does not involve engineering in a tag, it can be used for proteins from natural sources.

Another way to tag proteins is to engineer an antigen peptide tag onto the protein, and then purify the protein on a column or by incubating with a loose resin that is coated with an immobilized antibody. This particular procedure is known as immunoprecipitation. Immunoprecipitation is quite capable of generating an extremely specific interaction which usually results in binding only the desired protein. The purified tagged proteins can then easily be separated from the other proteins in solution and later eluted back into clean solution. Tags can be cleaved by use of a protease. This often involves engineering a protease cleavage site between the tag and the protein.

High performance liquid chromatography or high pressure liquid chromatography is a form of chromatography applying high pressure to drive the solutes through the column faster. This means that the diffusion is limited and the resolution is improved. The most common form is "reversed phase" hplc, where the column material is hydrophobic. The proteins are eluted by a gradient of increasing amounts of an organic solvent, such as acetonitrile. The proteins elute according to their hydrophobicity. After purification by HPLC the protein is in a solution that only contains volatile compounds, and can easily be lyophilized.

HPLC purification frequently results in denaturation of the purified proteins and is thus not applicable to proteins that do not spontaneously refold.

At the end of a protein purification, the protein often has to be concentrated. Different methods exist. If the solution doesn't contain any other soluble component than the protein in question the protein can be lyophilized (dried). This is commonly done after an HPLC run. This simply removes all volatile component leaving the proteins behind.

Ultrafiltration concentrates a protein solution using selective permeable membranes. The function of the membrane is to let the water and small molecules pass through while retaining the protein. The solution is forced against the membrane by mechanical pump or gas pressure or centrifugation.

Gel electrophoresis is a common laboratory technique that can be used both as preparative and analytical method. The principle of electrophoresis relies on the movement of a charged ion in an electric field. In practice, the proteins are denatured in a solution containing a detergent (SDS). In these conditions, the proteins are unfolded and coated with negatively charged detergent molecules. The proteins in SDS-PAGE are separated on the sole basis of their size.

In analytical methods, the protein migrate as bands based on size. Each band can be detected using stains such as Coomassie blue dye or silver stain. Preparative methods to purify large amounts of protein, require the extraction of the protein from the electrophoretic gel. This extraction may involve excision of the gel containing a band, or eluting the band directly off the gel as it runs off the end of the gel.

In the context of a purification strategy, denaturing condition electrophoresis provides an improved resolution over size exclusion chromatography, but does not scale to large quantity of proteins in a sample as well as the late chromatography columns.

Methods of the disclosure may involve purification of proteins by any combination of methods known in the art and/or discussed herein. In some embodiments, the protein is purified by a combination of one or more of affinity chromatography, ion exchange chromatograph, and gel filtration chromatography. In some embodiments, the affinity chromatography is anti-FLAG. In some embodiments, the ion exchange chromatography is heparin.

III. Assays Utilizing Adenosine Modification

Nucleic acid analysis and evaluation includes various methods of amplifying, fragmenting, and/or hybridizing nucleic acids that have or have not been modified.

Methodologies are available for large scale sequence analysis. In certain aspects, the methods described exploit these genomic analysis methodologies and adapt them for uses incorporating the methodologies described herein. In certain instances the methods can be used to perform high resolution adenosine modification analysis on modified adenosines in RNA. Therefore, methods are directed to analysis of the adenosine modification status of a RNA sample, comprising one or more of the steps: (a) contacting the target RNA with an adenosine deaminase enzyme to generate a target RNA with deaminated adenosines, (b) sequencing the target RNA with deaminated adenosines; wherein the modified adenosine is detected when the nucleotide sequence is adenosine. In some embodiments, the method further comprises steps such as sequencing a control RNA; comparing the sequence of the target RNA with deaminated adenosines to the sequence of the control RNA; generating a nucleic acid strand that is complementary with the target and/or control RNA and hybridizing the complementary nucleic acid strand with the target RNA; comparing the known sequence of the target RNA with the sequence of the target RNA with deaminated adenosines.

In some embodiments, the assay comprises a cycle of steps as demonstrated in FIG. 9B. For example, the assay may involve a reverse transcriptase reaction with the target RNA to create a complementary DNA strand. The RNA and complementary DNA strand are then annealed together to create RNA-DNA duplexes. Next, the RNA-DNA duplex is contacted with a deaminating enzyme with specificity for unmodified adenosines and no or greatly reduced, such as 10, 15, 20, 25, 30, 40, 50, 100, or 200 fold less activity (compared to unmodified), for modified adenosines. Furthermore, the ADAR only deaminates RNA. Therefore, the RNA unmodified adenosines are converted to inosines in the target RNA strand. The DNA can then be digested using a DNA digesting enzyme, leaving the RNA intact. The RNA can then be purified and another round of reverse transcriptase can be performed, creating a new complementary DNA strand. The new complementary DNA strand is different from the first complementary DNA strand, since cytosines are generated as the complement to the inosine. In contrast, uracils were generated as the complement to the adenosine in the first complementary strand. The deamination reaction is repeated so that unmodified adenosines that did not get deaminated in the previous round could then be deaminated and converted to inosine on a subsequent round. This may be repeated until a high percentage such as at least 75, 80, 85, 90, 95, 96, 97, 98, 99, or 100% of unmodified adenosines are deaminated and converted to inosine.

A. RNA Isolation

RNA may be isolated from an organism of interest, including, but not limited to eukaryotic organisms and prokaryotic organisms, preferably mammalian organisms, such as humans. RNA may be isolated from cells grown in vitro or from cells in vivo. RNA may be isolated from tissues such as bone, blood, liver, heart, etc . . . . Furthermore, the RNA may be isolated and fractionated by techniquest that separate different RNA types. Therefore, in some embodiments, RNA is purified, and the purified RNA comprises at least 80, 85, 90, 95, 96, 97, 98, 99, or 100% of a particular RNA such as mRNA, lncRNA, non-coding RNA, microRNA, pri-microRNA, pre-piRNA, rRNA, tRNA, snoRNA, or snRNA.

B. Sequencing

The sequencing may be done by known methods of sequencing nucleic acids. In certain embodiments, the target nucleic acids molecules are sequenced using any suitable sequencing technique known in the art. In one example, the sequencing is single-molecule sequencing-by-synthesis. Single-molecule sequencing is shown for example in U.S. Pat. Nos. 7,169,560, 6,818,395, 7,282,337, the contents of each of these references is incorporated by reference herein in its entirety. Other examples of sequencing nucleic acids may include Maxam-Gilbert techniques, Sanger type techniques, Sequencing by Synthesis methods (SBS), Sequencing by Hybridization (SBH), Sequencing by Ligation (SBL), Sequencing by Incorporation (SBI) techniques, massively parallel signature sequencing (MPSS), polony sequencing techniques, nanopore, waveguide and other single molecule detection techniques, reversible terminator techniques, or other sequencing technique now know or may be developed in the future.

In one embodiment, the sequencing is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

In another embodiment, Ion Torrent sequencing can be used. (See, e.g., U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety.) Oligonucleotide adaptors are ligated to the ends of target nucleic acid molecules. The adaptors serve as primers for amplification and sequencing of the fragments. The fragments can be attached to a surface and is attached at a resolution such that the fragments are individually resolvable. Addition of one or more nucleotides releases a proton (H+), which signal detected and recorded in a sequencing instrument. The signal strength is proportional to the number of nucleotides incorporated.

In some embodiments, sequencing the target RNA comprises creating a complementary DNA (cDNA) from the target RNA. In some embodiments, sequencing the target RNA comprises reverse transcription. In some embodiments, sequencing the target RNA comprises contacting the target RNA with an enzyme capable of transcribing DNA using the target RNA as a template (e.g. reverse transcriptase). In some embodiments, a cDNA of the target RNA is sequenced. The sequence of the cDNA is determined, and the cDNA sequence is used to determine the sequence of the target RNA. In some embodiments, the target RNA is determined to have a modified adenosine at the corresponding position of the cDNA that is determined by sequencing to be thymine.

In some embodiments, sequencing the target RNA comprises amplification of nucleic acids. Amplification can be done by techniques known in the art, such as PCR, that uses primers, polymerase, deoxynucleoside triphosphates, buffers, and bivalent and monovalent cations in a reaction that generates copies of a target DNA sequence from a single or few copies of the target DNA sequence.

C. Controls

In some embodiments, the methods described herein further comprise control samples. The intrinsically present RNA editing product should not influence the in vitro deamination (A has already been converted to I). However, an accurate assignment of the methylation fraction at each modification site could be affected if the same site is also intrinsically deaminated to some extent. In addition, the ADAR enzyme may exhibit certain sequence and/or structure biases that need to be corrected. Therefore, a control sample with minimum methylation is required to correct these factors.

Figure 8A:
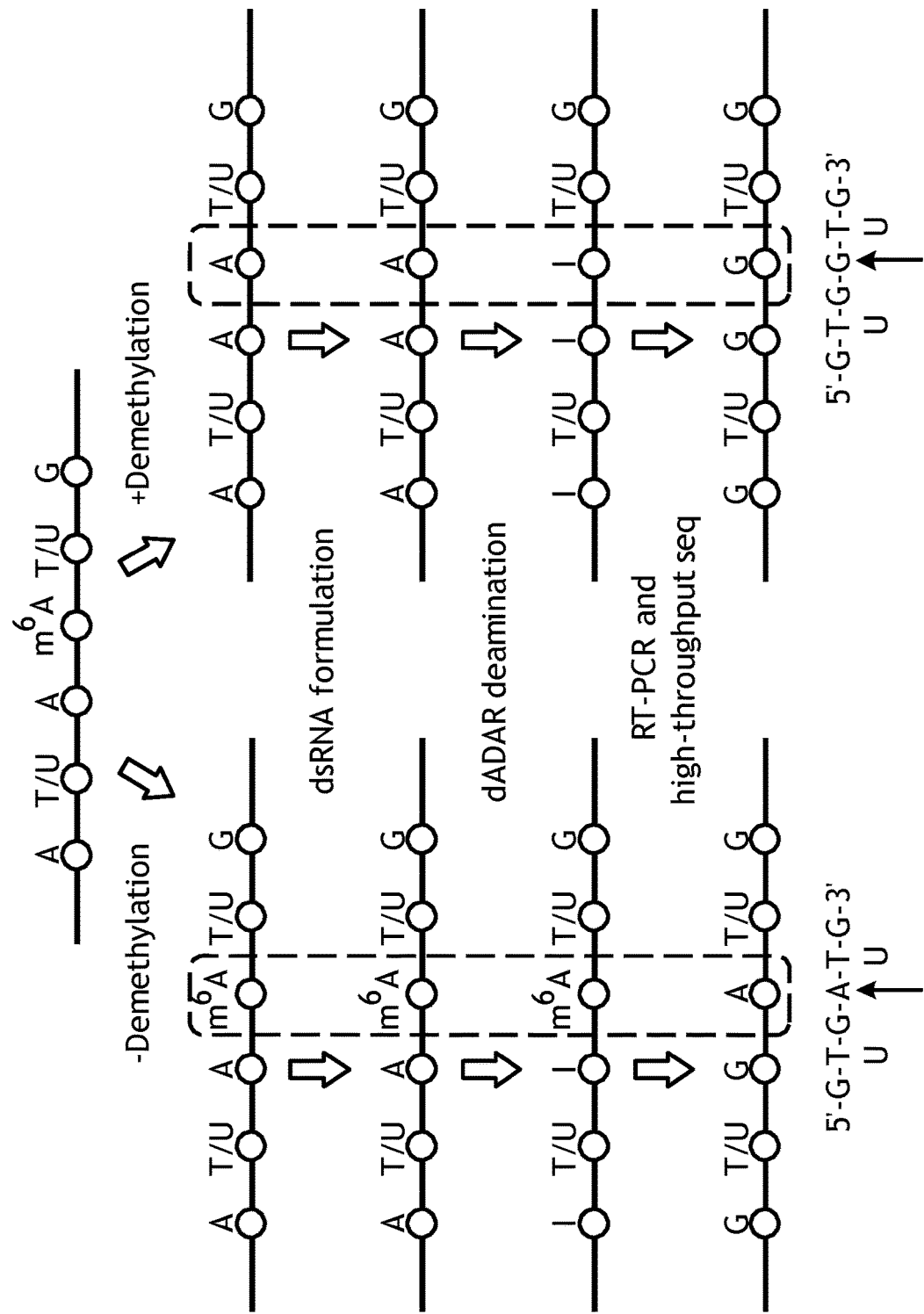
FIGS. 8A-C. A strategy to couple Deam-$m^6A$-seq with ALKBH5-mediated demethylation for accurate $m^6A$ assignments. (A) The isolated mRNA is split into two portions, one treated with ALKBH5, the other untreated. Both groups are then supplied with anti-sense RNA strand to form dsRNA, which is the natural substrate of the dADAR-mediated deamination reaction. The product is subjected to RT-PCR and high-throughput sequencing. The A-to-G transitions observed in the demethylated sample represent methylation sites in RNA. The +demethylation process exemplifies the production of the control RNA by demethylation of a pool of target RNA. (B) ALKBH5 catalyzes the demethylation of close to 90% of all $m^6A$ in isolated mammalian polyA-tailed RNA revealed by LS-MS/MS. (SEQ ID NOs. 2 and 3) (C) The tandem demethylation followed by the deamination procedure was applied to a dsRNA substrate with 1:1 mixture of A:$m^6A$ at every adenosine position in the target strand. The A-to-G transition ratios of the target strand revealed significant deamination differences before and after the demethylation treatment.
Figure 8B:
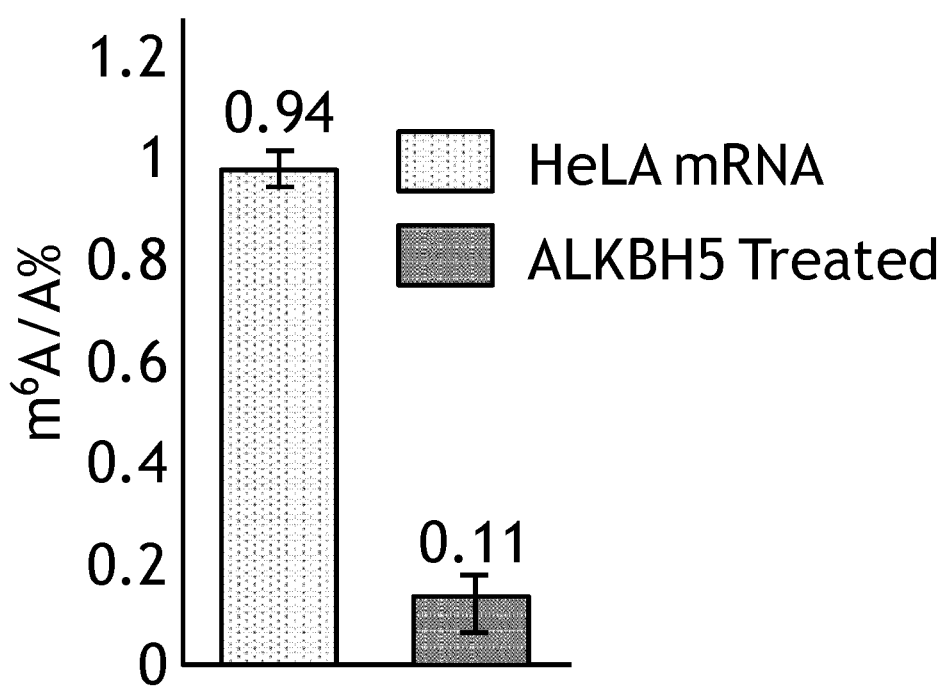

In one embodiment, the control sample is a control transcript with minimum adenosine modification. In one embodiment, the control sample is a control transcript minimum $m^6A$ methylation (FIG. 8A). Cellular mRNA can be isolated and subjected to a demethylase that is specific for the adenosine modification. For example, the $m^6A$ modification can be demethylated by way of ALKBH5-catalyzed $m^6A$ demethylation. ALKBH5 is one of the two known $m^6A$ RNA demethylases. Recombinant ALKBH5 is highly active and can remove most $m^6A$ (90%) from mammalian mRNA in vitro as shown in FIG. 8B.

In some embodiments the method comprises a control sample. To construct a control sample, the RNA preparation comprising the target RNA may be separated into multiple, such as at least, at most, or exactly 2, 3, 4, 5, 6, or more portions (or any derivable range therein). One portion may be subjected to modification-specific demethylation to remove the modification on the RNA. In some embodiment, one portion is contacted with ALKBH5 to catalyze $m^6A$ demethylation to remove most $m^6A$ on RNA. Next, both portions of the mRNA samples (after forming duplex RNA) will be subjected to the enzyme-mediated deamination, RT-PCR amplification, and high-throughput sequencing. Because the modified adenosine is resistant to deamination it will be read as A in the sample without modification-specific demethylation (e.g. ALKBH5 treatment). In the demethylation (e.g. ALKBH5-treated) control $m^6A$ is converted to A, which is deaminated to inosine in the deamination step and will be read as G. A comparison of the two parallel sequencing data will accurately reveal specific modification sites (i.e. $m^6A$ when ALKBH5 is used as the demethylase) at base resolution and eliminate potential RNA editing at the modification site (unmodified A-to-I) and potential biases of the deamination step.

IV. Kits

The invention additionally provides kits for detecting modified adenosines in a target RNA. Each kit may also include additional components that are useful for amplifying the nucleic acid, or sequencing the nucleic acid, or other applications of the present invention as described herein. The kit may optionally provide additional components that are useful in the procedure. These optional components include buffers, capture reagents, developing reagents, labels, reacting surfaces, means for detection, control samples, instructions, and interpretive information. The kit may also include reagents for RNA isolation and/or purification.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments, are provided as an example, and are not intended as limitations on the scope of the invention. Changes therein and other uses which are encompassed within the spirit of the invention as defined by the scope of the claims will occur to those skilled in the art.

Example 1

Deamination-Based Sequencing to Differentiate Modified Versus Unmodified Adenosines and Cytosines Because the $m^6A$ modification on mRNA/lncRNA plays the most significant and broad roles in gene expression regulation, the focus of this Example is on sequencing of this modification. However, one skilled in the art would readily understand that parallel techniques could be applied for sequencing other adenosine modifications.

ADAR-mediated adenosine deamination sequencing (Deam-m$^6$A-seq)

Figure 6B:
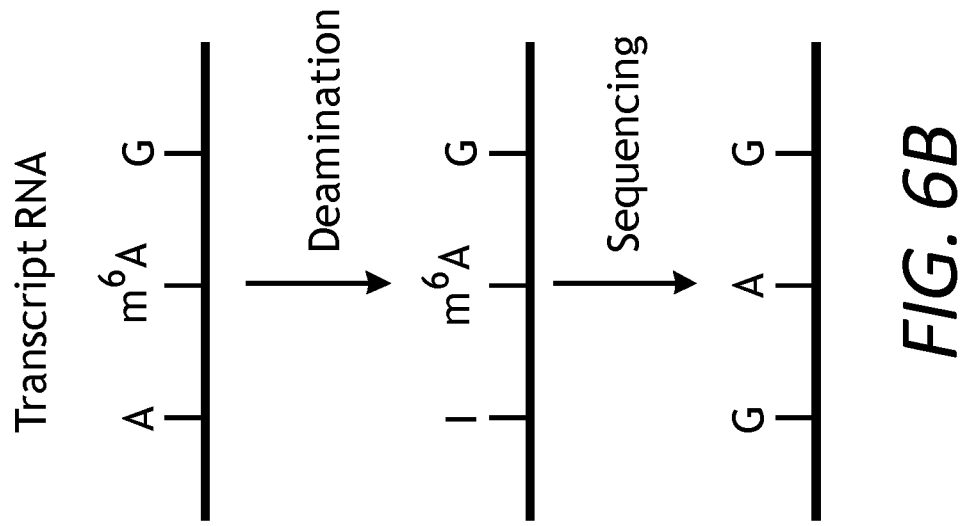
FIGS. 6A-B. The strategy of ADAR-mediated adenosine deamination sequencing (Deam-$m^6A$-seq). (A) The *drosophila* or mammalian RNA adenosine deaminase (ADAR) can effectively convert A to I in duplex RNA; however, its activity towards $m^6A$ in duplex RNA is <2% of that for A. (B) We can employ ADAR to convert A to I while maintaining $m^6A$ as A in Deam-$m^6A$-seq.
Figure 6A:
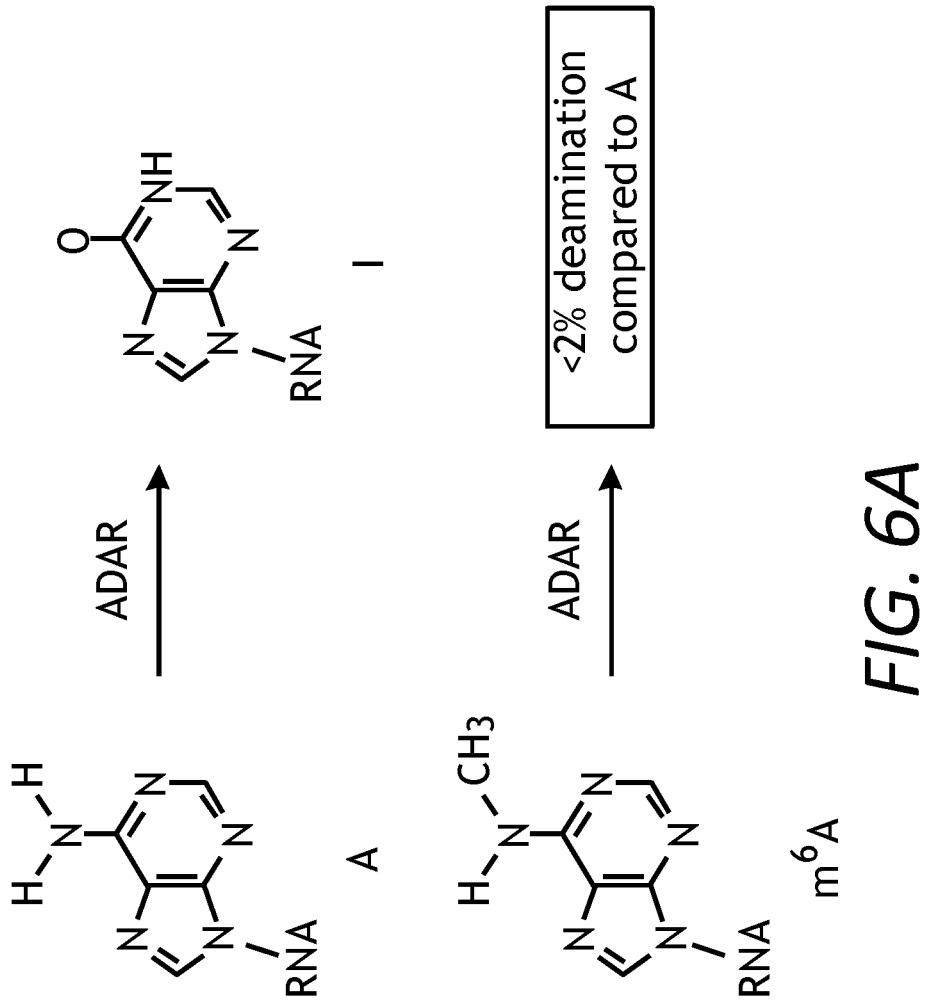

Applicants contemplated that adenosine deamination would be useful in methods for obtaining base-resolution sequencing of m$^6$A in RNA (FIG. 6). Adenosine deamination, leading to adenosine-to-inosine (A-to-I) RNA editing, plays important regulatory roles in post-transcriptional processes including mRNA re-coding and alternative splicing. The RNA adenosine deaminases (ADAR) efficiently catalyze this reaction in duplex RNA. Previous studies have shown that the m$^6$A methylation significantly hinders the deamination activity of ADAR proteins. Less than 2% activity with slower kinetics was observed with m$^6$A as the substrate (FIG. 6A). ADAR can be used to convert all A in isolated RNA to inosines while keeping m$^6$A mostly intact. Subsequent amplification and high-throughput sequencing will read m$^6$A as A while unmodified A is read as G (FIG. 6B). In some embodiments, Drosophila ADAR (dADAR) is used. dADAR exhibits non-specific RNA editing activity on long double-stranded RNA (dsRNA).

The proposed use of ADAR for Deam-m$^6$A-seq of m$^6$A is not straightforward. Several major challenges must be resolved: 1. ADAR only works on duplex RNA. We must generate anti-sense RNA and form duplexes with sense RNA in order for the deamination reaction to occur. 2. ADAR-catalyzed deamination of duplex RNA can hardly reach 30% conversion because the deamination reaction converts A in the duplex RNA to I, which progressively weakens the duplex stability until dissociation of the two RNA strands leading to termination of the reaction. 3. The need for a control to correct various factors that may affect the deamination reaction. The intrinsically present RNA editing product should not influence the in vitro deamination (A has already been converted to I). However, an accurate assignment of the methylation fraction at each modification site could be affected if the same site is also intrinsically deaminated to some extent. In addition, the ADAR enzyme may exhibit certain sequence and/or structure biases that need to be corrected. Therefore, a control sample with minimum methylation is required in order to correct these factors.

Several strategies exist with regard to generating duplex RNA. The third challenge can be addressed with a demodification strategy, also detailed above in the "controls" section. The first and second challenges are most critical to overcome.

Challenge 1, Generating double-stranded RNA: Because ADAR only works on duplex RNA one solution is to generate a transcriptome-wide anti-sense RNA strand pool in order to form dsRNA for the application of Deam-m$^6$A-seq. To do this, one can use cDNA library to prepare anti-sense RNA fragments and then anneal to the transcripts. Well-established procedures to clone mammalian or other cDNA into plasmids can be used. The anti-sense RNAs can be transcribed in vitro using T7 RNA polymerase and are annealed to the methylated and the demethylated transcriptomes; the resulting dsRNAs can serve as the substrates for the dADAR-mediated deamination.

Alternatively, the 3' primer-free Phi6 RNA replicase can be utilized to generate dsRNA using purified transcripts as templates. Phi6 RNA replicase is a primer-independent viral RNA replicase. It can generate dsRNA directly from ssRNA templates without primers. This approach serves as an alternative to produce dsRNA for dADAR-mediated deamination.

Challenge 2, Innefficient deamination: To improve the deamination efficiency of ADAR on the sense strand of dsRNA, Applicants devised a strategy to inhibit adenosine deamination of the anti-sense strand of dsRNA. Applicants employed N$^6$-methyladenosine triphosphate (m$^6$ATP or me-ATP) in the in vitro transcription reaction to generate the complementary strand, replacing all A with m$^6$A on the anti-sense RNA strand in order to prevent the deamination reaction and increase the stability of dsRNA. Applicants cloned recombinant dADAR into an insect cell expression system with a FLAG tag on the N terminus and a polyhistidine tag on the C terminus. The protein was expressed and purified to high purity via anti-FLAG affinity resin and heparin column. A target RNA probe was generated through transcription and purified as a model RNA (FIG. 7). The complementary strand was generated with unmodified A or with m$^6$A replacing all A by using m$^6$ATP during the transcription; Applicants have confirmed that m$^6$ATP can be efficiently recognized by various polymerases (including Phi6 RNA replicase) in order to generate the anti-sense strand with m$^6$A replacing A. The two strands were annealed. Deaminations of both dsRNA using recombinant dADAR were tested. The treated product was reverse transcribed, amplified, and then inserted into a vector through TA-cloning. The A-to-G mutation ratio on the target strand was counted through colony picking and Sanger sequencing. As expected, with A on the complementary strand, ~20-30% deamination was observed for each of the seven A on the target strand. A similar deamination ratio for each A on the complementary strand was also observed. When all A was replaced with m$^6$A on the complementary strand, almost no deamination of the complementary strand and close to 50-60% deamination for each A on the target strand was observed (FIG. 7). The deamination ratio of the target strand doubled with m$^6$A replacing unmodified A on the complementary strand.

Challenge 3, quantification controls: In order to generate a control sample, Applicants further propose a demethylation approach to provide control transcripts with minimum m$^6$A methylation (FIG. 8A). Cellular mRNA can be isolated and subjected to ALKBH5-catalyzed m$^6$A demethylation. ALKBH5 is one of the two known m$^6$A RNA demethylases identified. Recombinant ALKBH5 is highly active and can remove most m$^6$A (90%) from mammalian mRNA in vitro as shown in FIG. 8B. For a quantification control, the following steps can be performed: i) Separate the purified polyA-tailed RNA into two portions. One portion with be subjected to the ALKBH5-catalyzed m6A demethylation to remove most m$^6$A on RNA. ii) Then, both mRNA samples (after forming duplex RNA) will be subjected to the dADAR-mediated deamination, RT-PCR amplification, and high-throughput sequencing. iii) Because m$^6$A is resistant to deamination it will be read as A in the sample without ALKBH5 treatment. In the ALKBH5-treated control m$^6$A is converted to A, which is deaminated to inosine in the deamination step and will be read as G. A comparison of the two parallel sequencing data will accurately reveal m$^6$A sites at base resolution and eliminate potential RNA editing at the modification site (unmodified A-to-I) and potential biases of the deamination step.

Figure 8C:
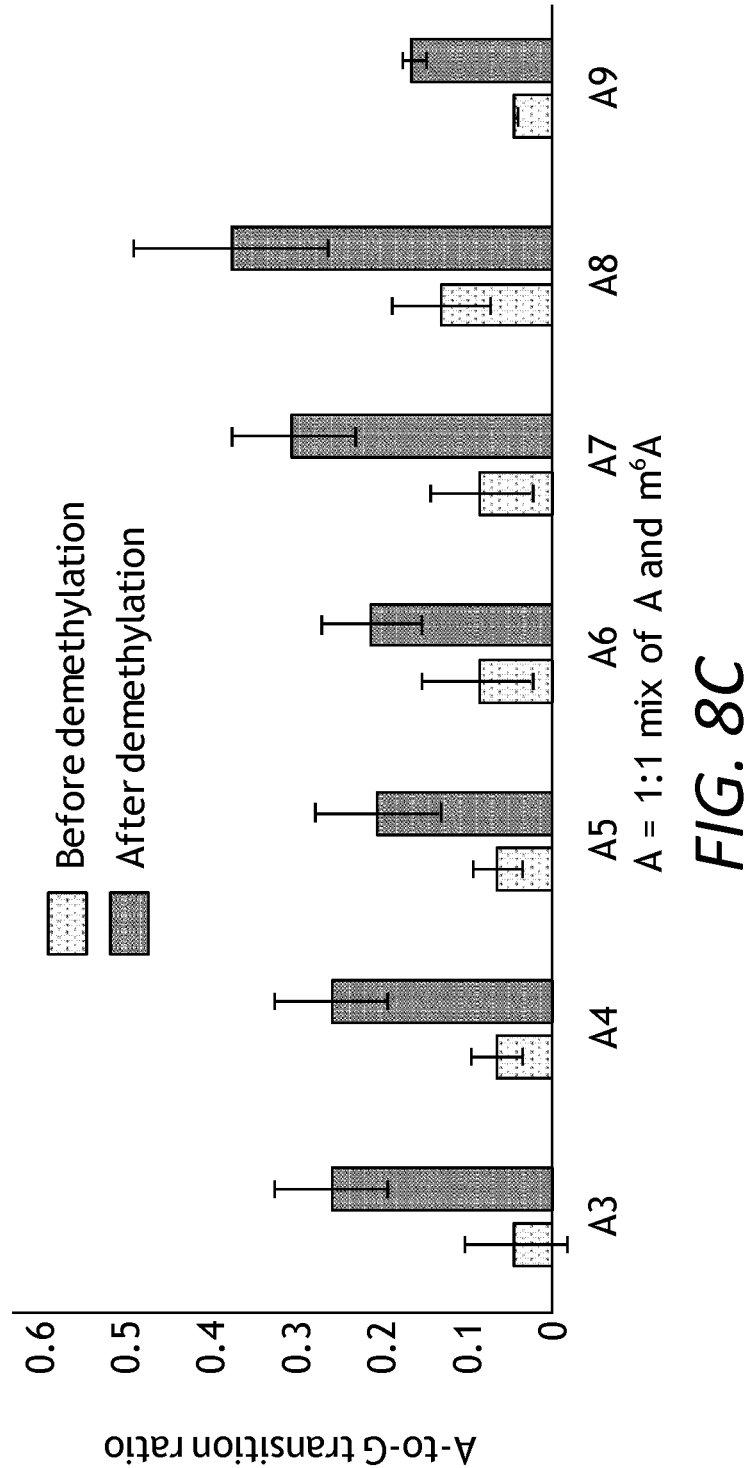

Applicants tested whether the A-to-G mutation ratio changes with and without demethylation reaction as proposed. A- and m$^6$A-containing target strands were synthesized and mixed together in 1:1 ratio. The ssRNA substrate was split into two portions, a control portion and a portion subjected to ALKBH5-mediated demethylation (FIG. 8A). The dsRNA was deaminated by dADAR and then converted to DNA for Sanger sequencing. The results revealed significant differences between samples with and without demethylation treatment (FIG. 8B and FIG. 8C). The A-to-G transition occurred on partially methylated target strand, which represents the ratio of deamination. In the absence of demethylation, the deamination efficiency for the target strand ranged around 5-15% for the 1:1 mixture of A:m$^6$A. With demethylation treatment, the deamination efficiency went up to around 20-35% for the target strand. The comparison of the two results can lead to accurate assignments of the m$^6$A sites as well as correction of other factors that may affect the dADAR-mediated deamination.

Applicants have applied Deam-m$^6$A-seq to isolated mRNA from HeLa cells by using Phi6 RNA replicase to generate duplex RNA (with m$^6$A on the opposite anti-sense strand). A shallow sequencing was performed with promising results. In MALAT1 lncRNA as an example, we observed 20-60% A-to-G transition mutations at most A sites.

One main concern is that the ADAR-mediated deamination of unmodified A is not stoichiometric. But with m$^6$A in the complementary strand to extend deamination of the target strand and a new buffer system that stabilizes duplex and promotes dADAR activity, the deamination efficiency can be improved up to ~75%. To provide quantitative information of the modification percentage at each site, spike-in controls that contain different percentages of m$^6$A/A can be used. Generating a calibration curve will enable more precise measurements of the methylation fractions at each sites. The use of spike-in controls and generation of a calibration curve provided more accurate estimates of the modification fractions.

Adenosine deamination in RNA-DNA Duplex

Figure 9A:
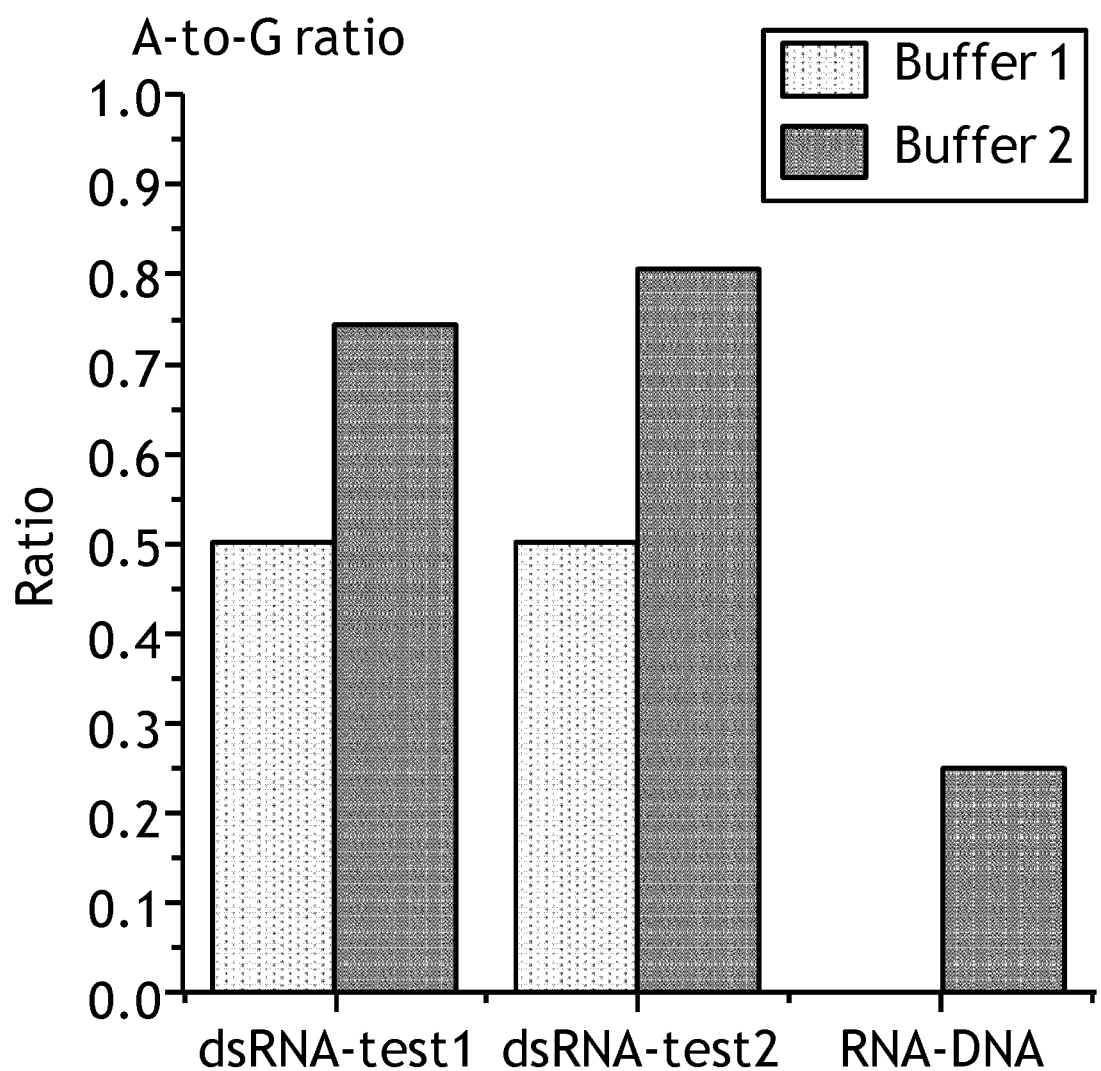

Applicants have recently discovered a new buffer system (Example 2) that stabilizes duplex and significantly promotes deamination of unmodified A in duplex RNA (with m$^6$A on the complementary strand) by dADAR to ~75%. Under the same conditions dADAR is active on RNA-DNA duplex substrates. We observed ~25% A-to-G mutations for unmodified A in RNA of an RNA-DNA model substrate after treating with dADAR (FIG. 9A). Since both duplex RNA and RNA-DNA duplex adopt the similar A-form conformation, this result may not be surprising; the observation nevertheless opens a possibility to further increase the deamination efficiency for A (FIG. 9B): 1. Through regular RNase H-minus RT, RNA-DNA hybrid duplex can readily be generated from a pool of isolated mRNA. dADAR does not work on the DNA strand. Therefore, its activity will be confined to the RNA strand. The dADAR-mediated deamination leads to progressive weakening of the duplex until the two strands separate. 2. The mixture can then be treated with DNase to digest all DNA, purify RNA, and perform another round of RT to generate another pool of RNA-DNA hybrid duplexes that form perfectly complementary strands, now with the deaminated RNA product from step 1. 3. The dADAR-mediated deamination will be performed, and then the procedure goes back to step 1 for iterative rounds of duplex generation and RNA deamination. 4. After several rounds of RT-deamination-DNA digestion-RT, the deamination efficiency of unmodified A could in principle reach stoichiometric. Library will be constructed for subsequent sequencing.

With the RNA-DNA hybrid duplex as the substrate, Applicants can selectively digest DNA after the strand separation (because of deamination) and perform reverse transcription to generate the new DNA stands complementary to the deaminated and un-deaminated RNAs for another round of deamination. In principle, iterative rounds of this procedure will allow for much higher deamination efficiency. An ALKBH5-treated control sample with minimum m$^6$A will be processed in parallel. Comparison of these two samples could accurately reveal m$^6$A with base-resolution accuracy. Potential deamination of m$^6$A can be monitored in order to ensure minimum interference. This approach offers one of the best current solutions for m$^6$A sequencing at base resolution.

Example 2

Deam-m$^6$A-seq

In RNA technologies, RNA processing and modification are important features, closely related to its biological functions. Particularly, N$^6$-methyladenosine (m$^6$A) is a widely present modification found within eukaryotic messenger RNA and various nuclear non-coding RNAs. Recent discoveries have revealed that methylation of adenosine in mRNA is a dynamic and reversible process. m$^6$A formation in the nucleus is catalyzed by a complex containing methyltransferase like 3 (METTL3), methyltransferase like 14 (METTL14), and Wilms' tumor 1-associating protein (WTAP). Two human AlkB family proteins, fat mass and obesity-associated protein (FTO) and ALKBH5, serve as RNA demethylases to remove m$^6$A in mammalian polyAt-tailed RNA. The "reader" protein YTHDF2, an m$^6$A specific binding protein which is shown to interact with thousands of mRNA targets, mediates its substrates to a methylation-dependent mRNA decay, demonstrating a significant role of methylation in mRNA metabolism. The latest work on METTL3 knockout embryonic stem cells also indicates the critical role of m$^6$A in cell differentiation and its regulatory relationship with microRNA.

Currently, transcriptome-wide m$^6$A detection is based on antibody-specific enrichment, followed by high-throughput sequencing (m$^6$A-seq, or MeRIP-seq). Even a photo-cross-linking-assisted strategy has been developed to significantly improve the resolution of m$^6$A-seq (PA-m$^6$A-seq), the lack of direct conversion tool to differentiate methylated and unmethylated adenosine still hinders the single-nucleoside resolution detection and quantitative analyses of methylation across the entire transcriptome, which is of great importance to further investigate the biological significance of the methylation modification.

Described herein is an enzyme-based approach, ADAR-mediated adenosine deamination sequencing (Deam-m$^6$A-seq), to map m$^6$A in a transcriptome-wide manner at single-nucleoside resolution.

Design and Innovation: *Drosophila* Adenosine Deaminase that Acting on RNA (dADAR) was chosen as the tool enzyme to catalyze deamination process (FIG. 6).

The following describes exemplary method steps useful in the methods and compositions of the disclosure. Certain embodiments may comprise the reagents and methods described below.

I. Step 1: dADAR Substrate Preparation:

A. Formation of dsRNA by Employing Phi6 RNA replicase and N$^6$-methyl-ATP to Replace Normal ATP Phi6 RNA replicase is a high-efficient RNA replicase from virus, which is able to generate complementary antisense RNA strand without the assistance of primer. Phi6 RNA replicase recognizes free 3' hydroxyl group of RNA molecule to initiate the synthesis, typically producing the full-length dsRNA for the RNA/DNA template.

Figure 10A:
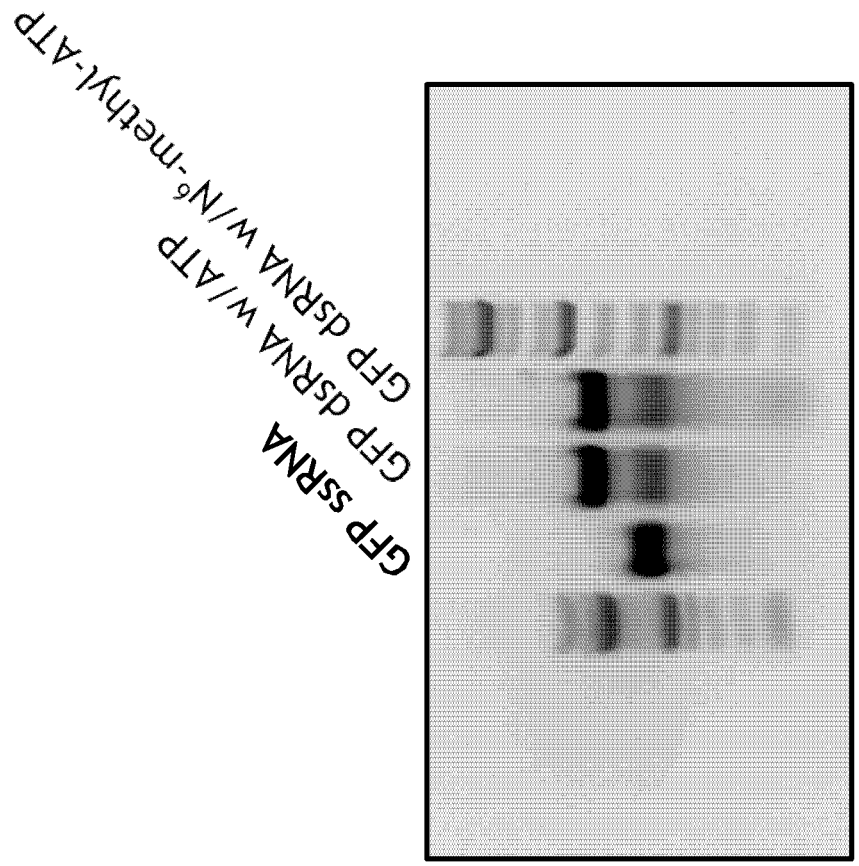
FIGS. 10A-B. Preparation of dADAR substrate by using (A) Phi6 RNA replicase with $N^6$-methyl-ATP to form dsRNA and (B) SuperScript II Reverse Transcriptase (or other alternative reverse transcriptases) to form RNA-DNA hybrid.
Figure 10A:
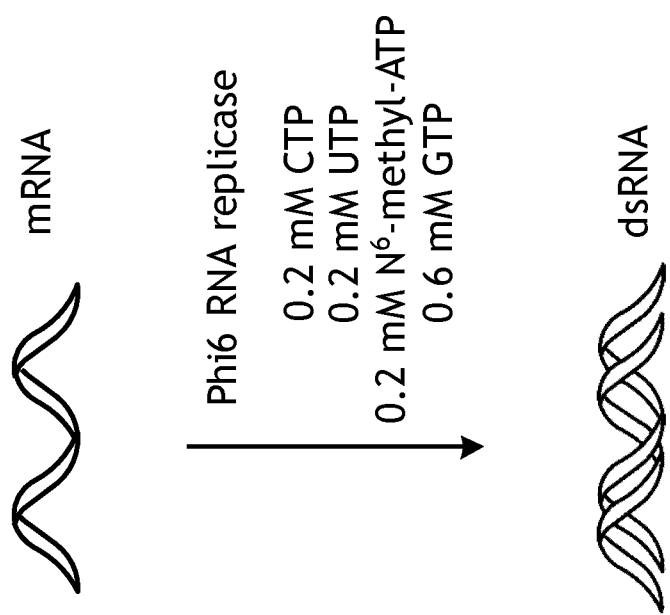

To avoid the nonsense deamination occurring on complementary RNA strand which destabilizes dsRNA and also consumes the catalytic turnover capability of dADAR, Applicants proposed to incorporate m$^6$A instead of A in complementary strand by utilizing N$^6$-methyl-ATP, which was not tested before. Surprisingly, the incorporation efficiency of N$^6$-methyl-ATP by Phi6 RNA replicase is similar to that of normal ATP, ensuring the productivity of m$^6$A-incorporated dsRNA for further deamination treatment (FIG. 10A).

B. Formation of RNA-DNA hybrid as dADAR substrate.

dADAR does not recognize RNA-DNA hybrid in typical buffer system. dATP and

Figure 10B:
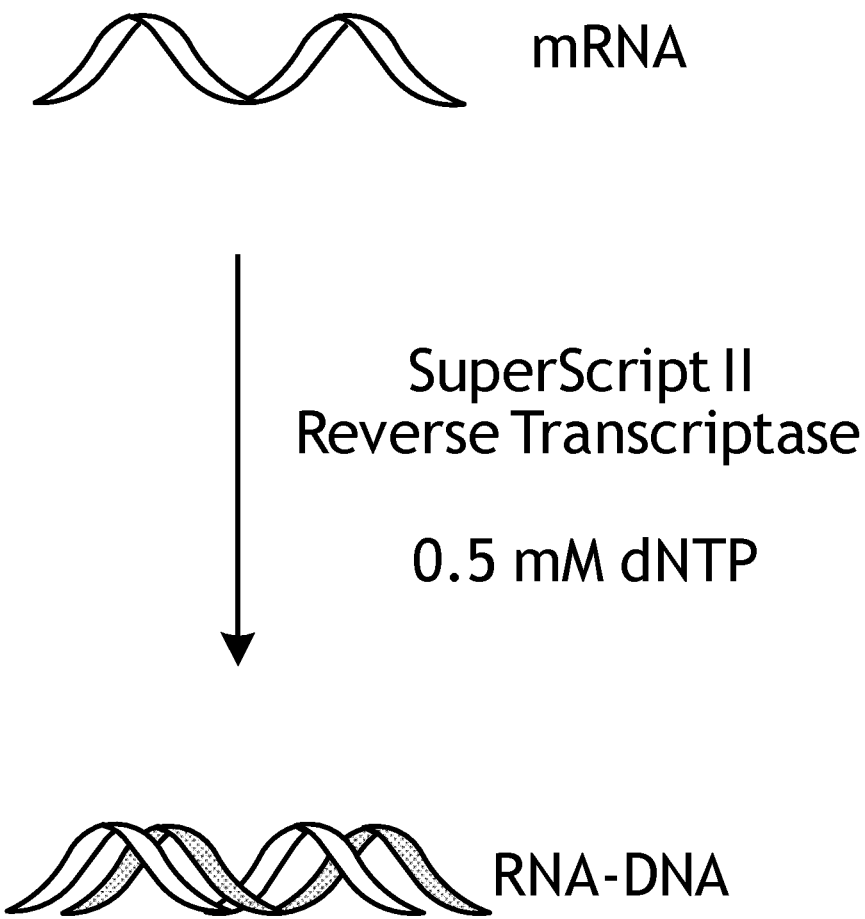

GTP-containing reaction buffers were tested to investigate whether the deamination activity could be improved. It was eventually found that dADAR could react with RNA-DNA hybrid with GTP in the reaction buffer (FIG. 10B).

II. Step 2: deamination control setup

A. Demethylated Control Group

The deamination activity of dADAR on substrate is barely affected by sequences of substrate. However, the tiny uneven deamination reactivity on adenosine in different contexts has great negative effect on the power of differentiating methylated adenosine from unmethylated. Thus, setting up an effective control group for further data analyses is extremely significant.

In theory, comparing deamination results of methylated and unmethylated transcripts is the best way to 1) rule out any context biases on unmethylated adenosine and 2) amplify the deamination conversion effect on methylated adenosine. Applicants considered the use of m$^6$A demethylases to get rid of m$^6$A modification transcriptome-wide. Applicants tested both FTO and ALKBH5, finding that ALKBH5 affords the better efficiency of removing methyl group of adenosine (FIG. 8B). As the flowchart shows, fragmented transcriptome is split into two parallel experimental group and after the treatment of ALKBH5, one is original and the other is demethylated control group, both of which are applied to substrate preparation step. The strategy indeed shows its efficiency to enhance A-to-G transition ratio on methylated sites on our model study (FIG. 8C).

B. Relationship Between Deamination Efficiency and Methylation Level Demonstrated by Calibration Curve Even we have already optimized the entire deamination reaction from substrate to reaction condition, it is still unlikely to convert all unmethylated adenosine to inosine in deaminase treatment. Considering the relatively low level of methylation, a cutoff/criteria is required for confidently detecting m$^6$A and quantifying methylation on each site. Therefore, a relationship between deamination efficiency and methylation level on each adenosine is necessary for quality control and data analyses.

T7 and T3 RNA polymerases are compatible with several modified nucleoside triphosphate and are able to generate modified nucleoside containing RNA fragments. We found that N$^6$-methyl-ATP can be used to form the RNA strand. By using this strategy, we can prepare a set of samples with different methylation levels, with which a calibration curve, demonstrating the relationship between deamination efficiency (indicated by A-to-G transition ratio in high-throughput sequencing) and methylation level, can be prepared.

C. Step 3: Deamination Condition Optimization

The best buffer system for deamination reaction of dADAR (on dsRNA and RNA-DNA hybrid) is shown below:

| 1X Reaction buffer system | |
|---|---|
| Component | Final Concentration |
| Tris-HCl (pH 7.9) | 20 mM |
| KCl | 100 mM |
| ZnCl$_2$ | 20 µM |
| DTT | 1 mM |
| MgCl$_2$ | 1 µM |
| GTP | 4 mM |

The reactivity under two different concentrations of GTP in the buffer system were tested. With 4 mM GTP in buffer, the reactivity enhanced significantly (FIG. 9A).

III. Exemplary Procedure for Effective Deamination of RNA in RNA-DNA Hybrid Duplex The observation that dADAR works effectively on RNA-DNA duplex in the presence of GTP opens a possibility to further increase the deamination efficiency for A (FIG. 9B):

Through regular RNase H-minus RT Applicants can readily generate RNA-DNA hybrid duplex from a pool of isolated mRNA. dADAR does not work on the DNA strand. Therefore, its activity will be confined to the RNA strand. The dADAR-mediated deamination leads to progressive weakening of the duplex until the two strands separate. Applicants will then treat the mixture with DNase to digest all DNA, purify RNA, and perform another round of RT to generate another pool of RNA-DNA hybrid duplexes that form perfectly complementary strands, now with the deaminated RNA product from step 1. The dADAR-mediated deamination will be performed, and then the procedure goes back to step 1 for iterative rounds of duplex generation and RNA deamination. After several rounds of RT-deamination-DNA digestion-RT, the deamination efficiency of unmodified A could in principle reach stoichiometric. Library will be constructed for subsequent sequencing.

With the RNA-DNA hybrid duplex as the substrate, Applicants can selectively digest DNA after the strand separation (because of deamination) and perform reverse transcription to generate the new DNA stands complementary to the deaminated and un-deaminated RNAs for another round of deamination. In principle, iterative rounds of this procedure will allow us to achieve much higher deamination efficiency. An ALKBH5-treated control sample with minimum m$^6$A will be processed in parallel. Comparison of these two samples could accurately reveal m$^6$A with base-resolution accuracy. Applicants can monitor potential deamination of m$^6$A in order to ensure minimum interference. This approach offers one of the best current solutions for m$^6$A sequencing at base resolution.

Example 3

RNA Immobilization and Iterative Deam-Seq

The deamination process converts unmethylated adenosine to inosine and generates inosine-uracil/thymine mismatch in dsRNA/RNA-DNA hybrid, which significantly destabilizes the duplex structure. However, the presence of the duplex structure is critical for achieving high transition ratio through effective deamination.

To overcome this drawback, Applicants propose to iteratively perform deamination reaction on target strand to convert as many unmethylated adenosines to inosine as possible. In dsRNA Deam-seq, the introduction of the antisense complementary strand is critical for the deamination reaction; however, the addition of the complementary strand also interferences on iterative deamination reaction since after several rounds of formation of dsRNA, the original target strand, which is the "real" transcriptome, is diluted by artificially synthesized strand.

Figure 11A:
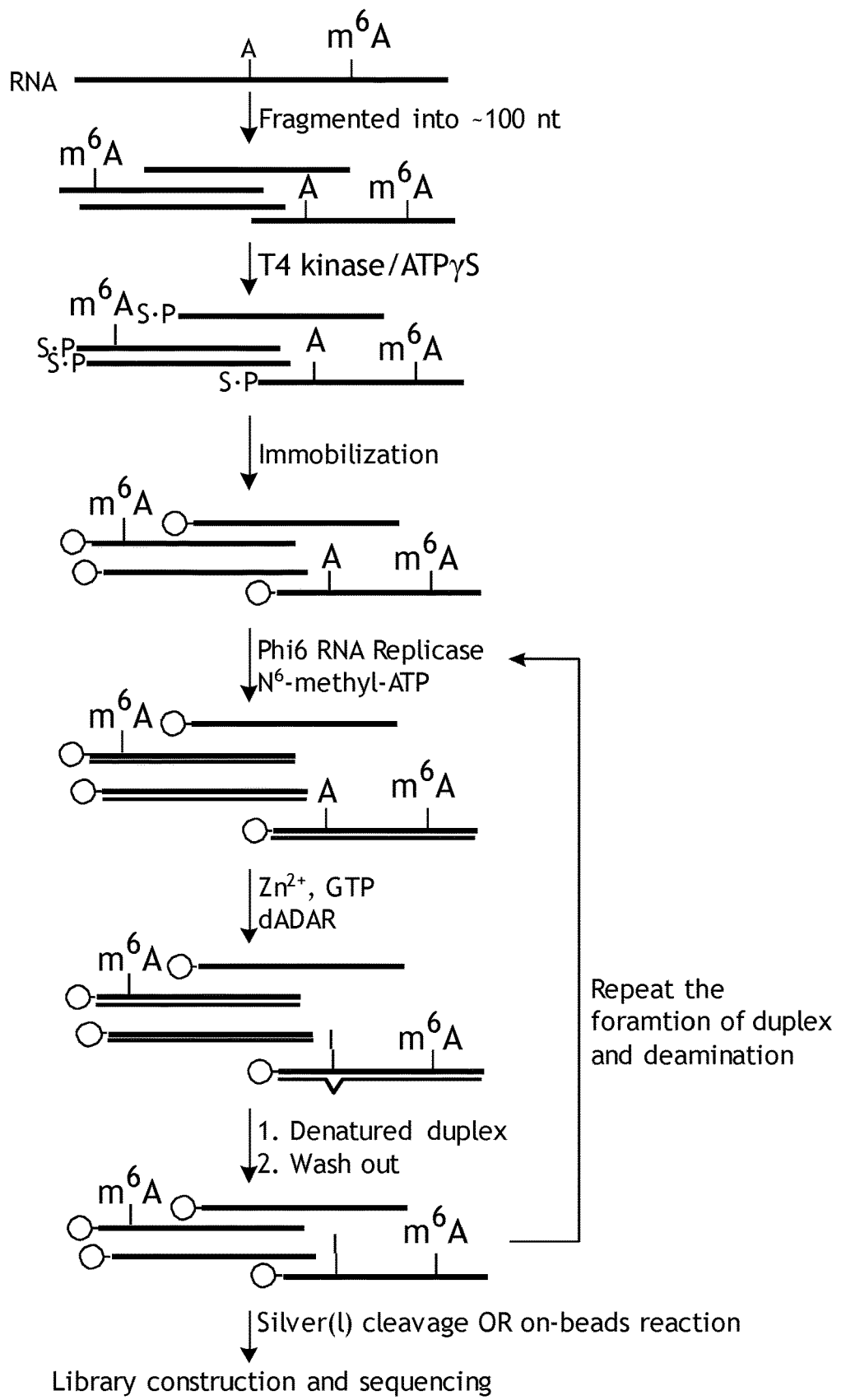
FIGS. 11A-B. Depicted is the scheme of the immobilization and iterative Deam-seq strategy (A). ATPγS is Adenosine 5'-[γ-thio]triphosphate, in which γ-phosphate is modified with a sulfur and transferred by T4 PNK to oligonucleotides for further reaction (B).
Figure 11B:
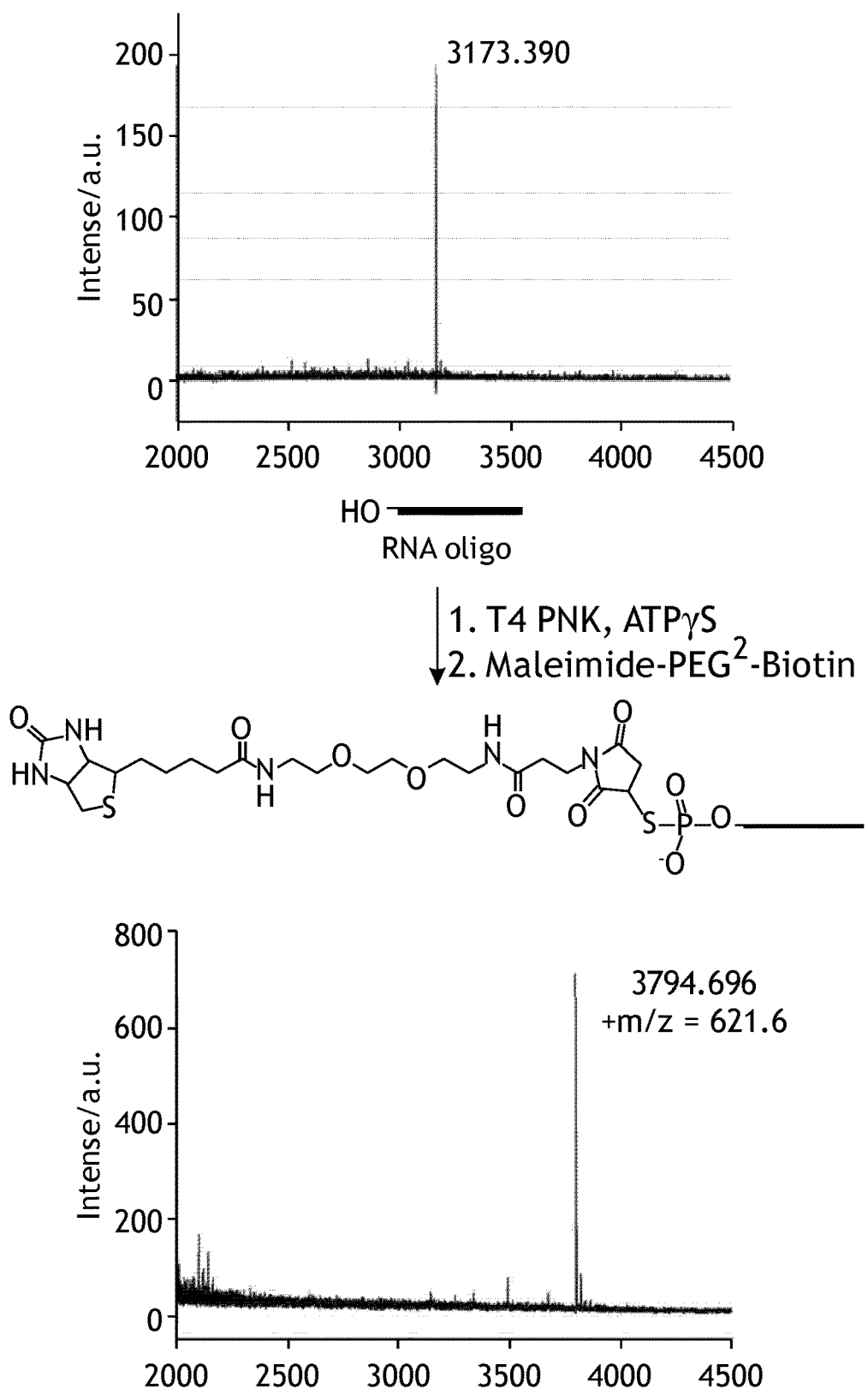
Figure 12A:
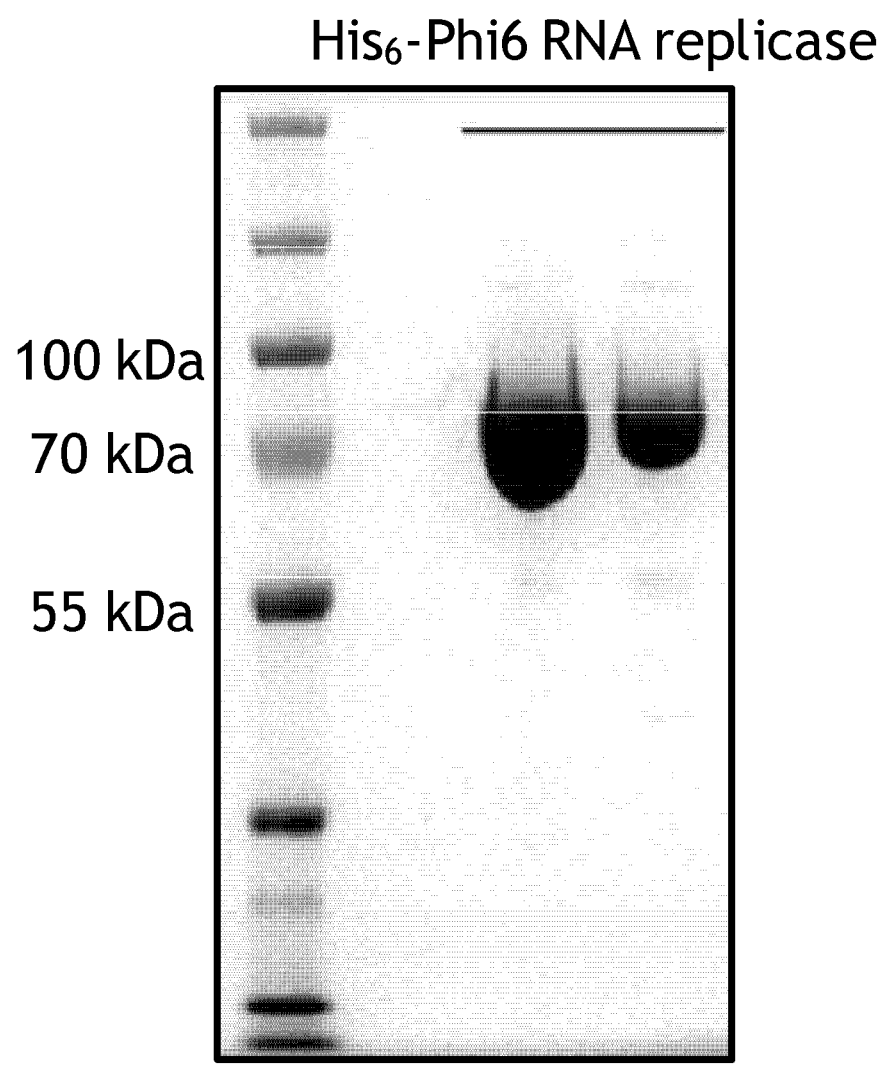
FIGS. 12A-C. (A) Coomassie brilliant blue staining of recombinant $His_6$-Phi6 RNA replicase purified from E. coli, after Source Q ion exchange. (B) Adapted Bismark analysis workflow demonstrated how A-to-G transition containing read is precisely mapped back to the reference genome. (C) MTSEA-biotin phosphothioate labeling. The reactions were monitored by MALDI-TOF. (C(1)) The RNA probe control. (C(2)) The phosphothioate added probe. (C(3)) The biotinylated probe. (C(4)) The DTT mediated cleaved probe.
Figure 12B:
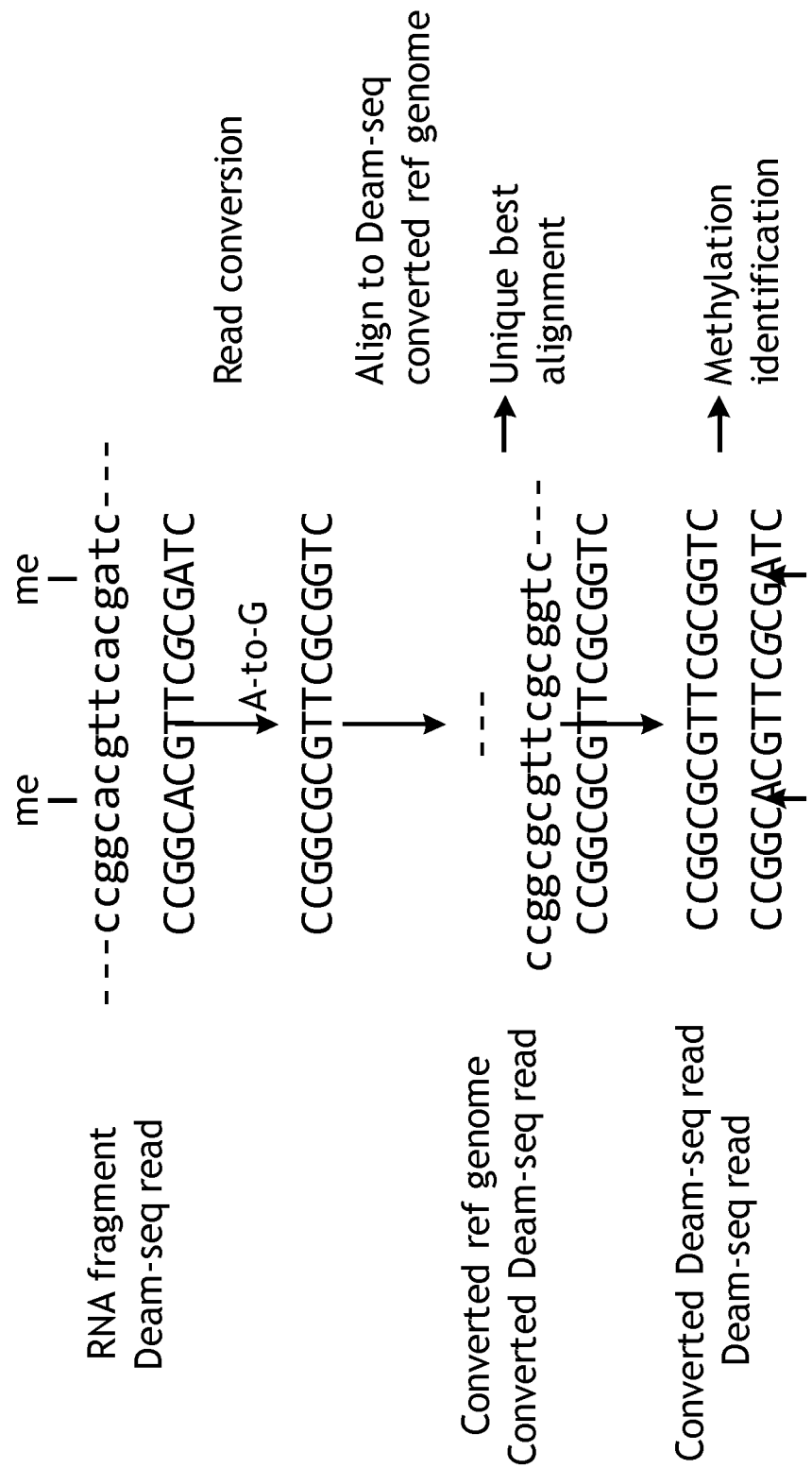
Figure 12C:
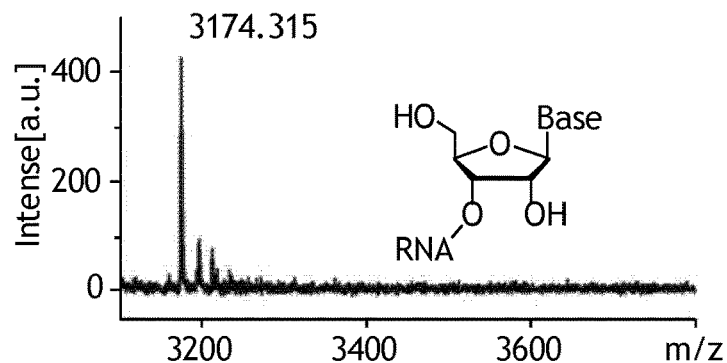
Figure 12C:
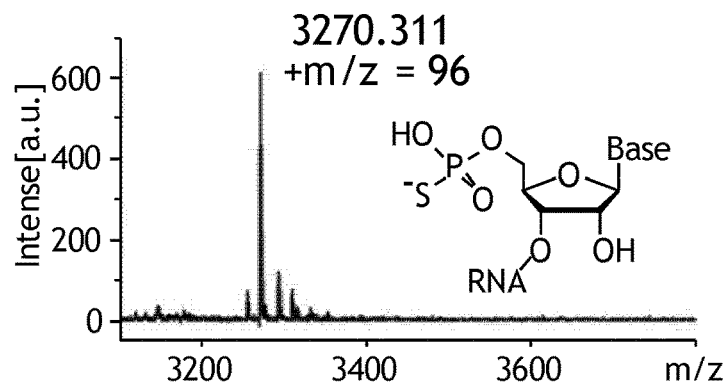
Figure 12C:
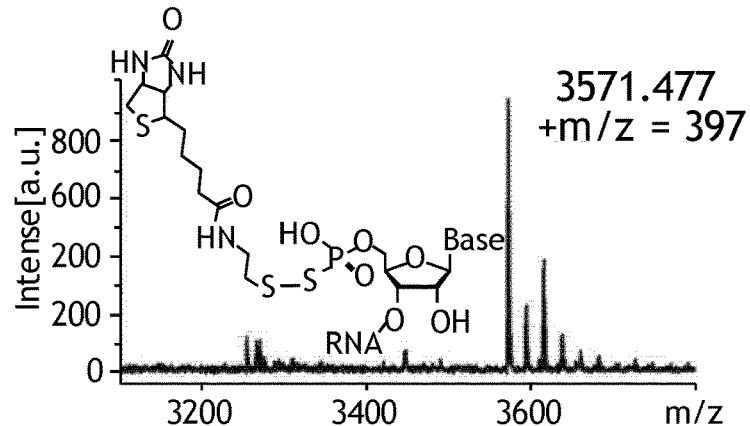
Figure 12C:
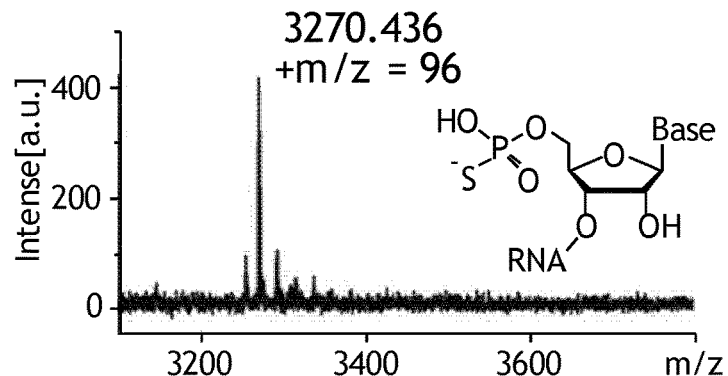

The best approach to differentiate the original target strand from artificially synthesized complementary strand is to selectively label the original one and immobilize it on a solid support. Therefore, we have designed the RNA immobilization and iterative Deam-seq strategy (FIG. 11).

RNA fragment is first attached with a 5'-phosphothioate group by using T4 polynucleotide kinase and ATP-γS. Then the labeled RNA fragment reacts with a solid support with iodoacetamide (or other functional groups that react with phosphothioate) that is commercially available. The immobilize RNA serves as the template for the formation of dsRNA/RNA-DNA duplex and is applied to deamination reaction system.

After the conversion of as many adenosines as possible to inosine during deamination, the artificial anti-sense strand no longer stably interacts with target strand, which can be denatured and washed out. Then, a second-round of the formation of dsRNA/RNA-DNA duplex and subsequent deamination is followed (FIG. 11). By using this strategy, iterative deamination can be achieved. Not only does the deamination efficiency increase, but also the target strand is the only strand to be sequenced at the end of the process.

Besides reacting ATP-γS with iodoacetamide, other 5' end labeling and immobilization strategies can be applied. For instance, after 5'-phosphothioate transfer, labeled RNA/DNA can also react with maleimide derivatives (for example, maleimide biotin) and then be immobilized on streptavidin beads.

The high reactivity of phosphothioate transfer and high yield of solid phase capture may also enable our strategy to enrich cell free oligonucleotides (RNA or DNA) for clinical diagnostics. Current enrichment approaches are generally based on direct extraction and absorptions through electrostatic or hydrophobic interaction, which either is less efficient or hardly to be further treated for further experiments. Our approach anchors oligonucleotides at 5' terminal, which has little effect on most biochemical treatment; also, the solid phase separation can afford iterative flow-through and clean-up steps, leading to high efficiency and low background noises.

Example 2

PHi6 RNA Replicase Expression and Purification

The Phi6 RNA replicase gene was synthesized at GeneArt (Thermo Fisher). The gene was directly cloned into pMCSG19 vector by using Gibson assembly method. The construct was verified by Sanger sequencing then transformed to PRK1037 competent cell.

For protein expression and purification, the transformant was grown at 37° C. overnight as a starter culture. In the next day it was used to inoculate LB media and grown at 37° C. to an absorbance at 600 nm of 0.8. Then, the media culture was cooled down to 16° C. and induced by adding 1 mM isopropyl-β-D-thiogalactopyranoside at 16° C. for 18 hrs. The bacterial cells were pelleted by centrifugation and homogenized in lysis buffer containing 20 mM Tris-HCl pH 8.0, 200 mM NaCl and 1 mM phenylmethanesulfonylfluoride (PMSF) by a cell homogenizer. The supernatant was subjected to Ni-NTA columns for affinity purification. The protein was eluted in 20 mM Tris-HCl, pH 8.0, 200 mM NaCl and 500 mM imidazole, then directly subjected to Heparin column (GE Healthcare). Elution of the bound protein was performed with a 150 mM to 1 M NaCl gradient buffered with 50 mM Tris-HC1, pH 8.0 and 1 mM EDTA. Fractions containing Phi6 RNA replicase was further purified by Source Q column (GE Healthcare) with a 100 mM to 1 M NaCl gradient. The fraction was pooled together and concentrated for storage.

Example 3

An Alternative Biotinylation Labeling Reaction

Besides maleimide sulfur reaction, an alternative approach was also developed. The reaction between the phosphothioate group at the 5' terminal of RNA and methanethiosulfonate biotin (MTSEA-biotin) labels the RNA molecule with biotin via the formation of disulfide bond, which can be cleaved by DTT treatment.

The advantage of this methanethiosulfonate disulfide formation strategy is: 1) the high activity of MTSEA-biotin makes the labeling more efficient under milder condition (incubated at room temperature for 20 min); 2) the DTT cleavage step provides high recovery yield of selective pulldown RNA molecule from the streptavidin beads, ensuring the application of Deam-seq to limited amount samples.

Example 4

Data Analysis Pipeline

Regarding the fact that Deam-seq original reads contain multiple specific mutations which is very similar to bisulfite sequencing, the inventors chose to adapt Bismark, a widely used bisulfite sequencing analysis tool, to the Deam-seq analysis by performing A-to-G transition instead of its original C-to-T transition. The modified Bismark script is able to uniquely map the raw data back to human transcriptome and report both the transition sites and transition frequency of each site as analysis output, which could be used for further statistical test.

With the adapted Bismark tool, the pipeline to analyze Deam-seq and translate the raw data into frequency is described as following:

Step 1: use a homemade script to convert the raw data .fastq file to its reverse complementary sequence .fastq.rc. The Illumina TruSeq stranded mRNA library preparation kit specifically labels the transcriptome to effectively distinguish the first-strand cDNA from the second strand, keeping the stranded information in raw data. Given the great likelihood that Deam-seq libraries contain both "sense" (the transcriptome) and "anti-sense" (the artificial "reverse complement-ome") reads, it is of great necessity to process all reads to make sure that the reads are in their original directions as how they are annotated in genome.

Step 2: apply the adapted Bismark tool to map the converted raw data .fastq.rc file back to reference genome. In this step, both the raw reads from Step 1 and the reference genome are first transformed to replace all A sites with G sites, then two parallel alignment instances between original and converted versions of raw data and reference enable one to precisely and uniquely map the reads; meanwhile, conversion status of each A site is also recorded based on the parallel alignment, which is further reported as the A-to-G transition frequency.

Step 3: employ Bedtools intersect to extract the transcriptome oriented A-to-G transition frequency for further statistical analysis. Even the reverse complementary strand in dsRNA could be deaminated in the treatment, only the strand with the same direction as the transcriptome is the target for m⁶A analysis. Using the transcriptome based reference, Bedtools intersect tool efficiently extracts the "on-transcript-strand" part and reports in a separate file recording the conversion status of each A sites covered by raw data. An example report is shown in Table 1.

TABLE 1

Transcriptome direction A-to-G report "on-transcript-strand"

| Categories of A sites on-transcript-strand | Counts |
| --- | --- |
| A->A only Events[a] | 8,576,879 |
| A->A only Sites[b] | 2,217,080 |
| A->G only Events[c] | 9,234,159 |
| A->G only Sites[d] | 2,110,312 |
| A&G both A->A Events[e] | 25,384,512 |
| A&G both A->G Events[f] | 28,141,722 |
| A&G both Sites[g] | 2,702,153 |

Notes:
[a]A->A only Events: on A sites which do not have A-to-G mutation detected, the covered A reads counted as "events".
[b]A->A only Sites: the A sites which do not have A-to-G mutation detected.
[c]A->G only Events: on A sites which have all A read as G, the covered G reads counted as "events".
[d]A->G only Sites: the A sites which have all A read as G.
[e]A&G both A->A Events: on A sites which have both A and G detected, the covered A reads counted as "events".
[f]A&G both A->G Events: on A sites which have both A and G detected, the covered G reads counted as "events".
[g]A&G both Sites: the A sites which have both A and G detected.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications described herein are specifically incorporated by reference for all purposes.

REFERENCES

The following references, to the extent that they provide exemplary procedural or other details supplementary to those set forth herein, are specifically incorporated herein by reference.

1. Cantara W A, Crain P F, Rozenski J, McCloskey J A, Harris K A, Zhang X, Vendeix F A P, Fabris D, Agris P F. The RNA modification database, RNAMDB: 2011 update. Nucleic Acids Res. 2011; 39 (Database issue): D195-D201. PMC3013656.
2. Machnicka M A, Milanowska K, Osman Oglou O, Purta E, Kurkowska M, Olchowik A, Januszewski W, Kalinowski S, Dunin-Horkawicz S, Rother K M, Helm M, Bujnicki J M, Grosjean H. MODOMICS: a database of RNA modification pathways—2013 update. Nucleic Acids Res. 2013; D262-7. PMC3531130.
3. He C. Grand challenge commentary: RNA epigenetics? Nat Chem Biol. 2010; 6(12):863-5. PMC pending.
4. Jia G, Fu Y, Zhao X, Dai Q, Zheng G, Yang Y, Yi C, Lindahl T, Pan T, Yang Y, He C. N⁶-Methyladenosine in nuclear RNA is a major substrate of the obesity-associated FTO. Nat Chem Biol. 2011; 7(12):885-7. PMC3218240.
5. Liu J, Yue Y, Han D, Wang X, Fu Y, Zhang L, Jia G, Yu M, Lu Z, Deng X, Dai Q, Chen W, He C. A METTL3-METTL14 complex mediates mammalian nuclear RNA N⁶-adenosine methylation. Nat Chem Biol. 2014; 10(2): 93-5. PMC3911877.
6. Wang X, Lu Z, Gomez A, Hon G C, Yue Y, Han D, Fu Y, Parisien M, Dai Q, Jia G, Ren B, Pan T, He C. N⁶-methyladenosine-dependent regulation of messenger RNA stability. Nature. 2014; 505(7481):117-20. PMC3877715.
7. Zheng G, Dahl J A, Niu Y, Fedorcsak P, Huang C-M, Li C J, Vågbø C B, Shi Y, Wang W-L, Song S-H, Lu Z, Bosmans Ralph P G, Dai Q, Hao Y-J, Yang X, Zhao W-M, Tong W-M, Wang X-J, Bogdan F, Furu K, Fu Y, Jia G, Zhao X, Liu J, Krokan H E, Klungland A, Yang Y-G, He C. ALKBH5 Is a Mammalian RNA Demethylase that Impacts RNA Metabolism and Mouse Fertility. Mol Cell. 2013; 49(1):18-29. PMC3646334.
8. Fu Y, Dominissini D, Rechavi G, He C. Gene expression regulation mediated through reversible m⁶A RNA methylation. Nat Rev Genet. 2014; 15(5):293-306. PMC pending.
9. Carlile T M, Rojas-Duran M F, Zinshteyn B, Shin H, Bartoli K M, Gilbert W V. Pseudouridine profiling reveals regulated mRNA pseudouridylation in yeast and human cells. Nature. 2014; 515(7525):143-6. PMC4224642.
10. Schwartz S, Bernstein Douglas A, Mumbach Maxwell R, Jovanovic M, Herbst Rebecca H, León-Ricardo Brian X, Engreitz Jesse M, Guttman M, Satija R, Lander Eric S, Fink G, Regev A. Transcriptome-wide Mapping Reveals Widespread Dynamic-Regulated Pseudouridylation of ncRNA and mRNA. Cell. 2014; 159(1):148-62. PMC4180118.
11. Dominissini D, Moshitch-Moshkovitz S, Schwartz S, Salmon-Divon M, Ungar L, Osenberg S, Cesarkas K, Jacob-Hirsch J, Amariglio N, Kupiec M, Sorek R, Rechavi G. Topology of the human and mouse m6A RNA methylomes revealed by m⁶A-seq. Nature. 2012; 485 (7397):201-6. PMC pending.
12. Meyer K, Saletore Y, Zumbo P, Elemento O, Mason C, Jaffrey S. Comprehensive Analysis of mRNA Methylation Reveals Enrichment in 3' UTRs and near Stop Codons. Cell. 2012; 149(7):1635-46. PMC3383396.
13. Batista P J, Molinie B, Wang J, Qu K, Zhang J, Li L, Bouley D M, Lujan E, Haddad B, Daneshvar K, Carter A C, Flynn R A, Zhou C, Lim K-S, Dedon P, Wernig M, Mullen A C, Xing Y, Giallourakis C C, Chang H Y. m⁶A RNA Modification Controls Cell Fate Transition in Mammalian Embryonic Stem Cells. Cell Stem Cell. 2014; 15(6):707-19. PMC4278749.
14. Chen T, Hao Y-J, Zhang Y, Li M-M, Wang M, Han W, Wu Y, Lv Y, Hao J, Wang L, Li A, Yang Y, Jin K-X, Zhao X, Li Y, Ping X-L, Lai W-Y, Wu L-G, Jiang G, Wang H-L, Sang L, Wang X-J, Yang Y-G, Zhou Q. m⁶A RNA Methylation Is Regulated by MicroRNAs and Promotes Reprogramming to Pluripotency. Cell Stem Cell. 2015; 16(3):289-301. PMC pending.
15. Geula S, Moshitch-Moshkovitz S, Dominissini D, Mansour A A, Kol N, Salmon-Divon M, Hershkovitz V, Peer E, Mor N, Manor Y S, Ben-Haim M S, Eyal E, Yunger S, Pinto Y, Jaitin D A, Viukov S, Rais Y, Krupalnik V, Chomsky E, Zerbib M, Maza I, Rechavi Y, Massarwa R, Hanna S, Amit I, Levanon E Y, Amariglio N, Stern-Ginossar N, Novershtern N, Rechavi G, Hanna J H. m⁶A mRNA methylation facilitates resolution of naïve pluripotency toward differentiation. Science. 2015; 347(6225): 1002-6. PMC pending.
16. Ping X-L, Sun B-F, Wang L, Xiao W, Yang X, Wang W-J, Adhikari S, Shi Y, Lv Y, Chen Y-S, Zhao X, Li A, Yang Y, Dahal U, Lou X-M, Liu X, Huang J, Yuan W-P, Zhu X-F, Cheng T, Zhao Y-L, Wang X, Danielsen J M R, Liu F, Yang Y-G. Mammalian WTAP is a regulatory subunit of the RNA N6-methyladenosine methyltransferase. Cell Res. 2014; 24(2):177-89. PMC3915904.
17. Schwartz S, Agarwala Sudeep D, Mumbach Maxwell R, Jovanovic M, Mertins P, Shishkin A, Tabach Y, Mikkelsen Tarjei S, Satija R, Ruvkun G, Carr Steven A, Lander Eric S, Fink Gerald R, Regev A. High-Resolution Mapping Reveals a Conserved, Widespread, Dynamic mRNA Methylation Program in Yeast Meiosis. Cell. 2013; 155 (6):1409-21. PMC3956118.
18. Wang Y, Li Y, Toth J I, Petroski M D, Zhang Z, Zhao J C. $N^6$-methyladenosine modification destabilizes developmental regulators in embryonic stem cells. Nat Cell Biol. 2014; 16(2):191-8. PMC pending.
19. Liu N, Dai Q, Zheng G, He C, Parisien M, Pan T. $N^6$-methyladenosine-dependent RNA structural switches regulate RNA-protein interactions. Nature. 2015; 518 (7540):560-4. PMC4355918.
20. Spitale R C, Flynn R A, Zhang Q C, Crisalli P, Lee B, Jung J-W, Kuchelmeister H Y, Batista P J, Torre E A, Kool E T, Chang H Y. Structural imprints in vivo decode RNA regulatory mechanisms. Nature. 2015; 519(7544):486-90. PMC4376618.
21. Bokar J A. The biosynthesis and functional roles of methylated nucleosides in eukaryotic mRNA. Fine-tuning of RNA functions by modification and editing: Springer; 2005. p. 141-77. PMC pending.
22. Clancy M J, Shambaugh M E, Timpte C S, Bokar J A. Induction of sporulation in *Saccharomyces cerevisiae* leads to the formation of $N^6$-methyladenosine in mRNA: a potential mechanism for the activity of the IME4 gene. Nucleic Acids Res. 2002; 30(20):4509-18. PMC137137.
23. Hongay C F, Orr-Weaver T L. *Drosophila* Inducer of MEiosis 4 (IME4) is required for Notch signaling during oogenesis. Proc Natl Acad Sci U.S.A. 2011; 108(36): 14855-60. PMC3169142.
24. Zhong S, Li H, Bodi Z, Button J, Vespa L, Herzog M, Fray R G. MTA is an Arabidopsis messenger RNA adenosine methylase and interacts with a homolog of a sex-specific splicing factor. The Plant Cell Online. 2008; 20(5):1278-88. PMC2438467.
25. Yi C, Pan T. Cellular Dynamics of RNA Modification. Acc Chem Res. 2011; 44(12):1380-8. PMC pending.
26. Phizicky E M, Hopper A K. tRNA processing, modification, and subcellular dynamics: past, present, and future. RNA. 2015; 21(4):483-5. PMC4371247.
27. Kiss-László Z, Henry Y, Bachellerie J-P, Caizergues-Ferrer M, Kiss T. Site-Specific Ribose Methylation of Preribosomal RNA: A Novel Function for Small Nucleolar RNAs. Cell. 1996; 85(7):1077-88. PMC pending.
28. Squires J E, Patel H R, Nousch M, Sibbritt T, Humphreys D T, Parker B J, Suter C M, Preiss T. Widespread occurrence of 5-methylcytosine in human coding and non-coding RNA. Nucleic Acids Res. 2012; 40(11):5023-33. PMC3367185.
29. Umeda N, Suzuki T, Yukawa M, Ohya Y, Shindo H, Watanabe K, Suzuki T. Mitochondria-specific RNA-modifying Enzymes Responsible for the Biosynthesis of the Wobble Base in Mitochondrial tRNAs: Implications for the molecular pathogenesis of human mitochondria diseases. J Biol Chem. 2005; 280(2):1613-24. PMC pending.
30. Tones A G, Batlle E, Ribas de Pouplana L. Role of tRNA modifications in human diseases. Trends Mol Med.20(6): 306-14. PMC pending.
31. Desrosiers R, Friderici K, Rottman F. Identification of Methylated Nucleosides in Messenger RNA from Novikoff Hepatoma Cells. Proc Natl Acad Sci U.S.A. 1974; 71(10):3971-5. PMC434308.
32. Desrosiers R C, Friderici K H, Rottman F M. Characterization of Novikoff hepatoma mRNA methylation and heterogeneity in the methylated 5' terminus. Biochemistry. 1975; 14(20):4367-74. PMC pending.
33. Charette M, Gray M W. Pseudouridine in RNA: What, Where, How, and Why. IUBMB Life. 2000; 49(5):341-51. PMC pending.
34. Dubin D T, Stollar V, Hsuchen C-C, Timko K, Guild G M. Sindbis virus messenger RNA: the 5'-termini and methylated residues of 26 and 42 S RNA. Virology. 1977; 77(2):457-70. PMC pending.
35. Horowitz S, Horowitz A, Nilsen T W, Munns T W, Rottman F M. Mapping of N6-methyladenosine residues in bovine prolactin mRNA. Proc Natl Acad Sci U.S.A. 1984; 81(18):5667-71. PMC pending.
36. Rottman F, Shatkin A J, Perry R P. Sequences containing methylated nucleotides at the 5' termini of messenger RNAs: Possible implications for processing. Cell. 3(3): 197-9. PMC pending.
37. Yu Y T, Shu M D, Steitz J A. A new method for detecting sites of 2'-O-methylation in RNA molecules. RNA. 1997; 3(3):324-31. PMC1369484.
38. Jia G, Fu Y, He C. Reversible RNA adenosine methylation in biological regulation. Trends Genet. 2013; 29(2): 108-15. PMC3558665.
39. Meyer K D, Jaffrey S R. The dynamic epitranscriptome: $N^6$-methyladenosine and gene expression control. Nat Rev Mol Cell Biol. 2014; 15(5):313-26. PMC4393108.
40. Pan T. N6-methyl-adenosine modification in messenger and long non-coding RNA. Trends Biochem Sci. 2013; 38(4):204-9. PMC3608796.
41. Bokar J A, Shambaugh M E, Polayes D, Matera A G, Rottman F M. Purification and cDNA cloning of the AdoMet-binding subunit of the human mRNA ($N^6$-adenosine)-methyltransferase. RNA. 1997; 3(11):1233-47. PMC1369564.
42. Bokar J A, Rath-Shambaugh M E, Ludwiczak R, Narayan P, Rottman F. Characterization and partial purification of mRNA $N^6$-adenosine methyltransferase from HeLa cell nuclei. Internal mRNA methylation requires a multisubunit complex. J Biol Chem. 1994; 269(26): 17697-704. PMC pending.
43. Bodi Z, Zhong S, Mehra S, Song J, Li H, Graham N, May S, Fray R G. Adenosine methylation in *Arabidopsis* mRNA is associated with the 3' end and reduced levels cause developmental defects. Front Plant Sci. 2012; 3:48. PMC3355605.
44. Fustin J-M, Doi M, Yamaguchi Y, Hida H, Nishimura S, Yoshida M, Isagawa T, Morioka Masaki S, Kakeya H, Manabe I, Okamura H. RNA-Methylation-Dependent RNA Processing Controls the Speed of the Circadian Clock. Cell. 2013; 155(4):793-806. PMC pending.
45. Alarcon C R, Lee H, Goodarzi H, Halberg N, Tavazoie S F. $N^6$-methyladenosine marks primary microRNAs for processing. Nature. 2015; 519(7544):482-5. PMC pending.

46. Boissel S, Reish O, Proulx K, Kawagoe-Takaki H, Sedgwick B, Yeo G S H, Meyre D, Golzio C, Molinari F, Kadhom N, Etchevers H C, Saudek V, Farooqi I S, Froguel P, Lindahl T, O'Rahilly S, Munnich A, Colleaux L. Loss-of-Function Mutation in the Dioxygenase-Encoding FTO Gene Causes Severe Growth Retardation and Multiple Malformations. Am J Hum Genet. 2009; 85(1): 106-11. PMC2706958.

47. Dina C, Meyre D, Gallina S, Durand E, Korner A, Jacobson P, Carlsson L M S, Kiess W, Vatin V, Lecoeur C, Delplanque J, Vaillant E, Pattou F, Ruiz J, Weill J, Levy-Marchal C, Horber F, Potoczna N, Hercberg S, Le Stunff C, Bougneres P, Kovacs P, Marre M, Balkau B, Cauchi S, Chevre J-C, Froguel P. Variation in FTO contributes to childhood obesity and severe adult obesity. Nat Genet. 2007; 39(6):724-6. PMC pending.

48. Frayling T M, Timpson N J, Weedon M N, Zeggini E, Freathy R M, Lindgren C M, Perry J R B, Elliott K S, Lango H, Rayner N W, Shields B, Harries L W, Barrett J C, Ellard S, Groves C J, Knight B, Patch A-M, Ness A R, Ebrahim S, Lawlor D A, Ring S M, Ben-Shlomo Y, Jarvelin M-R, Sovio U, Bennett A J, Melzer D, Ferrucci L, Loos R J F, Barroso I, Wareham N J, Karpe F, Owen K R, Cardon L R, Walker M, Hitman G A, Palmer C N A, Doney A S F, Morris A D, Smith G D, Consortium TWTCC, Hattersley A T, McCarthy M I. A Common Variant in the FTO Gene Is Associated with Body Mass Index and Predisposes to Childhood and Adult Obesity. Science. 2007; 316(5826):889-94. PMC pending.

49. Scott L J, Mohlke K L, Bonnycastle L L, Willer C J, Li Y, Duren W L, Erdos M R, Stringham H M, Chines P S, Jackson A U, Prokunina-Olsson L, Ding C-J, Swift A J, Narisu N, Hu T, Pruim R, Xiao R, Li X-Y, Conneely K N, Riebow N L, Sprau A G, Tong M, White P P, Hetrick K N, Barnhart M W, Bark C W, Goldstein J L, Watkins L, Xiang F, Saramies J, Buchanan T A, Watanabe R M, Valle T T, Kinnunen L, Abecasis G R, Pugh E W, Doheny K F, Bergman R N, Tuomilehto J, Collins F S, Boehnke M. A Genome-Wide Association Study of Type 2 Diabetes in Finns Detects Multiple Susceptibility Variants. Science. 2007; 316(5829):1341-5. PMC pending.

50. Scuteri A, Sanna S, Chen W-M, Uda M, Albai G, Strait J, Najjar S, Nagaraja R, Orrú M, Usala G, Dei M, Lai S, Maschio A, Busonero F, Mulas A, Ehret G B, Fink A, Weder A B, Cooper R S, Galan P, Chakravarti A, Schlessinger D, Cao A, Lakatta E, Abecasis G R. Genome-Wide Association Scan Shows Genetic Variants in the FTO Gene Are Associated with Obesity-Related Traits. PLoS Genet. 2007; 3(7):e115. PMC pending.

51. Church C, Moir L, McMurray F, Girard C, Banks G T, Teboul L, Wells S, Bruning J C, Nolan P M, Ashcroft F M, Cox R D. Overexpression of Fto leads to increased food intake and results in obesity. Nat Genet. 2010; 42(12):1086-92. PMC3018646.

52. Fischer J, Koch L, Emmerling C, Vierkotten J, Peters T, Bruning J C, Ruther U. Inactivation of the Fto gene protects from obesity. Nature. 2009; 458(7240):894-8. PMC pending.

53. Ng H-H, Zhang Y, Hendrich B, Johnson C A, Turner B M, Erdjument-Bromage H, Tempst P, Reinberg D, Bird A. MBD2 is a transcriptional repressor belonging to the MeCP1 histone deacetylase complex. Nat Genet. 1999; 23(1):58-61. PMC pending.

54. Obata Y, Furusawa Y, Endo T A, Sharif J, Takahashi D, Atarashi K, Nakayama M, Onawa S, Fujimura Y, Takahashi M, Ikawa T, Otsubo T, Kawamura Y I, Dohi T, Tajima S, Masumoto H, Ohara O, Honda K, Hori S, Ohno H, Koseki H, Hase K. The epigenetic regulator Uhrf1 facilitates the proliferation and maturation of colonic regulatory T cells. Nat Immunol. 2014; 15(6):571-9. PMC pending.

55. Sharif J, Muto M, Takebayashi S-i, Suetake I, Iwamatsu A, Endo T A, Shinga J, Mizutani-Koseki Y, Toyoda T, Okamura K, Tajima S, Mitsuya K, Okano M, Koseki H. The SRA protein Np95 mediates epigenetic inheritance by recruiting Dnmt1 to methylated DNA. Nature. 2007; 450(7171):908-12. PMC pending.

56. Xu C, Wang X, Liu K, Roundtree I A, Tempel W, Li Y, Lu Z, He C, Min J. Structural basis for selective binding of m6A RNA by the YTHDC1 YTH domain. Nat Chem Biol. 2014; 10(11):927-9. PMC pending.

57. Liu N, Parisien M, Dai Q, Zheng G, He C, Pan T. Probing N6-methyladenosine RNA modification status at single nucleotide resolution in mRNA and long noncoding RNA. Rna. 2013; 19(12):1848-56. PMC3884656

58. Canaani D, Kahana C, Lavi S, Groner Y. Identification and mapping of $N^6$-methyladenosine containing sequences in Simian Virus 40 RNA. Nucleic Acids Res. 1979; 6(8):2879-99. PMC327900.

59. Dimock K, Stoltzfus C M. Sequence specificity of internal methylation in B77 avian sarcoma virus RNA subunits. Biochemistry-US. 1977; 16(3):471-8. PMC pending.

60. Harper J E, Miceli S M, Roberts R J, Manley J L. Sequence specificity of the human mRNA N6-adenosine methylase in vitro. Nucleic Acids Res. 1990; 18(19): 5735-41. PMC pending.

61. Kane S E, Beemon K. Precise Localization of m6A in Rous Sarcoma Virus RNA Reveals Clustering of Methylation Sites: Implications for RNA Processing. Mol Cell Biol. 1985; 5(9):2298-306. PMC pending.

62. Schibler U, Kelley D E, Perry R P. Comparison of methylated sequences in messenger RNA and heterogeneous nuclear RNA from mouse L cells. J Mol Biol. 1977; 115(4):695-714. PMC pending.

63. Wei C-M, Moss B. Nucleotide Sequences at the $N^6$-Methyladenosine Sites of HeLa Cell messenger Ribonucleic Acid. Biochemistry-US. 1977; 16(8):1672-6. PMC pending.

64. Ganot P, Bortolin M-L, Kiss T. Site-Specific Pseudouridine Formation in Preribosomal RNA Is Guided by Small Nucleolar RNAs. Cell. 1997; 89(5):799-809. PMC pending.

65. Decatur W A, Fournier M J. RNA-guided Nucleotide Modification of Ribosomal and Other RNAs. J Biol Chem. 2003; 278(2):695-8. PMC pending.

66. Barbosa E, Moss B. mRNA(nucleoside-2'-)-methyltransferase from vaccinia virus. Purification and physical properties. J Biol Chem. 1978; 253(21):7692-7. PMC pending.

67. McMahon M, Contreras A, Ruggero D. Small RNAs with big implications: new insights into H/ACA snoRNA function and their role in human disease. Wiley Interdisciplinary Reviews: RNA. 2015; 6(2):173-89. PMC4390053.

68. Khoddami V, Cairns B R. Identification of direct targets and modified bases of RNA cytosine methyltransferases. Nat Biotech. 2013; 31(5):458-64. PMC3791587.

69. Hussain S, Sajini Abdulrahim A, Blanco S, Dietmann S, Lombard P, Sugimoto Y, Paramor M, Gleeson Joseph G, Odom Duncan T, Ule J, Frye M. NSun2-Mediated Cytosine-5 Methylation of Vault Noncoding RNA Determines Its Processing into Regulatory Small RNAs. Cell Reports. 2013; 4(2):255-61. PMC3730056.

70. Arnez J G, Steitz T A. Crystal structure of unmodified tRNAGln complexed with glutaminyl-tRNA synthetase and ATP suggests a possible role for pseudo-uridines in stabilization of RNA structure. Biochemistry. 1994; 33(24):7560-7. PMC pending.
71. Newby M I, Greenbaum N L. Sculpting of the spliceosomal branch site recognition motif by a conserved pseudouridine. Nat Struct Mol Biol. 2002; 9(12):958-65. PMC pending.
72. Davis D R. Stabilization of RNA stacking by pseudouridine. Nucleic Acids Res. 1995; 23(24):5020-6.
73. Newby M I, Greenbaum N L. A conserved pseudouridine modification in eukaryotic U2 snRNA induces a change in branch-site architecture. RNA. 2001; 7(06):833-45. PMC pending.
74. Newby M I, Greenbaum N L. Investigation of Overhauser effects between pseudouridine and water protons in RNA helices. Proc Natl Acad Sci U.S.A. 2002; 99(20): 12697-702. PMC pending.
75. Wu G, Xiao M, Yang C, Yu Y T. U2 snRNA is inducibly pseudouridylated at novel sites by Pus7p and snR81 RNP. The EMBO journal. 2011; 30(1):79-89. PMC3020122.
76. Meier U T. Pseudouridylation goes regulatory. The EMBO journal. 2011; 30(1):3-4. PMC3020123
77. Karikó K, Muramatsu H, Keller J M, Weissman D. Increased erythropoiesis in mice injected with submicrogram quantities of pseudouridine-containing mRNA encoding erythropoietin. Molecular Therapy. 2012. 20(5): 948-53. PMC3345990.
78. Jambhekar A, DeRisi J L. Cis-acting determinants of asymmetric, cytoplasmic RNA transport. RNA. 2007; 13(5):625-42. PMC pending.
79. Kudla G, Murray A W, Tollervey D, Plotkin J B. Coding-sequence determinants of gene expression in Escherichia coli. Science. 2009; 324(5924):255-8. PMC3902468.
80. Somogyi P, Jenner A, Brierley I, Inglis S. Ribosomal pausing during translation of an RNA pseudoknot. Mol Cell Biol. 1993; 13(11):6931-40. PMC pending.
81. Shah P, Ding Y, Niemczyk M, Kudla G, Plotkin J B. Rate-limiting steps in yeast protein translation. Cell. 2013; 153(7):1589-601. PMC3694300.
82. Tan X, Lu Z J, Gao G, Xu Q, Hu L, Fellmann C, Li M Z, Qu H, Lowe S W, Hannon G J. Tiling genomes of pathogenic viruses identifies potent antiviral shRNAs and reveals a role for secondary structure in shRNA efficacy. Proc Natl Acad Sci U.S.A. 2012; 109(3):869-74. PMC3271875.
83. Karijolich J, Yu Y-T. Converting nonsense codons into sense codons by targeted pseudouridylation. Nature. 2011; 474(7351):395-8. PMC3381908.
84. Fernández I S, Ng C L, Kelley A C, Wu G, Yu Y-T, Ramakrishnan V. Unusual base pairing during the decoding of a stop codon by the ribosome. Nature. 2013; 500(7460):107-10. PMC3732562.
85. Lee S H, Kim I, Chung B C. Increased urinary level of oxidized nucleosides in patients with mild-to-moderate Alzheimer's disease. Clinical Biochemistry. 2007; 40(13):936-8. PMC pending.
86. Grozdanov P N, Fernandez-Fuentes N, Fiser A, Meier U T. Pathogenic NAP57 mutations decrease ribonucleoprotein assembly in dyskeratosis congenita. Hum Mol Genet. 2009; 18(23):4546-51. PMC2773269.
87. Heiss N S, Knight S W, Vulliamy T J, Klauck S M, Wiemann S, Mason P J, Poustka A, Dokal I. X-linked dyskeratosis congenita is caused by mutations in a highly conserved gene with putative nucleolar functions. Nat Genet. 1998; 19(1):32-8. PMC pending.
88. Schaefer M, Pollex T, Hanna K, Tuorto F, Meusburger M, Helm M, Lyko F. RNA methylation by Dnmt2 protects transfer RNAs against stress-induced cleavage. Genes Dev. 2010; 24(15):1590-5. PMC2912555.
89. Tuorto F, Liebers R, Musch T, Schaefer M, Hofmann S, Kellner S, Frye M, Helm M, Stoecklin G, Lyko F. RNA cytosine methylation by Dnmt2 and NSun2 promotes tRNA stability and protein synthesis. Nat Struct Mol Biol. 2012; 19(9):900-5. PMC pending.
90. Kiani J, Grandjean V, Liebers R, Tuorto F, Ghanbarian H, Lyko F, Cuzin F, Rassoulzadegan M. RNA—Mediated Epigenetic Heredity Requires the Cytosine Methyltransferase Dnmt2. PLoS Genet. 2013; 9(5):e1003498. PMC3662642.
91. Metodiev M D, Spåhr H, Loguercio Polosa P, Meharg C, Becker C, Altmueller J, Habermann B, Larsson N-G, Ruzzenente B. NSUN4 Is a Dual Function Mitochondrial Protein Required for Both Methylation of 12S rRNA and Coordination of Mitoribosomal Assembly. PLoS Genet. 2014; 10(2):e1004110. PMC3916286.
92. Cámara Y, Asin-Cayuela J, Park Chan B, Metodiev Metodi D, Shi Y, Ruzzenente B, Kukat C, Habermann B, Wibom R, Hultenby K, Franz T, Erdjument-Bromage H, Tempst P, Hallberg B M, Gustafsson Claes M, Larsson N-G. MTERF4 Regulates Translation by Targeting the Methyltransferase NSUN4 to the Mammalian Mitochondrial Ribosome. Cell Metab. 2011; 13(5):527-39. PMC pending.
93. Okamoto M, Hirata S, Sato S, Koga S, Fujii M, Qi G, Ogawa I, Takata T, Shimamoto F, Tatsuka M. Frequent increased gene copy number and high protein expression of tRNA (cytosine-5-)-methyltransferase (NSUN2) in human cancers. DNA Cell Biol. 2012; 31(5):660-71. PMC pending.
94. Frye M, Watt F M. The RNA methyltransferase Misu (NSun2) mediates Myc-induced proliferation and is upregulated in tumors. Curr Biol. 2006; 16(10):971-81. PMC pending.
95. Khosronezhad N, Colagar A H, Jorsarayi S G A. T26248G-transversion mutation in exon7 of the putative methyltransferase Nsun7 gene causes a change in protein folding associated with reduced sperm motility in asthenospermic men. Reprod Fertil Dev. 2015; 27(3):471-80. PMC pending.
96. Hussain S, Tuorto F, Menon S, Blanco S, Cox C, Flores J V, Watt S, Kudo N R, Lyko F, Frye M. The Mouse Cytosine-5 RNA Methyltransferase NSun2 Is a Component of the Chromatoid Body and Required for Testis Differentiation. Mol Cell Biol. 2013; 33(8):1561-70. PMC3624257.
97. Harris T, Marquez B, Suarez S, Schimenti J. Sperm Motility Defects and Infertility in Male Mice with a Mutation in Nsun7, a Member of the Sun Domain-Containing Family of Putative RNA Methyltransferases. Biol Reprod. 2007; 77(2):376-82. PMC pending.
98. Khan M A, Rafiq M A, Noor A, Hussain S, Flores J V, Rupp V, Vincent A K, Malli R, Ali G, Khan F S. Mutation in NSUN2, which encodes an RNA methyltransferase, causes autosomal-recessive intellectual disability. Am J Hum Genet. 2012; 90(5):856-63. PMC3376419.
99. Begley U, Dyavaiah M, Patil A, Rooney J P, DiRenzo D, Young C M, Conklin D S, Zitomer R S, Begley T J. Trm9-catalyzed tRNA modifications link translation to the DNA damage response. Mol Cell. 2007; 28(5):860-70. PMC2211415.

100. Chan C T, Pang Y L J, Deng W, Babu I R, Dyavaiah M, Begley T J, Dedon P C. Reprogramming of tRNA modifications controls the oxidative stress response by codon-biased translation of proteins. Nature Commun. 2012; 3:937. PMC3535174.

101. Kaiser S, Rimbach K, Eigenbrod T, Dalpke A H, Helm M. A modified dinucleotide motif specifies tRNA recognition by TLR7. RNA. 2014; 20(9):1351-5. PMC4138318.

102. Fu D, Brophy J A N, Chan C T Y, Atmore K A, Begley U, Paules R S, Dedon P C, Begley T J, Samson L D. Human AlkB Homolog ABH8 Is a tRNA Methyltransferase Required for Wobble Uridine Modification and DNA Damage Survival. Mol Cell Biol. 2010; 30(10):2449-59. PMC2863699.

103. Saikia M, Fu Y, Pavon-Eternod M, He C, Pan T. Genome-wide analysis of $N^1$-methyl-adenosine modification in human tRNAs. RNA. 2010; 16(7):1317-27. PMC2885681.

104. Anderson J, Phan L, Hinnebusch A G. The Gcd10p/Gcd14p complex is the essential two-subunit tRNA (1-methyladenosine) methyltransferase of Saccharomyces cerevisiae. Proc Natl Acad Sci U.S.A. 2000; 97(10):5173-8. PMC pending.

105. Anderson J, Phan L, Cuesta R, Carlson B A, Pak M, Asano K, Björk G R, Tamame M, Hinnebusch A G. The essential Gcd10p-Gcd14p nuclear complex is required for 1-methyladenosine modification and maturation of initiator methionyl-tRNA. Genes Dev. 1998; 12(23):3650-62. PMC pending.

106. Li J, Yang Z, Yu B, Liu J, Chen X. Methylation Protects miRNAs and siRNAs from a 3'-End Uridylation Activity in Arabidopsis. Curr Biol. 2005; 15(16):1501-7. PMC pending.

107. Bakin A, Ofengand J. Four newly located pseudouridylate residues in Escherichia coli 23S ribosomal RNA are all at the peptidyltransferase center: analysis by the application of a new sequencing technique. Biochemistry. 1993; 32(37):9754-62. PMC pending.

108. Kiss-László Z, Henry Y, Kiss T. Sequence and structural elements of methylation guide snoRNAs essential for site-specific ribose methylation of pre-rRNA. The EMBO Journal. 1998; 17(3):797-807. PMC pending.

109. Luo G-Z, MacQueen A, Zheng G, Duan H, Dore L C, Lu Z, Liu J, Chen K, Jia G, Bergelson J, He C. Unique features of the $m^6A$ methylome in Arabidopsis thaliana. Nat Commun. 2014; 5:5630. PMC4248235.

110. Chen K, Lu Z, Wang X, Fu Y, Luo G-Z, Liu N, Han D, Dominissini D, Dai Q, Pan T, He C. High-Resolution N6-Methyladenosine (m6A) Map Using Photo-Crosslinking-Assisted m6A Sequencing. Angew Chem Int Ed. 2015; 54(5):1587-90. PMC4396828.

111. Lister R, O'Malley R C, Tonti-Filippini J, Gregory B D, Berry C C, Millar A H, Ecker J R. Highly Integrated Single-Base Resolution Maps of the Epigenome in Arabidopsis. Cell. 2008; 133(3):523-36. PMC2723732.

112. Lister R, Pelizzola M, Dowen R H, Hawkins R D, Hon G, Tonti-Filippini J, Nery J R, Lee L, Ye Z, Ngo Q-M, Edsall L, Antosiewicz-Bourget J, Stewart R, Ruotti V, Millar A H, Thomson J A, Ren B, Ecker J R. Human DNA methylomes at base resolution show widespread epigenomic differences. Nature. 2009; 462(7271):315-22. PMC2857523.

113. Yu M, Hon Gary C, Szulwach Keith E, Song C-X, Zhang L, Kim A, Li X, Dai Q, Shen Y, Park B, Min J-H, Jin P, Ren B, He C. Base-Resolution Analysis of 5-Hydroxymethylcytosine in the Mammalian Genome. Cell. 2012; 149(6):1368-80. PMC3589129.

114. Véliz E A, Easterwood L M, Beal P A. Substrate Analogues for an RNA-Editing Adenosine Deaminase: Mechanistic Investigation and Inhibitor Design. Journal of the American Chemical Society. 2003; 125(36):10867-76. PMC pending.

115. Song C-X, Szulwach Keith E, Dai Q, Fu Y, Mao S-Q, Lin L, Street C, Li Y, Poidevin M, Wu H, Gao J, Liu P, Li L, Xu G-L, Jin P, He C. Genome-wide Profiling of 5-Formylcytosine Reveals Its Roles in Epigenetic Priming. Cell. 2013; 153(3):678-91. PMC3657391.

116. Lu X, Song C-X, Szulwach K, Wang Z, Weidenbacher P, Jin P, He C. Chemical Modification-Assisted Bisulfite Sequencing (CAB-Seq) for 5-Carboxylcytosine Detection in DNA. J Am Chem Soc. 2013; 135(25):9315-7. PMC3727251.

117. Fu Y, Luo G-Z, Chen K, Deng X, Yu M, Han D, Hao Z, Liu J, Lu X, Dorzé Louis C, Weng X, Ji Q, Mets L, He C. $N^6$-Methyldeoxyadenosine Marks Active Transcription Start Sites in Chlamydomonas. Cell. 2015; 161(4):879-92. PMC4427561.

118. Zhang G, Huang H, Liu D, Cheng Y, Liu X, Zhang W, Yin R, Zhang D, Zhang P, Liu J, Li C, Liu B, Luo Y, Zhu Y, Zhang N, He S, He C, Wang H, Chen D. $N^6$-Methyladenine DNA Modification in Drosophila. Cell. 2015; 161(4):893-906. PMC pending.

119. Greer Eric L, Blanco Mario A, Gu L, Sendinc E, Liu J, Aristizábal-Corrales D, Hsu C-H, Aravind L, He C, Shi Y. DNA Methylation on $N^6$-Adenine in C. elegans. Cell. 2015; 161(4):868-78. PMC4427530.

120. Keegan L P, Gallo A, O'Connell M A. The many roles of an RNA editor. Nat Rev Genet. 2001; 2(11):869-78. PMC pending.

121. Wulff B-E, Sakurai M, Nishikura K. Elucidating the inosinome: global approaches to adenosine-to-inosine RNA editing. Nat Rev Genet. 2011; 12(2):81-5. PMC3075016.

122. Gubler U, Hoffman B J. A simple and very efficient method for generating cDNA libraries. Gene. 1983; 25(2-3):263-9. PMC3688977.

123. Makeyev E V, Bamford D H. Replicase activity of purified recombinant protein P2 of double-stranded RNA bacteriophage φ6. The EMBO Journal. 2000; 19(1):124-33. PMC1171784.

124. Chen I, Don B M, Liu D R. A general strategy for the evolution of bond-forming enzymes using yeast display. Proc Natl Acad Sci U.S.A. 2011; 108(28):11399-404. PMC3136257.

125. Dorr B M, Ham H O, An C, Chaikof E L, Liu D R. Reprogramming the specificity of sortase enzymes. Proc Natl Acad Sci U.S.A. 2014; 111(37):13343-8. PMC4169943.

126. Pepper L R, Cho Y K, Boder E T, Shusta E V. A decade of yeast surface display technology: where are we now? Comb Chem High Throughput Screen. 2008; 11(2):127-34. PMC2681324.

127. Yin J, Straight P D, McLoughlin S M, Zhou Z, Lin A J, Golan D E, Kelleher N L, Kolter R, Walsh C T. Genetically encoded short peptide tag for versatile protein labeling by Sfp phosphopantetheinyl transferase. Proc Natl Acad Sci U.S.A. 2005; 102(44):15815-20. PMC1276090.

128. Puthenveetil S, Liu D S, White K A, Thompson S, Ting A Y. Yeast display evolution of a kinetically efficient 13-amino acid substrate for lipoic acid ligase. J Am Chem Soc. 2009; 131(45):16430-8. PMC2799336.

129. Macbeth M R, Schubert H L, Vandemark A P, Lingam A T, Hill C P, Bass B L. Inositol hexakisphosphate is bound in the ADAR2 core and required for RNA editing. Science. 2005; 309(5740):1534-9. PMC1850959.
130. Savva Y, Rieder L, Reenan R. The ADAR protein family. Genome Biol. 2012; 13(12):252. PMC3580408.
131. Krueger F, Kreck B, Franke A, Andrews S R. DNA methylome analysis using short bisulfate sequencing data. Nat Meth. 2012; 9(2):145-51. PMC pending.
132. Randau L, Stanley B J, Kohlway A, Mechta S, Xiong Y, Söll D. A Cytidine Deaminase Edits C to U in Transfer RNAs in Archaea. Science. 2009; 324(5927):657-9. PMC2857566.
133. Conticello S. The AID/APOBEC family of nucleic acid mutators. Genome Biol. 2008; 9(6):229. PMC2481415.
134. Prochnow C, Bransteitter R, Klein M G, Goodman M F, Chen X S. The APOBEC-2 crystal structure and functional implications for the deaminase AID. Nature. 2007; 445(7126):447-51. PMC pending.
135. Motorin Y, Muller S, Behm-Ansmant I, Branlant C. Identification of modified residues in RNAs by reverse transcription-based methods. Methods Enzymol. 2007; 425:21-53. PMC pending.
136. Tijerina P, Mohr S, Russell R. DMS footprinting of structured RNAs and RNA-protein complexes. Nat Protoc. 2007; 2(10):2608-23. PMC2701642.
137. Pang Y L, Abo R, Levine S S, Dedon P C. Diverse cell stresses induce unique patterns of tRNA up- and down-regulation: tRNA-seq for quantifying changes in tRNA copy number. Nucleic Acids Res. 2014; 42(22):e170. PMC4267671.
138. Mohr S, Ghanem E, Smith W, Sheeter D, Qin Y, King O, Polioudakis D, Iyer V R, Hunicke-Smith S, Swamy S, Kuersten S, Lambowitz A M. Thermostable group II intron reverse transcriptase fusion proteins and their use in cDNA synthesis and next-generation RNA sequencing. RNA. 2013; 19(7):958-70. PMC3683930.
139. Trewick S C, Henshaw T F, Hausinger R P, Lindahl T, Sedgwick B. Oxidative demethylation by *Escherichia coli* AlkB directly reverts DNA base damage. Nature. 2002; 419(6903):174-8. PMC pending.
140. Aas P A, Otterlei M, Falnes P O, Vagbo C B, Skorpen F, Akbari M, Sundheim O, Bjoras M, Slupphaug G, Seeberg E, Krokan H E. Human and bacterial oxidative demethylases repair alkylation damage in both RNA and DNA. Nature. 2003; 421(6925):859-63. PMC pending.
141. Holland P J, Hollis T. Structural and mutational analysis of *Escherichia coli* AlkB provides insight into substrate specificity and DNA damage searching. PLoS ONE. 2010; 5(1):e8680. PMC2800194.
142. Yang C G, Yi C, Duguid E M, Sullivan C T, Jian X, Rice P A, He C. Crystal structures of DNA/RNA repair enzymes AlkB and ABH2 bound to dsDNA. Nature. 2008; 452(7190):961-5. PMC2587245.
143. Wang R, Zheng W, Yu H, Deng H, Luo M. Labeling substrates of protein arginine methyltransferase with engineered enzymes and matched S-adenosyl-L-methionine analogues. J Am Chem Soc. 133(20):7648-51. PMC3104021.
144. Calabretta A, Leumann C J. Base pairing and miscoding properties of 1,$N^6$-ethenoadenine- and 3,$N^4$-ethenocytosine-containing RNA oligonucleotides. Biochemistry. 2013; 52(11):1990-7. PMC pending.
145. Luo M. Current chemical biology approaches to interrogate protein methyltransferases. ACS Chem Biol.2012; 7(3):443-63. PMC3306480.
146. Bakin A, Ofengand J. Four newly located pseudouridylate residues in *Escherichia coli* 23S ribosomal RNA are all at the peptidyltransferase center: analysis by the application of a new sequencing technique. Biochemistry. 1993; 32(37):9754-62. PMC pending.
147. Bakin A, Ofengand J. Mapping of the 13 pseudouridine residues in *Saccharomyces cerevisiae* small subunit ribosomal RNA to nucleotide resolution. Nucleic Acids Res. 1995; 23(16):3290-4. PMC307190.
148. Bakin A V, Ofengand J. Mapping of pseudouridine residues in RNA to nucleotide resolution. Methods Mol Biol. 1998; 77:297-309. PMC pending.
149. Xu Y, Liu L, Lopez-Estrano C, Michaeli S. Expression studies on clustered trypanosomatid box C/D small nucleolar RNAs. J Biol Chem. 2001; 276(17):14289-98. PMC pending.
150. Mag M, Luking S, Engels J W. Synthesis and selective cleavage of an oligodeoxynucleotide containing a bridged internucleotide 5'-phosphorothioate linkage. Nucleic Acids Res. 1991; 19(7):1437-41. PMC333898.
151. Satterlee J S, Basanta-Sanchez M, Blanco S, Li J B, Meyer K, Pollock J, Sadri-Vakili G, Rybak-Wolf A. Novel RNA modifications in the nervous system: form and function. J Neurosci. 2014; 34(46):15170-7. PMC4402329.
152. Chen C, Tuck S, Bystrom A S. Defects in tRNA modification associated with neurological and developmental dysfunctions in *Caenorhabditis elegans* elongator mutants. PLoS Genet. 2009; 5(7):e1000561. PMC2702823.
153. Honda K, Smith M A, Zhu X, Baus D, Merrick W C, Tartakoff A M, Hattier T, Harris P L, Siedlak S L, Fujioka H, Liu Q, Moreira P I, Miller F P, Nunomura A, Shimohama S, Perry G. Ribosomal RNA in Alzheimer disease is oxidized by bound redox-active iron. J Biol Chem. 2005; 280(22):20978-86. PMC pending.
154. LaSalle J M, Powell W T, Yasui D H. Epigenetic layers and players underlying neurodevelopment. Trends Neurosci. 2013; 36(8):460-70. PMC3735843.
155. Bonaguidi M A, Wheeler M A, Shapiro J S, Stadel R P, Sun G J, Ming G L, Song H. In vivo clonal analysis reveals self-renewing and multipotent adult neural stem cell characteristics. Cell. 2011; 145(7):1142-55. PMC3124562.
156. Christian K M, Song H, Ming G L. Functions and dysfunctions of adult hippocampal neurogenesis. Annu Rev Neurosci. 2014; 37:243-62. PMC pending.
157. Guo J U, Ma D K, Mo H, Ball M P, Jang M R, Bonaguidi M A, Balazer J A, Eaves H L, Xie B, Ford E, Zhang K, Ming G L, Gao Y, Song H. Neuronal activity modifies the DNA methylation landscape in the adult brain. Nat Neurosci. 2011; 14(10):1345-51. PMC3183401.
158. Guo J U, Su Y, Zhong C, Ming G L, Song H. Hydroxylation of 5-methylcytosine by TET1 promotes active DNA demethylation in the adult brain. Cell. 2011; 145(3):423-34. PMC3088758.
159. Chen E, Sharma M R, Shi X, Agrawal R K, Joseph S. Fragile X mental retardation protein regulates translation by binding directly to the ribosome. Mol Cell. 54(3):407-17. PMC4019695.
160. Darnell J C, Van Driesche S J, Zhang C, Hung K Y, Mele A, Fraser C E, Stone E F, Chen C, Fak J J, Chi S W, Licatalosi D D, Richter J D, Darnell R B. FMRP stalls ribosomal translocation on mRNAs linked to synaptic function and autism. Cell. 2011; 146(2):247-61. PMC3232425.

161. Maxwell E K, Campbell J D, Spira A, Baxevanis A D. SubmiRine: assessing variants in microRNA targets using clinical genomic data sets. Nucleic Acids Res. 2015; 43(8):3886-98. PMC pending.
162. Song J, Zhong C, Bonaguidi M A, Sun G J, Hsu D, Gu Y, Meletis K, Huang Z J, Ge S, Enikolopov G, Deisseroth K, Luscher B, Christian K M, Ming G L, Song H. Neuronal circuitry mechanism regulating adult quiescent neural stem-cell fate decision. Nature. 2012; 489(7414): 150-4. PMC3438284.
163. Ge S, Goh E L, Sailor K A, Kitabatake Y, Ming G L, Song H. GABA regulates synaptic integration of newly generated neurons in the adult brain. Nature. 2006; 439 (7076):589-93. PMC1420640.
164. Duan X, Chang J H, Ge S, Faulkner R L, Kim J Y, Kitabatake Y, Liu X B, Yang C H, Jordan J D, Ma D K, Liu C Y, Ganesan S, Cheng H J, Ming G L, Lu B, Song H. Disrupted-In-Schizophrenia 1 regulates integration of newly generated neurons in the adult brain. Cell. 2007; 130(6):1146-58. PMC2002573.
165. Song J, Sun J, Moss J, Wen Z, Sun G J, Hsu D, Zhong C, Davoudi H, Christian K M, Toni N, Ming G L, Song H. Parvalbumin interneurons mediate neuronal circuitry-neurogenesis coupling in the adult hippocampus. Nat Neurosci. 2013; 16(12):1728-30. PMC4096812.
166. Ge S, Yang C H, Hsu K S, Ming G L, Song H. A critical period for enhanced synaptic plasticity in newly generated neurons of the adult brain. Neuron. 2007; 54(4):559-66. PMC2040308.
167. Kim J Y, Duan X, Liu C Y, Jang M H, Guo J U, Pow-anpongkul N, Kang E, Song H, Ming G L. DISC1 regulates new neuron development in the adult brain via modulation of AKT-mTOR signaling through KIAA1212. Neuron. 2009; 63(6):761-73. PMC3075620.
168. Ma D K, Jang M H, Guo J U, Kitabatake Y, Chang M L, Pow-Anpongkul N, Flavell R A, Lu B, Ming G L, Song H. Neuronal activity-induced Gadd45b promotes epigenetic DNA demethylation and adult neurogenesis. Science. 2009; 323(5917):1074-7. PMC2726986.
169. Song C X, Szulwach K E, Fu Y, Dai Q, Yi C, Li X, Li Y, Chen C H, Zhang W, Jian X, Wang J, Zhang L, Looney T J, Zhang B, Godley L A, Hicks L M, Lahn B T, Jin P, He C. Selective chemical labeling reveals the genome-wide distribution of 5-hydroxymethylcytosine. Nat Biotechnol. 2011; 29(1):68-72. PMC3107705.
170. Yu H, Su Y, Shin J, Zhong C, Guo J U, Weng Y L, Gao F, Geschwind D H, Coppola G, Ming G L, Song H. Tet3 regulates synaptic transmission and homeostatic plasticity via DNA oxidation and repair. Nat Neurosci. 2015, advance online publication. PMC pending.

---

The invention claimed is:

1. A method for detecting a $N^6$-methyladenosine in a target ribonucleic acid (RNA) comprising:
   contacting a target RNA comprising (1) an unmodified adenosine and (2) a $N^6$-methyladenosine with an adenosine deaminase enzyme to generate a deaminated RNA comprising (i) an inosine and (ii) the $N^6$-methyladenosine; and
   sequencing the deaminated RNA to detect the $N^6$-methyladenosine.

2. The method of claim 1, further comprising contacting an additional target RNA comprising an additional $N^6$-methyladenosine with a demethylating enzyme to generate a demethylated RNA; contacting the demethylated RNA with an additional adenosine deaminase enzyme to produce a control RNA; and sequencing the control RNA.

3. The method of claim 2 further comprising comparing the sequence of the deaminated RNA to the sequence of the demethylated RNA.

4. The method of claim 1, wherein the target RNA is in a duplex with a complementary strand of RNA or DNA.

5. The method of claim 4, wherein the complementary strand is a complementary strand of DNA.

6. The method of claim 5, wherein the method further comprises, prior to sequencing the deaminated RNA, the steps of: a) generating a complementary DNA strand that is complementary to the target RNA and hybridizing the complementary DNA strand to the target RNA to generate an RNA-DNA duplex; b) contacting the RNA-DNA duplex with the adenosine deaminase enzyme; and c) contacting the RNA-DNA duplex with a DNA digesting agent to digest the complementary DNA strand.

7. The method of claim 1, wherein the target RNA is mRNA, lncRNA, pri-microRNA, pre-piRNA, rRNA, tRNA, snoRNA, or snRNA.

8. The method of claim 7, wherein the target RNA is mRNA or lncRNA.

9. The method of claim 1, wherein the method further comprises, prior to contacting the target RNA with the adenosine deaminase enzyme, generating a nucleic acid strand that is complementary to the target RNA and hybridizing the complementary nucleic acid strand to the target RNA, wherein generating the nucleic acid strand that is complementary to the target RNA comprises synthesis of a nucleic acid strand complementary to the target RNA, and wherein the synthesis of the nucleic acid strand comprises a synthesis reaction composition comprising $N^6$-methyladenosine triphosphate.

10. The method of claim 9, wherein the complementary nucleic acid strand is a complementary RNA strand.

11. The method of claim 1, wherein the target RNA comprises a known sequence, and wherein the method further comprises comparing the known sequence with the sequence of the deaminated RNA.

12. The method of claim 1, wherein contacting the target RNA with the adenosine deaminase enzyme is done in the presence of guanosine triphosphate (GTP).

13. The method of claim 1, wherein the method further comprises:
   providing a quantification control RNA comprising a known percentage of $N^6$-methyladenosine; contacting the quantification control RNA with the adenosine deaminase enzyme to generate a deaminated quantification control RNA; and sequencing the deaminated quantification control RNA.

14. The method of claim 1, wherein the adenosine deaminase enzyme is *Drosophila* RNA adenosine deaminase.

15. A method for detecting a $N^6$-methyladenosine in a target ribonucleic acid (RNA) comprising:
   a) providing a target RNA comprising (1) an unmodified adenosine and (2) the $N^6$-methyladenosine;
   b) generating a DNA strand that is complementary to the target RNA and hybridizing the complementary DNA strand to the target RNA to generate a RNA-DNA duplex comprising the target RNA;
   c) contacting the RNA-DNA duplex with an RNA adenosine deaminase (ADAR) enzyme to generate a deaminated RNA comprising (1) an inosine and (2) the $N^6$-methyladenosine;
   d) contacting the RNA-DNA duplex with a DNA digesting agent to digest the complementary DNA strand; and
   e) sequencing the deaminated RNA to detect the $N^6$-methyladenosine.

16. The method of claim 15, wherein the adenosine deaminase enzyme is *Drosophila* RNA adenosine deaminase.

* * * * *